United States Patent
Tissot et al.

(10) Patent No.: US 10,570,190 B2
(45) Date of Patent: Feb. 25, 2020

(54) IMMUNOGLOBULIN FRAMEWORKS WHICH DEMONSTRATE ENHANCED STABILITY IN THE INTRACELLULAR ENVIRONMENT AND METHODS OF IDENTIFYING SAME

(71) Applicant: ESBATech, an Alcon Biomedical Research Unit LLC, Schlieren (CH)

(72) Inventors: Kathrin Tissot, Deutschland (DE); Stefan Ewert, Zurich (CH); Adrian Auf Der Maur, Zurich (CH); Alcide Barberis, Zurich (CH); Dominik Escher, Huenenberg (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/175,002

(22) Filed: Oct. 30, 2018

(65) Prior Publication Data

US 2019/0119361 A1    Apr. 25, 2019

Related U.S. Application Data

(62) Division of application No. 15/340,195, filed on Nov. 1, 2016, now Pat. No. 10,125,186, which is a division of application No. 14/469,276, filed on Aug. 26, 2014, now Pat. No. 9,518,108, which is a division of application No. 10/515,241, filed as application No. PCT/EP03/05324 on May 21, 2003, now Pat. No. 8,853,362.

(60) Provisional application No. 60/438,256, filed on Jan. 3, 2003, provisional application No. 60/382,649, filed on May 22, 2002.

(51) Int. Cl.
  *G01N 33/543*  (2006.01)
  *C07K 16/00*  (2006.01)
  *G01N 33/68*  (2006.01)
  *A61K 48/00*  (2006.01)

(52) U.S. Cl.
  CPC ......... *C07K 16/00* (2013.01); *G01N 33/6857* (2013.01); *A61K 48/00* (2013.01); *C07K 2317/21* (2013.01); *C07K 2317/55* (2013.01); *C07K 2317/567* (2013.01); *C07K 2317/622* (2013.01); *C07K 2317/80* (2013.01); *C07K 2317/82* (2013.01); *C07K 2317/94* (2013.01)

(58) Field of Classification Search
  None
  See application file for complete search history.

(56) References Cited

U.S. PATENT DOCUMENTS 5,817,311 A  10/1998  Bazin et al.
6,828,422 B1  12/2004  Achim et al.

FOREIGN PATENT DOCUMENTS

| CA | 2408513 A1 | 11/2001 |
|---|---|---|
| JP | 2004506369 A | 2/2004 |
| WO | 2001048017 A1 | 7/2001 |

OTHER PUBLICATIONS

Hanes et al. (Nature Biotechnology, vol. 18, pp. 1287-1292, Dec. 2000). (Year: 2000).*
Krebber, et al.; "Reliable cloning of functional antibody variable domains from hybridomas and spleen cell repertoires employing a reengineered phage display system", Journal of Immunological Methods; vol. 201; pp. 35-55 (1997).
Sheets et al.;"Efficient construction of a large nonimmune phage antibody library: The production of high-affinity human single-chain antibodies to protein antigens"; Proc. Natl. Acad. Sci.; Cell Biology ; vol. 95 ; pp. 6157-6162 (May 1998).
European Extended Search Report; Application Serial No. 10010455.3.
Auf Der Maur et al.; "Antigen-independent selection of stable intracellular single-chain antibodies" , FEBS Letters; vol. 508; No. 03 ; pp. 407-412 (Nov. 23, 2001).
Hanes et al. (Nature Biotechnology, vol. 18, pp. 1287-1292, Dec. 2000).
Kabat et al. "Sequencing of Proteins of Immunological Interest", Fourth Edition (1987).
The Biology Project, The University of Arizona, 2000. www.biology.arizona.edu/immunology/tutorials/antibody/prob_set/02t.html.
Cochet et al. (Molecular Immunology vol. 35, pp. 1097-1110 , 1998).
Cheadle et al. (Mol. Immunol. vol. 29 (1) pp. 21-30, 1992) Abstract only.
Visintin et al., "The Intracellular Antibody Capture Technology (IACT): Towards a Consensus Sequence for Intracellular Antibodies," Journal of Molecular Biology, vol. 317, No. 01, 2002, pp. 73-83.
Ewert et al., "Structure-Based Improvement of Biophysical Properties of Immunoglobulin VH Domains With a Generalized Approach," Biochemistry 2003, 42, pp. 1517-1528.
International Search Report Corresponding to International Patent Application Serial No. PCT/EP03/05324, European Patent Office, dated Nov. 14, 2003. 08 pages.
European Search Report Corresponding to European Patent Application Serial No. 037 32 434.0, dated May 23, 2005 , 02 Pages.
Knappik et al., "Fully Synthetic Human Combinatorial Antibody Libraries (HuCAL) Based on Modular Consensus Frameworks and CDRs Randomized With Trinucleotides," Journal of Molecular Biology (2000) 296 , 57-86.

(Continued)

*Primary Examiner* — Meera Natarajan
(74) *Attorney, Agent, or Firm* — Jason J. Derry

(57) ABSTRACT

Compositions are provided, which can be used as frameworks for the creation of very stable and soluble single-chain Fv antibody fragments. These frameworks have been selected for intracellular performance and are thus ideally suited for the creation of scFv antibody fragments or scFv antibody libraries for applications where stability and solubility are limiting factors for the performance of antibody fragments, such as in the reducing environment of a cell. Such frameworks can also be used to identify highly conserved residues and consensus sequences which demonstrate enhanced solubility and stability.

1 Claim, 54 Drawing Sheets

Specification includes a Sequence Listing.

(56) References Cited

OTHER PUBLICATIONS

Worn Arne et al. "Correlation between in Vitro Stability and in Vivo Performance of Anti-GCN4 Intrabodies as Cytoplasmic Inhibitors" The Journal of Biological Chemistry, vol. 275, No. 4, pp. 2795-2803, 2000.

Rajpal Arvind and Thomas G. Turi "Intracellular Stability of Anti-caspase-3 Intrabodies Determines Efficacy in Retargeting the Antigen" The Journal of Biological Chemistery, vol. 276, No. 35, pp. 33139-33146, 2001.

\* cited by examiner

Intracellular performance after Quality control selection in yeast *S. cerevisiae*

Soluble expression in the cytoplasm of yeast *S. cerevisiae*

Expression behavior in E.coli

Intracellular performance of selected novel frameworks in different mammalian cell lines Resistance towards aggregation at 37°C Resistance towards aggregation and protease degradation in human serum FIG. 12  Alignment of selected VH domain sequences

| AHo | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|
| VH3 | | | | | | | | | | | | | | | | | | | | | | | | | | | | | | |
| a02 | E | V | Q | L | V | E | T | . | G | G | G | L | V | Q | P | G | G | S | L | R | L | S | C | A | A | S | G | . | F | T |
| *a44* | Q | V | Q | L | V | Q | S | . | G | G | G | L | V | Q | P | G | G | S | L | R | L | S | C | A | A | S | G | . | F | T |
| a25 | Q | V | Q | L | V | E | S | . | G | G | G | L | V | Q | P | G | G | S | L | R | L | S | C | A | A | S | N | . | F | D |
| a68 | E | V | Q | L | V | E | T | . | G | G | G | L | V | Q | P | G | R | S | L | R | L | S | C | T | T | S | G | . | F | T |
| a28 | Q | V | Q | L | V | E | S | . | G | G | G | V | V | Q | P | G | R | S | L | R | L | S | C | A | A | S | G | . | F | T |
| a01 | E | V | Q | L | V | Q | S | . | G | G | G | L | V | Q | P | G | G | S | L | R | L | S | C | A | A | S | G | . | F | T |
| a41 | E | V | Q | L | V | E | S | . | G | G | G | V | V | Q | P | G | K | S | L | R | L | S | C | A | A | S | G | . | F | T |
| a09 | Q | V | Q | L | V | E | S | . | G | G | G | L | V | Q | P | G | G | S | L | R | L | S | C | A | A | S | G | . | F | S |
| a04 | . | V | Q | L | V | E | S | . | G | G | G | L | V | K | P | G | G | S | L | R | L | S | C | A | A | S | G | . | F | S |
| *a43* | E | V | Q | L | V | E | S | . | G | G | G | L | V | Q | P | G | G | S | L | R | L | S | C | A | A | S | G | . | F | T |
| a08 | Q | V | Q | L | V | E | S | . | G | G | G | L | V | K | P | G | G | S | L | R | L | S | C | A | A | S | G | . | F | T |
| a15 | Q | V | Q | L | V | Q | S | . | G | G | G | L | V | Q | P | G | G | S | L | R | L | S | C | A | A | S | G | . | F | T |
| a22 | E | V | Q | L | V | E | T | . | G | G | G | L | V | K | P | G | G | S | L | R | L | S | C | A | A | S | G | . | F | T |
| a47 | E | V | Q | L | V | Q | S | . | G | G | G | L | V | Q | P | G | G | S | L | K | L | S | C | A | A | S | G | . | F | T |
| k IV 107 | Q | V | Q | L | V | Q | S | . | G | G | G | L | V | K | P | G | G | S | L | R | L | S | C | A | A | S | G | . | F | T |
| a fw1 | Q | M | Q | L | V | Q | S | . | G | G | G | V | V | Q | P | G | R | S | L | R | L | S | C | A | V | S | G | . | F | A |
| a fw5 | Q | V | Q | L | V | E | S | . | G | G | G | L | V | Q | P | G | G | S | L | R | L | S | C | A | A | S | G | . | F | T |
| *a fw10* | E | V | Q | L | V | E | S | . | G | G | G | V | A | Q | P | G | G | S | L | R | V | S | C | A | A | S | G | . | F | S |
| a fw8 | Q | V | Q | L | Q | E | S | . | G | G | D | L | V | K | P | G | Q | S | L | R | L | S | C | I | A | S | G | . | F | S |
| k III 25 | E | V | Q | L | V | E | S | . | G | G | G | F | V | Q | P | G | G | S | L | R | L | S | C | A | A | S | G | . | F | N |
| k I 12 | E | V | Q | L | V | E | S | . | G | G | G | L | V | K | P | G | G | S | L | R | L | S | C | A | A | S | G | . | L | T |
| a61 | E | V | Q | L | V | E | S | . | G | G | G | V | V | Q | P | G | R | S | L | R | L | H | C | A | A | S | G | . | F | T |
| k IV 103 | Q | V | Q | L | V | Q | S | . | G | G | G | L | V | Q | P | G | R | S | L | R | L | S | C | A | A | S | G | . | F | T |
| a18 | Q | V | Q | L | V | E | S | . | G | G | G | L | V | Q | P | G | T | S | L | R | L | S | C | A | A | S | G | . | F | T |
| a69 | E | V | Q | L | V | E | S | . | G | G | G | L | V | Q | P | G | R | S | L | R | L | S | C | V | A | S | G | . | F | I |
| a65 | E | V | Q | L | V | E | T | . | G | G | G | V | V | Q | P | G | G | S | L | R | L | S | C | A | T | S | G | . | F | T |
| a59 | E | V | Q | L | V | E | S | . | G | G | G | L | V | K | T | G | G | S | L | R | L | S | C | A | A | S | G | . | F | T |
| a58 | E | V | Q | L | V | E | S | . | G | G | G | L | V | Q | P | G | G | S | L | R | L | S | C | A | A | S | G | . | F | T |
| a51 | E | V | Q | L | V | E | S | . | G | G | G | L | V | K | P | G | G | S | L | R | L | S | C | A | V | S | G | . | F | T |
| k IV 98 | Q | V | Q | L | Q | E | S | . | G | G | I | V | V | Q | P | G | G | S | L | R | L | S | C | A | A | A | G | . | F | T |
| k III 10 | E | V | Q | L | V | E | S | . | G | G | G | L | V | K | P | G | G | S | L | R | L | S | C | A | A | S | G | . | F | T |
| k III 8 | Q | V | Q | L | V | E | S | . | G | G | G | L | V | K | P | G | G | S | L | R | L | S | C | A | A | S | G | . | F | T |
| a53 | Q | V | Q | L | V | Q | S | . | G | G | G | V | V | Q | P | G | R | S | L | R | L | S | C | A | A | S | G | . | F | T |
| a49 | . | V | Q | L | V | E | T | . | G | G | G | L | V | Q | P | G | R | S | L | R | L | S | C | T | A | S | G | . | F | T |
| a24 | Q | V | Q | L | V | Q | S | . | G | G | G | V | V | Q | P | G | G | S | L | R | L | S | C | D | A | S | G | . | F | N |
| k II 114 | E | V | Q | L | V | E | S | . | G | G | G | L | V | Q | P | G | G | S | L | R | L | S | C | A | A | S | G | . | F | T |
| k III 23 | E | V | Q | L | V | E | T | . | G | G | G | L | V | P | P | G | G | S | L | R | L | S | C | A | A | S | G | . | F | I |
| a46 | Q | V | Q | L | V | Q | S | . | G | G | G | L | V | K | P | G | G | S | V | R | L | S | C | A | A | S | G | . | F | T |

FIG. 12 (continued): Alignment of selected VH domain sequences

| AHo | 1 2 3 4 5 6 7 8 9 10 11 12 13 14 15 16 17 18 19 20 21 22 23 24 25 26 27 28 29 30 |
|---|---|
| VH3 | |
| a10 | E V Q L V Q S . G G G L V K P G G S L R L S C A A S G . F I |
| k II 129 | Q V Q L V Q S . G G G L V Q P G G S L R L S C A A S G . F T |
| k IV 135 | E V Q L V Q S . G G G L V Q P G K S L R L S C E A S G . F T |
| a60 | E V Q L V Q S . G G G V V Q P G R S L R L S C V A S G . F T |
| k I 32 | E V Q L V E T . G G G L V Q P G G S L R L S C A A S G . F T |
| k II 190 | Q V Q L V Q S . G G G L V Q P G G S L R L S C A A S G . F T |
| k I 22 | E V Q L V E T . G G G L V Q P G G S L R L S C A A S G . F T |
| k I 33 | E V Q L V E T . G G G L V Q P G G S L R L S C A A S G . F N |
| k I 13 | Q V Q L V E S . G G G L V Q P G G S L T L S C A A S G . F T |
| k I 61 | Q L Q L Q E S . G G A L I Q P G G S L R L S C A A S G . F T |
| k III 18 | E V Q L V E A . G G G L V Q P G G S L R L S C E V S G . F T |
| k III 20 | E V Q L V E T . G G G L V Q P G G S L R L S C V P S T . F T |
| k II 10 | E V Q L V E T . G G G L V Q P G R S L R L S C A A S G . F S |
| k II 84A | Q V Q L V Q S . G G G L V Q P G R S L R L S C A A S G . F T |
| k I 19 | Q V Q L Q Q S . G G G L V Q P G R S L R L S C A A S G . F N |
| k I 17 | Q L Q L Q E S . G G G L V E P G R S L R L S C A A S G . F D |
| k III 22 | Q V Q L V E S . G G S L V Q P G G S L R L S C S A S G . F T |
| k I 24 | E V Q L V Q S . G G G V V Q P G V S L R L S C A A S G . F N |
| k II 29 | E V Q L V E T . G G G V V Q P G V S L R L S C A A S G . F N |
| k I 9 | Q V Q L Q E S . G G G L V Q P G G S L R V S C A A S G . F T |
| VH1a | |
| a71 | Q V Q L V Q S . G A E V K E P G S S V K V S C E V S G . G T |
| a62 | Q V Q L V Q S . G A E V K K P G S S V K V S C K A S G . G T |
| k I 27 | Q M Q L V Q S . G A E V M Q P G S S V R V S C K A S G . D T |
| a34 | Q M Q L V Q S . G A E L K K P G S S V K V S C K A S G . G T |
| a45 | E V Q L V Q S . G A E V K K P G S S V K V S C K A S G . G T |
| k II 9a | E V Q L V E S . G A E V K K P G S S V K V S C K A S G . G T |
| k IV 78 | Q V Q L V Q S . G A E V K K P G S S L K I S C K A S G . G T |
| k I 47 | E V Q L V Q S . G A E V M K P G S S V K V S C K A S G . G T |
| k I 64 | Q V Q L V E S . G A E V K K S G S S V K V S C K T S G . G S |
| k II 124 | Q V Q L V E S . G A E V K K P G A S V K V S C K A S G . G P |
| k III 11 | Q V Q L V E S . G A E V K K P G S S V K V S C K V S G . G T |
| k I 34 | Q V Q L V E S . G A E L K E P G E S L K I S C T L S G . V T |

FIG. 12 (continued): Alignment of selected VH domain sequences

| AHo | 1 2 3 4 5 6 7 8 9 10 11 12 13 14 15 16 17 18 19 20 21 22 23 24 25 26 27 28 29 30 |
|---|---|
| VH1b | |
| a21 | Q M Q L V Q S . G A E V K K P G A S V R V S C Q A S G . Y T |
| * a33 * | Q V Q L V Q S . G A E V K K P G A S V K V S C T A S G . Y S |
| a54 | Q V Q L V Q S . G A E V K K P G A S V K V S C K V S G . Y S |
| k II 86A | Q V Q L V Q S . G A E L V R S G A S V K L S C T A S G . F N |
| k I 65 | Q V Q L V Q S . G T E V K R P G A S V K V S C K A S G . Y T |
| k II 42 | Q V Q L V Q S . G A E V K K P G A S V K V S C K V Y G . K S |
| k I 37 | E V Q L V Q S . G A E L M K P G A S V K I S C K A T G . Y T |
| k II 205 | Q V Q L V Q S . G A E L V R S G A S V K L S C T A S G . F N |
| k IV 25 | E V R L V Q S . G T E V K K P G A S V K V S C K T S G . Y S |
| k I 54 | Q V Q L V E S . G P E V K E P G A S V N V A C K T S G . Y I |
| k II 19 | Q V Q L V Q S . G A E V K M P G A S V K V S C K V S G . S S |
| k II 87 | E V Q L V E S . G A E V Q K P G A S V N I S C K A S G . S T |
| k II 20 | Q V Q L V E S . G A E V R K P G A S V T V S C K V S G . S M |
| k II 136 | Q V Q L Q E S . G A E L K K P G A S V K V S C N V S G . Y S |
| VH4 | |
| a72 | E V Q L V E S . G P G L V K P S Q T L S L T C G V S G . D A |
| a17 | Q V Q L V E S . G P G L V T P S E T L S L T C T V S G . G S |
| a48 | Q V Q L Q E S . G P G L V K P S E T L S L V C T V S D . Y P |

FIG. 12 (continued): Alignment of selected VH domain sequences

| AHo | 31 32 33 34 35 36 37 38 39 40 | 41 42 43 44 45 46 47 | 48 49 50 | 51 52 53 54 55 56 57 | 58 59 60 61 |
|---|---|---|---|---|---|
| VH3 | | | | | |
| a02 | F S N . . . . . | Y W M H W V R | Q G P | G K G L V R V A | R I N T D |
| *a44* | F S S . . . . . | Y A M S W V R | Q A P | G K G L E W V S A | I S G S |
| a25 | F S T . . . . . | Y W M T W L R | Q F P | G K G L E W V G R | I K S N |
| a68 | F D D . . . . . | Y C L S W V R | Q A P | E K G L E W V G F | I R S K |
| a28 | F N D . . . . . | Y A F H W V R | Q A P | G K G L E W V S G | I S W N |
| a01 | F S N . . . . . | F A M S W V R | Q A P | G K G L E W V S A | I S G S |
| a41 | F S R . . . . . | Y G M H W V R | Q A P | G K G L E W V G L | I S Y D |
| a09 | L S P . . . . . | Y D L H W I R | Q P A | G K G L E W V S S | I G I . |
| a04 | F S N . . . . . | T W M S W V R | Q A P | G K G L E W V G R | I K S K |
| *a43* | F S S . . . . . | Y A M S W V R | Q A P | G K G L E W V S A | I S G S |
| a08 | F N N . . . . . | A W M S W V R | Q A P | G K G L E W I G R | I K S N |
| a15 | F S S . . . . . | Y A M S W V R | Q A P | G K G L E W V S S | I S G S |
| a22 | L N N . . . . . | A W M S W V R | Q A P | G K G L E W V G R | I K S K |
| a47 | F S G . . . . . | S A M H W V R | Q A S | G K G L E W V G R | I K T T |
| k IV 107 | F S S . . . . . | Y S M N W V R | Q A P | G K G L E W V S S | I S S S |
| a fw1 | F N D . . . . . | Y D M H W V R | Q A P | G K G L E W V A G | I N W N |
| a fw5 | F S D . . . . . | Y A M T W V R | Q A P | G K G L E W V S G | I S A S |
| *a fw10* | F S S . . . . . | Y A M Q W V R | Q A P | G K G L E W V A V | I S N D |
| a fw8 | F G D . . . . . | Y T M S W F R | Q A P | G K G L E W V G F | I R S K |
| k III 25 | F R S . . . . . | H W M S W V R | Q A P | G K G P E W V A N | I N P E |
| k I 12 | F S S . . . . . | A W I N W V R | Q T P | A K G L E W V G R | I K D . |
| a61 | F S N . . . . . | Y G M H W V R | Q V P | G K G L E W V A G | I S Y D |
| k IV 103 | F D D . . . . . | Y A M H W V R | Q A P | G K G L E W V S G | I S W N |
| a18 | F D N . . . . . | Y A M H W V R | Q A P | G K R L E W V S A | I S W N |
| a69 | F D D . . . . . | Y V M H W V R | Q A P | G K G L E W V S G | I S W N |
| a65 | F S T . . . . . | H A M N W V R | Q A P | G K G L E C V S T | I S G T |
| a59 | F S S . . . . . | Y S M N W V R | Q A P | G K G L E W V S Y | I S P . |
| a58 | V S D . . . . . | S Y M N W V R | Q A P | G K G L E W V S V | L Y S . |
| a51 | F S N . . . . . | T W M N W V R | Q A P | G K G L E W V G R | I K G N |
| k IV 98 | F S N . . . . . | Y A M N W V R | Q A P | G K G L E W V S S | V S R A |
| k III 10 | F S K . . . . . | A W M N W V R | Q T P | A K G L E W V G R | I R S N |
| k III 8 | F S N . . . . . | A W M N W V R | Q T P | A K G L E W V G R | I K S N |
| a53 | F S F . . . . . | F A M H W V R | Q A P | G K G L E W V A V | I S A D |
| a49 | F G D . . . . . | Y A M S W V R | Q A P | G K G L E W V G F | I R S K |
| a24 | F N L . . . . . | Y G M H W V R | Q A P | G K G L E W V A V | I S D D |
| k II 114 | V S S . . . . . | N Y M S W V R | Q A P | G K G L E W V S V | I Y S . |
| k III 23 | F T D . . . . . | Y W M S W V R | Q A P | G K G L E W V A N | I K Q D |
| a46 | F D D . . . . . | Y Y M T W I R | R A P | G K G L E W I S Y | I S G S |

FIG. 12 (continued): Alignment of selected VH domain sequences

| AHo | 31 32 33 34 35 36 37 38 39 40 | 41 42 43 44 45 46 47 | 48 49 50 | 51 52 53 54 55 56 57 | 58 59 60 61 |
|---|---|---|---|---|---|
| VH3 | | | | | |
| a10 | F S D . . . . . Y Y M S W | I R Q T P G K | G L E W | V S Y I T S S | |
| k II 129 | F D D . . . . . Y A M Y W | V R Q A P G K | G L E W | V S G L S W N | |
| k IV 135 | F D D . . . . . Y S M H W | V R Q A P G K | G L E W | V S G L S W N | |
| a60 | F S T . . . . . Y G M H W | V R Q A P G E | G L E W | V A I I S S D | |
| k I 32 | F R N . . . . . Y G M H W | V R Q A P G K | G L E W | V S I I H Y D | |
| k II 190 | L N N . . . . . Y A V S W | V R Q A P G K | G L E W | V S G I T G S | |
| k I 22 | F S D . . . . . H Y M D W | V R Q A P G K | G L E W | V S Y I T R S | |
| k I 33 | F S N . . . . . Y A M S W | V R Q A P G K | G L D W | V S G I S G S | |
| k I 13 | F R N . . . . . F A M S W | V R Q A P G K | G L E W | V S S I S K S | |
| k I 61 | F S S . . . . . Y T M S W | V R Q A P G K | G L E W | V S A I T G D | |
| k III 18 | F S T . . . . . Y E M H W | V R Q A P G K | G L E W | I A Y I N T G | |
| k III 20 | V S G . . . . . Y E M N W | V R Q A P G K | G L E W | I S Y M N R . | |
| k II 10 | F D D . . . . . Y G M H W | V R Q T P G Q | G L E W | V S G I S W N | |
| k II 84A | F G D . . . . . Y G M H W | V R Q V P G K | G L E W | V S G I S W N | |
| k I 19 | F D D . . . . . Y A M H W | V R Q A P G K | G L E W | V S G I S W N | |
| k I 17 | F D N . . . . . Q V M H W | V R Q V P G K | G L E W | V S G I N W N | |
| k III 22 | F T D . . . . . Y W M A W | V R Q A P G K | G L D W | V A N I N Q E | |
| k I 24 | F R S . . . . . T G M H W | V R Q A P G Q | G P E W | V A G I S F D | |
| k II 29 | F R S . . . . . T G M H W | V R Q A P G Q | G P E W | V A G I S F D | |
| k I 9 | V N N . . . . . Y Y M S W | V R Q A P G K | G L E W | V A F S S S D | |
| VH1a | | | | | |
| a71 | F S S . . . . . Y P I A W | V R Q A P G Q | G L E W | L G R I I P M | |
| a62 | F G K . . . . . H A I S W | V R Q A P G Q | G L E W | M G G I . . I | |
| k I 27 | F S S . . . . . Y T F N W | V R Q A P G Q | G L E W | M G G I I P . | |
| a34 | F S S . . . . . H A I S W | V R Q A P G Q | G L E W | M G G I . . I | |
| a45 | F R S . . . . . Y A I N W | V R Q A P G Q | G L E W | M G G I . . I | |
| k II 9a | F S S . . . . . Y A I N W | V R Q A P G Q | G L E W | M G G I I P . | |
| k IV 78 | F N T . . . . . D H F N W | V R Q A P G Q | G L E W | M G G I I P F | |
| k I 47 | F S T . . . . . S P L T W | M R Q A P G Q | G F E W | M G G I I P . | |
| k I 64 | L S S . . . . . F S I S W | V R Q A P G Q | G L E W | I G G I I P . | |
| k II 124 | F R S . . . . . S P M S W | L R Q A P G Q | G L E W | M G G I I S . | |
| k III 11 | F S S . . . . . Y T I N W | V R Q A P G Q | R P E L | M G G I I P . | |
| k I 34 | F S N . . . . . S W I D W | V R Q M P G K | G L E W | V G L I Y A . | |

FIG. 12 (continued): Alignment of selected VH domain sequences

| AHo | 31 32 33 34 35 36 37 38 39 | 40 41 42 43 44 45 46 47 | 48 49 50 | 51 52 53 54 55 56 57 | 58 59 60 61 |
|---|---|---|---|---|---|
| VH1b | | | | | |
| a21 | F T G . . . . . H | Y M H W V R Q | V P G | Q G L Q W M G | W L N P D |
| * a33 * | F T G . . . . . Y | F L H W V R Q | A P G | Q G L E W M G | R I N P D |
| a54 | L T E . . . . . L | S M H W V R Q | A P G | E G L E W M G | G F . . D |
| k II 86A | I K D . . . . . Y | Y M H W V K Q | R P E | Q G L E W I G | W I D P . |
| k I 65 | F T S . . . . . H | D I T W V R Q | P T G | Q G L E W M G | W L S P . |
| k II 42 | L A E . . . . . L | S M H W V R Q | A P G | K G P E W M G | G F D A . |
| k I 37 | F S S . . . . . Y | W I E W V K Q | R P G | H G L E W I G | E I L P . |
| k II 205 | I K D . . . . . Y | Y M H W V K Q | R P E | Q G L E W I G | W I D P . |
| k IV 25 | F T T . . . . . Y | G I S W V R Q | A P G | Q G L E W M G | W I . . S |
| k I 54 | F T D . . . . . Y | Y M H W V R Q | A P G | Q G P E W M G | W I N P . |
| k II 19 | L K E . . . . . L | S V H W V R Q | T P G | K G L E W M G | G F D P . |
| k II 87 | F S S . . . . . S | Y I H W L R Q | A R G | Q G L E W M G | M I D P . |
| k II 20 | L T D . . . . . L | S V H W L R Q | T P G | K G L E W M G | G F A L . |
| k II 136 | L T D . . . . . L | S M H W V R Q | V P G | K G L E W M G | G Y D P . |
| VH4 | | | | | |
| a72 | I S S G G . . . Y | Y W N W I R Q | H P V | K G L E W I G | C I . . . |
| a17 | M T S G S . . . S | Y W G W V R Q | P P A | K G L E W I G | T I . . . |
| a48 | I S S G . . . . Y | F W G W V R Q | P P G | K G L Q W V A | S I F H T |

FIG. 12 (continued): Alignment of selected VH domain sequences

| AHo | 62-92 |
|---|---|
| VH3 | |
| a02 | . . . G T I L H Y A D S V K G R F T I S R D N A E N T L H L Q |
| *a44* | . . G G S T Y Y A D S V K G R F T I S R D N S K N T L Y L Q |
| a25 | T D . G G A T D F A A P V R G R F T I S R D D S K N T F Y L E |
| a68 | A Y   D E T T E Y A P S V R G R F T I S R D S S K A S V Y L E |
| a28 | . S G S I G Y A D S V K G R F T I S R D N A K N S L Y L Q |
| a01 | . . G G T T Y Y A D S V K G R F T I S R D N S K N S L Y L Q |
| a41 | . . . G S N K Y Y A D S V K G R F T I S R D N S K N T L Y L Q |
| a09 | . . . A G D T H Y A D S V K G R F T I S R D N F K N T V Y L E |
| a04 | T E . G G T T D Y A A P V K G R F I I S R D D S K N T L Y L Q |
| *a43* | . . G G S T Y Y A D S V K G R F T I S R D N S K N T L Y L Q |
| a08 | T D . A G T R D Y S A P V K G R F I I S R D D S K N T V Y L E |
| a15 | . . G G S T Y Y A D S V K G R F T I S R D N S K S T L Y L Q |
| a22 | T D . G G T T D Y A A P V K G R F T I S R D N S K N T L Y L Q |
| a47 | V D . N Y A T D Y A E S V R G R F T F S R D D S K N T A Y L Q |
| k IV 107 | . . S S Y I Y Y A D S V K G R F T I S R D N A K N S L Y L A |
| a fw1 | . . S G S I V Y A D S V K G R M T I S R D N A K N S L Y L E |
| a fw5 | . G G T T Y Y V D S V K G R F T I S R D N S K N T L Y L Q |
| *a fw10* | . G R I E H Y A D A V R G R F T I S R D N S Q N T V F L Q |
| a fw8 | V Y   G G T T E Y A A S V R G R F T I S R D D S N S V A Y L Q |
| k III 25 | . . G N F Q Q Y V D S V K G R F T I S R D N A K N S L Y L Q |
| k I 12 | . . G G T T D Y A A P L K D R I T I S R D D S K N T V Y L Q |
| a61 | . . G S N K N Y G D S V K G R F T I S R D N S K N T L Y L Q |
| k IV 103 | . . S G S I G Y A D S V K G R F T I S R D N A K N S L Y L Q |
| a18 | . . S G S I A Y A D S V K G R F T I S R N N A K N S L Y L Q |
| a69 | . . S G T I G Y A D S V K G R F T I S R D N A K N T V Y L Q |
| a65 | . . T D D T Y Y A D S V K G R F T I S R D L S K N T L Y L Q |
| a59 | S . G N T I Y Y A D S V K G R F T I S R D N A K N S L Y L Q |
| a58 | D . G R T . Y F A D S V K G R F S V S R D N S K N T V Y L Q |
| a51 | T E   G G T T E Y A A P V K G R F T I S R D D S K D T L Y L Q |
| k IV 98 | . . G D S S Y Y A D S V K G R F T I S R D N S K . . . . . |
| k III 10 | S D   G G T T D Y A A P L K D R I T I S R D D S K N T L Y L Q |
| k III 8 | T D . G G T T D Y A A P L K D R I T I S R D D S K N T L Y L Q |
| a53 | . . . G S N K Q Y A D S V K G R F T I S R D N S K N T V H L Q |
| a49 | A Y . G G T T E Y A A S V K G R F T I S R D D S K S I A Y L Q |
| a24 | . . G S G K Y Y G R S V R G R F T I S R D N A N D S L F L Q |
| k II 114 | . . A G S T Y Y A D S V K G R F T I S R D D S K N T L H L Q |
| k III 23 | . . . G T E R R Y V D S V T G R F T I S R D N A K N S L Y L Q |
| a46 | . . . G G Y T H Y A D S V R G R F T I S R D N A K N S L S L Q |

FIG. 12 (continued): Alignment of selected VH domain sequences

| AHo | 62 63 64 65 66 67 68 69 70 71 72 73 74 75 76 77 | 78 79 80 81 82 | 83 84 85 86 87 88 | 89 90 91 92 |
|---|---|---|---|---|
| VH3 | | | | |
| a10 | . . . G R C T K Y A D A V K G R F | T I S R D | N A K N S V | Y L Q |
| k II 129 | . . . S D T V A Y G D S V K G R F | T I S R D | N G K K S L | Y L Q |
| k IV 135 | . . . S D K I G Y A D S V K G R F | T I S R D | N A K N A L | Y L Q |
| a60 | . . . G S D K Y Y A D S V K G R F | T I S R D | N S N K R L | Y L Q |
| k I 32 | . . . G T N E Y Y A D S V K G R F | T I S R D | N S K D T L | Y L H |
| k II 190 | . . . G G G I Y Y E D S V K G R F | T I S R D | I S K N T L | Y L Q |
| k I 22 | . . . G S S I Y Y A D S V Q G R F | T I S R D | N A E N S V | Y L Q |
| k I 33 | . . . G S S T Y Y A D S V K S R F | T M S R D | N S K N T L | S L Q |
| k I 13 | . . . G S F I Y Y T D S V K G R F | T I S R D | N A K N S L | F L Q |
| k I 61 | . . . G G S T H Y A D S V K G R F | T I S R D | N S K N T L | Y L Q |
| k III 18 | . . . G S I K H Y A D S V K G R F | T I S R D | D A K R S V | Y L Q |
| k III 20 | . . . D G V T L Y S D S V R G R F | T L S R D | N A N N S L | Y L Q |
| k II 10 | . . . N D N I G Y A D S V K G R F | T I S R D | N A K N S L | Y L Q |
| k II 84A | . . . S G N I A Y V D S V K G R F | T V S R D | N A E N S L | Y L Q |
| k I 19 | . . . S G N I G Y A D S V K G R F | T I S R D | S A K N S L | Y L Q |
| k I 17 | . . . N N D I G Y A D S V K G R F | T I S R D | N A K N S L | Y L H |
| k III 22 | . . . G S E T N S L D S V D G R F | T I S R D | N A R N S V | F L Q |
| k I 24 | . . . G T N E Y F A D S M R G R S | T I S R D | N F K N T L | S L E |
| k II 29 | . . . G T N E Y F A D S M R G R S | T I S R D | N F K N T L | S L E |
| k I 9 | . . . G T Y Q D Y A D S V K G R F | T I S R D | N S K T T V | D L Q |
| VH1a | | | | |
| a71 | . . . F G T T D Y A Q K F Q G R V | T I T A D | E T T N T A | Y M E |
| a62 | P M . F G T A N Y A P K F Q G R V | T I T A D | E S T S T A | S M D |
| k I 27 | . . I L G T T N Y A Q K F Q D R V | T I T A D | I S R S T A | Y M E |
| a34 | P I . L D I A N Y A Q K F Q G R V | T I T A D | K S T S T A | H M E |
| a45 | P M . F G T P N Y A Q K F Q G R V | T I T A D | E S T N T A | Y M E |
| k II 9a | . . M Y D T E D Y A Q K F R D R V | T I I A D | E S T T T T | Y M E |
| k IV 78 | . . . I G T P N H A Q K F Q G R V | T I T A D | E F T S T A | Y M E |
| k I 47 | . . I F G T P N N A Q T F Q D R L | T I S A D | Q A T H T A | Y M E |
| k I 64 | . . V L G T S S L A Q K F Q G R V | T L S A D | D S T S T A | Y M D |
| k II 124 | . . M F G T P N Y A Q K F Q G R F | T I T A D | E S T S T V | D M E |
| k III 11 | . . I F G T I N H V E R F R D R V | T F T A D | T S T S I A | Y M E |
| k I 34 | . . G D S D A K Y S P S F Q G H V | T I S V D | K S L T T A | F L Q |

FIG. 12 (continued): Alignment of selected VH domain sequences

| AHo | 62 63 64 65 66 67 68 69 70 71 72 73 74 75 76 77 78 79 80 81 82 83 84 85 86 87 88 89 90 91 92 |
|---|---|
| VH1b | |
| a21 | . . . S G A T N S A E S F K G R V S L T R D T S L N T A Y M E |
| * a33 * | . . . S G D T I Y A Q K F Q D R V T L T R D T S I G T V Y M E |
| a54 | P E . D G E P V Y A E K F E G R L T M I E D T S T D T A Y M E |
| k II 86A | . . E N G D T E Y A P K F K G K A T M T A D T S S N T A Y L Q |
| k I 65 | . . N T G D T G F A Q K F Q G R V T L T R N T S T S T A S L E |
| k II 42 | . . E D G E T I Y A Q K F Q G R I T M T E D T S T D T A Y M E |
| k I 37 | . . G S G S T N Y N E K F K G K A T F T A D T S S N T A Y M Q |
| k II 205 | . . E N G D T E Y A P K F K G K A T M T A D T S S N T A Y L Q |
| k IV 25 | G R . N G N T N Y A Q R L Q G R I T M T T D T S T S T A Y M E |
| k I 54 | . . R T G S T N S A Q T F Q G R V T M T M D T S I N T A Y M E |
| k II 19 | . . E D G D T I H P H Q F Q G R V T T T E D S S I D T A Y M E |
| k II 87 | . . S G E R A D Y A Q M L E G R L T V T R D A S T S T I Y L D |
| k II 20 | . . E E G E K I S A Q R F Q G R V T M T E D T S T D T A Y L H |
| k II 136 | . . E D G E T V Y A R E F Q G R V T M T E D T S T D T A Y M E |
| VH4 | |
| a72 | Y K . S G S T I Y N P S L T S R L T I S V D T S K T Q V S L N |
| a17 | Y Y . S G N T Y Y N P S L K S R V T I S V D P S K N Q F S L K |
| a48 | . . . . . G S N Y Y N P S L R S R L S I S V D R T K N Q F S L R |

FIG. 12 (continued): Alignment of selected VH domain sequences

| AHo | 93 94 95 96 97 98 99 100 101 102 103 104 105 106 107 108 109 110 111 112 113 114 115 116 117 118 119 120 121 122 123 |
|---|---|
| VH3 | |
| a02 | M N S L R A E D T A V Y Y C A R D T G G . . . . . . . . . . . |
| * a44 * | M N S L R A E D T A V Y Y C A A H V L R F L E W . . . . . . . |
| a25 | M N S L R P E D T A V Y Y C A T D L E . . . . . . . . . . . . |
| a68 | M N S L E S E D T A M Y Y C T R D V E R F D . . . . . . . . . |
| a28 | M N S L R A E D T A L Y Y C V K G G Y C S G G G . . . . . . . |
| a01 | M N S L R A E D T A L Y Y C A K R P R T N V F G P . . . . . . |
| a41 | M N S L R A E D T A V Y Y C A R D M N Y Y D . . . . . . . . . |
| a09 | M N T L R A K D T G L Y Y C A R D T G P G M A . . . . . . . . |
| a04 | M N S L K T E D T A V Y Y C A K E R G S S S W F D Q . . . . . |
| * a43 * | M N S L R A E D T A V Y Y C A K D A G I A V . . . . . . . . . |
| a08 | M N S L K T E D T A I Y Y C T T G D T R R L E N Y F . . . . . |
| a15 | M D S L R A G D T A V Y Y C A R D R T F L P H D R S G . . . . |
| a22 | M N S L R A E D T A V Y Y C A R G T H Y Y D S S G Y Y . . . . |
| a47 | M T S L K I D D T A V Y Y C T C R P G P . . . . . . . . . . . |
| k IV 107 | N . . . . . . . . . . . . . . . . . . . . . . . . . . . . . . |
| a fw1 | M N S L R P E D T A Q Y Y C A R D R D M W F . . . . . . . . . |
| a fw5 | M N S L R A E D T A V Y Y C A K D R G V D L P Y Y Y G S G . . |
| * a fw10 * | M N S L R S D D T A L Y Y C A R E I G . . . . . . . . . . . . |
| a fw8 | M D N L K T D D T A V Y Y C T R E G H L A H L E W . . . . . . |
| k III 25 | M S S L R G E D T A L Y H C V I N P . . . . . . . . . . . . . |
| k I 12 | M N S L K T E D T G V Y Y C V T G I P R S . . . . . . . . . . |
| a61 | M N S L R A E D T A V Y Y C A Q A Y C G G D C H S . . . . . . |
| k IV 103 | M N S L R V E D T A F Y Y C V K D S G G . . . . . . . . . . . |
| a18 | M N S L R A E D T A L Y Y C A K S L S G S . . . . . . . . . . |
| a69 | M N F L R A E D T A V Y Y C A R D Y H G S G . . . . . . . . . |
| a65 | M N S L R A E D T A V Y Y C A R G G V G Q L . . . . . . . . . |
| a59 | M S S L R A E D T A V Y Y C V R D A Y T I . . . . . . . . . . |
| a58 | I N S L R A E D T A V Y Y C A M N D F W . . . . . . . . . . . |
| a51 | M N S L K T E D T A V Y Y C T T Q R W . . . . . . . . . . . . |
| k IV 98 | . . . . . . . . . . . . . . . . . . . . . . . . . . . . . . . |
| k III 10 | M N S L K T E D T G V Y Y C V T G I P R S . . . . . . . . . . |
| k III 8 | V N R L K T E D T G V Y Y C V T G I P R S . . . . . . . . . . |
| a53 | M N S L R A E D T A V Y Y C A T E G . . . . . . . . . . . . . |
| a49 | M N S L K T E D T A V Y Y C T R L G G S G L . . . . . . . . . |
| a24 | M N S L R A G D T A R Y Y C V R E R L . . . . . . . . . . . . |
| k II 114 | L N S L R A E D T A V Y Y C T S G G . . . . . . . . . . . . . |
| k III 23 | M D A L R A E D T A M Y Y C A N T P L . . . . . . . . . . . . |
| a46 | M N S L R G E D T A V Y Y C A R Y N Y C S G G T C . . . . . . |

FIG. 12 (continued): Alignment of selected VH domain sequences

| AHo | 93 94 95 96 97 98 99 100 101 | 102 103 104 105 106 107 108 | 109 110 111 112 113 114 115 116 117 118 119 120 121 122 123 |
|---|---|---|---|
| VH3 | | | |
| a10 | M N S L T A E D T | A V Y F C A R | T G S G . . . . . . . . . . . |
| k II 129 | M N S L I P E D T | A L Y Y C A K | D S A Y G S . . . . . . . . . . |
| k IV 135 | M D S L R V E D T | A L Y Y C A K | D Q I Y Y Y D T R G . . . . . |
| a60 | M N S L R V E D T | A L Y F C A K | E G . . . . . . . . . . . . . |
| k I 32 | M N S L R A E D T | A V Y Y C A R | E G F . . . . . . . . . . . . |
| k II 190 | M N S L R A E D T | A I Y Y C A K | R Y C S G . . . . . . . . . . |
| k I 22 | M N S L R A E D T | G V Y Y C A R | D Q Y G . . . . . . . . . . . |
| k I 33 | M N S L R A E D T | A I Y Y C A K | D R Y C S G G N . . . . . . . |
| k I 13 | M N S L R A E D T | A V Y F C V R | D K A Y S G Y . . . . . . . . |
| k I 61 | M N S L R A E D T | A I Y Y C T Y | L G G I P . . . . . . . . . . |
| k III 18 | M N S L R A D D T | A L Y Y C A K | G G L S G Y N Y G R . . . . . |
| k III 20 | M S N L R A D D T | A V Y Y C A R | E P L Y H R . . . . . . . . . |
| k II 10 | M N S L R A E D T | A F Y Y C V K | E A R R Y A G N . . . . . . . |
| k II 84A | M N S L R T D D T | A L Y Y C A R | Y P V H Y D F W S G N G Q Y . |
| k I 19 | M N S L R A E D T | A L Y Y C G K | D T V A G A . . . . . . . . . |
| k I 17 | M N S L R G E D T | G I Y F C V R | D I R P T . . . . . . . . . . |
| k III 22 | M N D L R A E D T | A V Y Y C A R | D S P A V P T . . . . . . . . |
| k I 24 | V H S L R P E D T | A L Y Y C V K | E D W . . . . . . . . . . . . |
| k II 29 | V H S L R P E D T | A L H Y C V K | E D W . . . . . . . . . . . . |
| k I 9 | M H S L R P E D T | A V Y Y C A R | E D F . . . . . . . . . . . . |
| VH1a | | | |
| a71 | L S T L R T E D T | A V Y Y C A R | D G S G G E T . . . . . . . . |
| a62 | L S S L R F E D T | A V Y Y C N L | Y N D V L T D F E K S H Y Y G |
| k I 27 | L T S L R S E D T | A I Y Y C A R | A H D S G W G H . . . . . . . |
| a34 | L R S L R S E D T | A L Y Y C A R | D V R A A V G S G Y Y Y G . . |
| a45 | L S S L R S E D T | A V Y Y C S R | A G S Y G S G N Y Y V R E H F |
| k II 9a | L S S L R F E D T | A V Y Y C A T | A P P H Y D V L S A W G Y G . |
| k IV 78 | L N S L K S E D T | A V Y Y C A R | D E G S D A G . . . . . . . . |
| k I 47 | L I N L T P D D T | A V Y Y C A R | G F R H T V E L N W . . . . . |
| k I 64 | L S S L A S D D T | A V Y Y C A T | V G D G Y V P . . . . . . . . |
| k II 124 | L T S L R S E D T | A V Y Y C A T | G I G G V G . . . . . . . . . |
| k III 11 | M S G L T S D D T | A V Y Y C A R | D E I A A A G . . . . . . . . |
| k I 34 | W S G L R A S D T | A I Y Y C A R | T T P G Y S G F D G G . . . . |

FIG. 12 (continued): Alignment of selected VH domain sequences

| AHo | 93 94 95 96 97 98 99 100 101 102 103 104 105 106 107 108 109 110 111 112 113 114 115 116 117 118 119 120 121 122 123 |
|---|---|
| VH1b | |
| a21 | L T R L S N D D T A V Y Y C A X G S A D S L Y D A . . . . . . . |
| *a33* | L T S L T S D D T A V Y Y C A R V P R G T Y L D P W D Y . . . |
| a54 | L S G L R S E D T A I Y Y C A A A Y F G S G S Y Y P N W . . . |
| k II 86A | L S S L T S E D T A V Y Y C N A L T T A Y A . . . . . . . . . |
| k I 65 | L S D L N S D D T A V Y Y C A R D A N P N C N S V S C S K G D |
| k II 42 | L R S L R S D D T A V Y Y C A T E V F Y G S G T V R D Y G . . |
| k I 37 | L S S L T S E D S A V Y Y C A R G Y Y R Y D . . . . . . . . . |
| k II 205 | L S S L T S E D T A V Y Y C N A L T T A Y A . . . . . . . . . |
| k IV 25 | L R S L R P D D T A V Y Y C A R D E H D S S G Y A . . . . . . . |
| k I 54 | L S R L T S D D T A V Y Y C A R D W S G Y D P T Y Y . . . . . |
| k II 19 | L S S L R S E D T A M Y Y C A T N L N E N Y A E N S R . . . . |
| k II 87 | L S S L R S E D T A R Y Y C A R G Q E G V V G T A N H V P Y . |
| k II 20 | L S S L T S E D T A V Y Y C A S G D D G Y D I E A . . . . . . |
| k II 136 | L S S L R S E D T A V Y Y C S S G M L Q M G G A . . . . . . . |
| VH4 | |
| a72 | L R S V T A A D T A V Y Y C A R G S D A Y G . . . . . . . . |
| a17 | L T S L T A T D T A M Y Y C A R E A D D Y D E H G D F S Y |
| a48 | L S S V T A A D T A L Y Y C A N S G V P T Y K Y Y . . . |

FIG. 12 (continued): Alignment of selected VH domain sequences

| AHo | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|---|---|---|---|---|---|---|
| VH3 | | | | | | | | | | | | | | | | | | | | | | | | | | |
| a02 | . | . | . | . | . | . | . | . | S | S | R | A | F | D | I | W | G | Q | G | T | M | V | T | V | S | S |
| *a44* | . | . | . | . | . | . | . | . | L | P | D | A | F | D | I | W | G | Q | G | T | L | V | T | V | S | S |
| a25 | . | . | . | . | . | . | . | . | S | F | G | A | F | D | I | W | G | Q | G | T | M | V | T | V | S | S |
| a68 | . | . | . | . | . | . | . | . | T | S | G | Y | Y | E | A | W | G | Q | G | T | L | V | T | V | S | S |
| a28 | . | . | . | . | . | . | . | . | C | S | D | A | F | D | I | W | G | Q | G | T | T | V | T | V | S | S |
| a01 | . | . | . | . | . | . | . | . | G | L | N | Y | F | D | L | W | G | Q | G | T | L | V | T | V | S | S |
| a41 | . | . | . | . | . | . | . | . | V | S | G | N | C | D | C | W | G | Q | G | T | L | V | T | V | S | S |
| a09 | . | . | . | . | . | . | . | . | V | V | G | I | P | L | D | W | G | Q | G | T | L | V | T | V | S | S |
| a04 | . | . | . | . | . | . | . | . | N | P | Y | C | F | D | S | W | G | Q | G | T | L | V | T | V | S | S |
| *a43* | . | . | . | . | . | . | . | . | A | G | T | C | F | D | Y | W | G | Q | G | T | L | V | T | V | S | S |
| a08 | . | . | . | . | . | . | . | . | G | W | G | P | S | D | Y | W | G | Q | G | T | L | V | T | V | S | S |
| a15 | . | . | . | . | . | . | . | . | Y | Y | A | Y | . | . | . | W | G | Q | G | T | L | V | T | V | S | S |
| a22 | . | . | . | . | . | . | . | . | K | H | D | A | F | D | I | W | G | Q | G | T | T | V | T | V | S | S |
| a47 | . | . | . | . | . | . | . | . | G | N | K | F | I | D | Y | W | G | Q | G | T | L | V | T | V | S | S |
| k IV 107 | . | . | . | . | . | . | . | . | . | . | . | . | . | . | . | . | . | . | . | . | . | . | . | . | . | . |
| a fw1 | . | . | . | . | . | . | . | . | W | G | N | G | L | D | V | W | G | Q | G | T | L | V | T | V | S | S |
| a fw5 | . | . | . | . | . | . | . | . | S | Y | Y | N | V | P | S | W | G | Q | G | T | L | V | T | V | S | S |
| *a fw10* | . | . | . | . | . | . | . | . | A | T | G | Y | L | D | N | W | G | Q | G | T | L | V | T | V | S | S |
| a fw8 | . | . | . | . | . | . | . | . | F | P | G | D | F | D | Y | W | G | Q | G | T | L | V | T | V | S | S |
| k III 25 | . | . | . | . | . | . | . | . | S | V | G | V | P | D | L | W | G | Q | G | T | L | V | T | V | S | S |
| k I 12 | . | . | . | . | . | . | . | . | Y | G | S | Y | Y | D | Y | W | G | Q | G | T | L | V | T | V | S | S |
| a61 | . | . | . | . | . | . | . | . | G | A | E | Y | F | P | H | W | G | Q | G | T | L | V | T | V | S | S |
| k IV 103 | . | . | . | . | . | . | . | . | G | V | G | L | F | D | Y | W | G | Q | G | T | L | V | T | V | S | S |
| a18 | . | . | . | . | . | . | . | . | Y | Y | S | P | F | D | Y | W | G | Q | G | T | L | V | T | V | S | S |
| a69 | . | . | . | . | . | . | . | . | R | T | H | T | F | D | I | W | G | Q | G | T | M | V | T | V | S | S |
| a65 | . | . | . | . | . | . | . | . | W | L | S | G | F | D | H | W | G | Q | G | T | L | V | T | V | S | S |
| a59 | . | . | . | . | . | . | . | . | S | W | Y | E | F | D | W | W | G | Q | G | T | L | V | T | V | S | S |
| a58 | . | . | . | . | . | . | . | . | S | G | H | P | G | D | Y | W | G | Q | G | T | L | V | T | V | S | S |
| a51 | . | . | . | . | . | . | . | . | F | Q | S | G | E | D | Y | W | G | Q | G | T | L | V | T | V | S | S |
| k IV 98 | . | . | . | . | . | . | . | . | . | . | . | . | . | . | . | . | . | . | . | . | . | . | . | . | . | . |
| k III 10 | . | . | . | . | . | . | . | . | Y | G | S | Y | Y | D | Y | W | G | Q | G | T | L | V | T | V | S | S |
| k III 8 | . | . | . | . | . | . | . | . | Y | G | S | Y | Y | D | Y | W | G | Q | G | T | L | V | T | V | S | S |
| a53 | . | . | . | . | . | . | . | . | S | Y | Y | G | M | D | V | W | G | Q | G | T | T | V | T | V | S | S |
| a49 | . | . | . | . | . | . | . | . | S | I | N | Y | F | D | Y | W | G | Q | G | T | L | V | T | V | S | S |
| a24 | . | . | . | . | . | . | . | . | N | D | D | A | F | D | T | W | G | Q | G | T | M | V | T | V | S | S |
| k II 114 | . | . | . | . | . | . | . | . | D | R | A | D | F | D | Y | W | G | Q | G | T | L | V | T | V | S | S |
| k III 23 | . | . | . | . | . | . | . | . | R | S | D | P | F | D | V | W | G | Q | G | T | T | V | T | V | S | S |
| a46 | . | . | . | . | . | . | . | . | Y | P | H | G | M | D | V | W | G | Q | G | T | T | V | T | V | S | S |

FIG. 12 (continued): Alignment of selected VH domain sequences

| AHo | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|---|---|---|---|---|---|---|
| VH3 | | | | | | | | | | | | | | | | | | | | | | | | | | |
| a10 | . | . | . | . | . | . | . | . | S | Y | S | H | L | S | H | W | G | Q | G | T | L | V | T | V | S | S |
| k II 129 | . | . | . | . | . | . | . | . | G | K | G | G | F | D | I | W | G | Q | G | T | T | V | T | V | S | S |
| k IV 135 | . | . | . | . | . | . | . | . | H | W | G | A | L | D | M | W | G | Q | G | T | T | V | T | V | S | S |
| a60 | . | . | . | . | . | . | . | . | G | H | Y | Y | F | D | Y | W | G | Q | G | T | L | V | T | V | S | S |
| k I 32 | . | . | . | . | . | . | . | . | G | G | I | L | G | D | V | W | G | Q | G | T | L | V | T | V | S | S |
| k II 190 | . | . | . | . | . | . | . | . | G | R | C | Y | F | D | Y | W | G | Q | G | T | L | V | T | V | S | S |
| k I 22 | . | . | . | . | . | . | . | . | F | S | Y | G | M | D | V | W | G | Q | G | T | T | V | T | V | S | S |
| k I 33 | . | . | . | . | . | . | . | . | C | F | G | S | L | D | Y | W | G | Q | G | T | L | V | T | V | S | S |
| k I 13 | . | . | . | . | . | . | . | . | D | P | S | Y | F | D | S | W | G | Q | G | T | L | V | T | V | S | S |
| k I 61 | . | . | . | . | . | . | . | . | D | R | R | P | F | D | H | W | G | Q | G | T | L | V | T | V | S | S |
| k III 18 | . | . | . | . | . | . | . | . | L | A | D | A | F | D | F | W | G | Q | G | T | M | V | T | V | S | S |
| k III 20 | . | . | . | . | . | . | . | . | P | E | D | A | F | D | I | W | G | Q | G | T | M | V | T | V | S | S |
| k II 10 | . | . | . | . | . | . | . | . | S | P | Y | G | M | D | V | W | G | Q | G | T | L | V | T | V | S | S |
| k II 84A | . | . | . | . | . | . | . | . | N | Y | Y | G | M | D | V | W | G | Q | G | T | T | V | T | V | S | S |
| k I 19 | . | . | . | . | . | . | . | . | V | F | D | G | L | D | I | W | G | Q | G | T | T | V | T | V | S | S |
| k I 17 | . | . | . | . | . | . | . | . | R | Y | Y | G | M | D | V | W | G | R | G | T | T | V | T | V | S | S |
| k III 22 | . | . | . | . | . | . | . | . | T | A | W | Y | F | D | V | W | G | R | G | T | L | V | T | V | S | S |
| k I 24 | . | . | . | . | . | . | . | . | G | L | G | A | F | D | I | W | G | Q | G | T | L | V | T | V | S | S |
| k II 29 | . | . | . | . | . | . | . | . | G | L | G | A | F | D | I | W | G | Q | G | T | M | V | T | I | S | S |
| k I 9 | . | . | . | . | . | . | . | . | D | P | P | R | L | D | N | W | G | R | G | T | T | V | T | V | S | S |
| VH1a | | | | | | | | | | | | | | | | | | | | | | | | | | |
| a71 | . | . | . | . | . | . | . | . | . | . | . | . | F | D | S | W | G | Q | G | T | L | V | T | V | S | S |
| a62 | . | . | . | . | . | . | . | . | . | . | . | . | . | M | D | V | W | G | Q | G | T | T | V | T | V | S | S |
| k I 27 | . | . | . | . | . | . | . | . | . | . | . | . | F | D | L | W | G | P | G | T | L | V | T | V | S | S |
| a34 | . | . | . | . | . | . | . | . | . | . | . | . | . | M | D | V | W | G | Q | G | T | L | V | T | V | S | S |
| a45 | Y | Y | G | . | . | . | . | . | . | . | . | . | . | M | D | V | W | G | Q | G | T | T | V | T | V | S | S |
| k II 9a | . | . | . | . | . | . | . | . | . | . | . | . | . | M | D | V | W | G | Q | G | T | T | V | T | V | S | S |
| k IV 78 | . | . | . | . | . | . | . | . | . | . | . | . | . | M | D | V | W | G | P | G | T | T | V | T | V | S | S |
| k I 47 | . | . | . | . | . | . | . | . | . | . | . | . | F | D | L | W | G | Q | G | T | L | V | T | V | S | S |
| k I 64 | . | . | . | . | . | . | . | . | . | . | . | . | . | R | D | Y | W | G | Q | G | T | L | V | T | V | S | S |
| k II 124 | . | . | . | . | . | . | . | . | . | . | . | . | . | M | D | V | W | G | Q | G | T | L | V | T | V | S | S |
| k III 11 | . | . | . | . | . | . | . | . | . | . | . | . | . | . | I | D | Y | W | G | Q | G | T | L | V | T | V | S | S |
| k I 34 | . | . | . | . | . | . | . | . | . | . | . | . | . | D | D | Y | W | G | Q | G | T | L | V | T | V | S | S |

FIG. 12 (continued): Alignment of selected VH domain sequences

| AHo | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|---|---|---|---|---|---|---|
| VH1b | | | | | | | | | | | | | | | | | | | | | | | | | | |
| a21 | . | . | . | . | . | . | . | . | . | . | . | . | . | F | D | I | W | G | Q | G | T | T | V | T | V | S S |
| *a33* | . | . | . | . | . | . | . | . | . | . | . | . | . | F | D | Y | W | G | Q | G | T | L | V | T | V | S S |
| a54 | . | . | . | . | . | . | . | . | . | . | . | . | . | F | D | P | W | G | Q | G | T | L | V | T | V | S S |
| k II 86A | . | . | . | . | . | . | . | . | . | . | . | . | . | M | D | S | W | G | Q | G | T | L | V | T | V | S S |
| k I 65 | Y | T | G | . | . | . | . | . | . | . | . | . | . | I | D | V | W | G | Q | G | T | T | V | T | V | S S |
| k II 42 | . | . | . | . | . | . | . | . | . | . | . | . | . | M | D | V | W | G | Q | G | T | M | V | T | V | S S |
| k I 37 | . | . | . | . | . | . | . | . | . | . | . | . | . | M | D | Y | W | G | Q | G | T | L | V | T | V | S S |
| k II 205 | . | . | . | . | . | . | . | . | . | . | . | . | . | M | D | Y | W | G | Q | G | T | L | V | T | V | S S |
| k IV 25 | . | . | . | . | . | . | . | . | . | . | . | . | . | L | E | Y | W | G | Q | G | T | L | V | T | V | S S |
| k I 54 | . | . | . | . | . | . | . | . | . | . | . | . | . | F | D | S | W | G | T | G | T | L | V | T | V | S S |
| k II 19 | . | . | . | . | . | . | . | . | . | . | . | . | . | F | D | Q | W | G | Q | G | T | L | V | T | V | S S |
| k II 87 | . | . | . | . | . | . | . | . | . | . | . | . | . | F | D | Y | W | G | Q | G | T | L | V | T | V | S S |
| k II 20 | . | . | . | . | . | . | . | . | . | . | . | . | . | F | D | Y | W | G | Q | G | T | L | V | T | V | S S |
| k II 136 | . | . | . | . | . | . | . | . | . | . | . | . | . | S | D | V | W | G | Q | G | T | L | V | T | V | S S |
| VH4 | | | | | | | | | | | | | | | | | | | | | | | | | | |
| a72 | . | . | . | | | | | . | . | . | . | . | . | L | D | V | W | G | Q | G | T | T | V | T | V | S S |
| a17 | | | | | | | | . | . | . | . | . | . | F | D | I | W | G | R | G | T | L | V | T | V | S S |
| a48 | . | . | . | | | | | . | . | . | . | . | . | F | E | Y | W | G | Q | G | T | L | V | T | V | S S |

FIG. 13 Alignment of selected VL domain sequences

| AHo | 1 2 3 4 5 6 7 8 9 10 11 12 13 14 15 16 17 18 19 20 21 22 23 24 25 26 27 28 29 30 31 |
|---|---|
| Vκ1 | |
| a72 | E I V L T Q S P S S L S A S V G D R V T I T C Q A S Q . . D I |
| a02 | E I V M T Q S P S F L S A S V G D R V T I A C R A S Q . . G I |
| a44 | E I V L T Q S P S S L S A S V G D R V T I T C R A S Q . . S I |
| a25 | E I V L T Q S P S S L S A S V G D K V T I T C R A S Q . . S L |
| a68 | E I V L T Q S P S S L S A S V G D R V T I T C R A S Q . . S I |
| a28 | E I V M T Q S P S S L S A S L G D R V T I T C Q A S Q . . D I |
| a09 | D I Q L T Q S P S S L S A S V G D R V T I T C Q A S H . . D I |
| a62 | D I Q L T Q S P S S L S A S V G D R V T I T C R A S Q . . S I |
| a54 | E I V L T Q S P S S L S T S V G D R V T I T C Q A S Q . . D I |
| k IV 40 | D I Q L T Q S P S S L S A S V G D R V T I A C R A S Q . . S I |
| a fw5 | . . . . . . . P S C L H L . V G D R V T I T C R A H V . . R A |
| a fw8 | E I V L T Q S P S S L S V T V G D R V T I T C Q A S Q . . D I |
| a fw 10 | E I V L T Q S P S S L S A S L G D R V T I T C R A S Q . . S I |
| k I 27 | E I V M T Q S P S T L S A S V G D R V I I T C R A S Q . . S I |
| k III 25 | E I V L T Q S P S S L S A S V G D R V T L T C R A S Q . . G I |
| a17 | E I V L T Q S P S T L S A S V G D R V T I T C R T S Q . . S I |
| a61 | D I Q I T Q S P S S V S A S V G D R V T I T C R A S Q . . G I |
| a18 | E I V L T Q S P S S L S A S V G D R V T I T C Q A S Q . . D I |
| a34 | . . . . . . . . . . . . . G D R V T L S C R A S Q . . T I |
| a45 | E I V L T Q S P S S L S A S V G D T V T I T C R A S E . . T I |
| a64 | E I V L T Q S P S S L S A S V G D R V T I T C R A S Q . . T I |
| k IV 98 | E I V L T Q S P S T L S A S V G D R V T I T C R A S Q . . S V |
| k II 86A | E I V M T Q S P S S L S A S V G D R V T I T C Q A S Q . . V I |
| a53 | D V V M T Q S P S S L S A S V G D R I T I T C Q A S Q . . V I |
| k II 42 | E I V L T Q S P S S L S A S V G D R V T I T C R A G Q . . S I |
| k II 114 | E I V L T Q S P S S L S A S I G D R V T I S C R A S Q . . N I |
| k II 205 | I E I V T Q S P S S L S A S V G D R V T I T C R A S Q . . D I |
| k I 65 | E I V L T Q S P S S L S A S V G D R V T I T C R A S Q . . N I |
| k I 37 | E I V L T Q S P S S L S A S V G D R V T I T C R A S Q . . G I |
| k III 23 | E I V L T Q S P S T L S A S V G D R V I L T C R A S Q . . S L |
| k IV 25 | D I Q L T Q S P S S L S A F V G D R V T I T C R A S Q . . N I |
| k I 54 | E I V L T Q S P S S L S A S V G D R V T I T C R A S R . . N I |
| k II 19 | E I V L T Q S P S S L S A S V G D R V T I T C Q A S Q . . D I |
| k I 32 | D I Q M T Q S P S S L S A S V G D R V T I S C R A S Q . . G I |
| k I 34 | E I V L T Q S P S S L S A S V G D R V T I T C R A S Q . . N I |
| k I 19 | E I V L T Q S P S S L S A S V G D R V T I T C Q A S Q . . D I |
| k I 50 | E I V M T Q S P S F L S A S V G D R V T I T C R A S Q . . G I |
| k III 22 | E I V L T Q S P S S F S A S T G D R V T I T C R A S Q . . G I |
| k I 64 | E I V L T Q S P S S L S A S V G D R V T I T C R A S Q . . G I |

FIG. 13 (continued): Alignment of selected VL domain sequences

| AHo | 1 2 3 4 5 6 7 | 8 9 10 11 12 13 14 15 16 17 18 19 | 20 21 22 23 24 | 25 26 27 28 29 30 31 |
|---|---|---|---|---|

Vκ1

| | |
|---|---|
| k II 29 | D I Q L T Q S P P S L S A S V G D K V T I T C R A S E . . S I |
| k I 13 | D V V M T Q S P S S L S T S V G D R V T I T C R A G Q . . S I |
| k I 9 | E I V L T Q S P S S L S A S V G D R V T I T C R A S R . S I |
| k I 24 | E I V M T Q S P S S F S A S V G D R V T I T C R A S Q . . N I |
| k II 124 | D I Q L T Q S P S T L S A S V G D R V T I T C R V S Q . N I |
| k II 10 | E I V M T Q S P S S L S A S V G D R V T I T C R A S Q . S I |

Vκ3

| | |
|---|---|
| a41 | E I V L T Q S P G T L S L S P G E R A X L S C R A S Q . . S V |
| a01 | E I V L T Q S P G I L Y L S P G E R A T L S C R A S Q . . S V |
| k IV 103 | E I V M T Q S P A T L S V S P G E S A A L S C R A S Q . . G V |
| k IV 135 | E I V L T Q S P A T L S L S P G E R A T L S C R A S Q . . T L |
| k II 190 | E T T L T Q S P G T L S L S P G E R A T L S C R A S Q . . S V |
| k II 136 | E I V L T Q S P A T L S L S P G E R A T L S C R A S Q . S V |

Vκ2

| | |
|---|---|
| k II 129 | E I V L T Q S P L S L P V T L G Q P A S I S C R S S Q S L L Y |

Vλ1

| | |
|---|---|
| a15 | Q A V L T Q P . S S A S G T P G Q R V T I S C S G S S . . S N |
| a22 | Q S V L T Q P . P S A S G T P G Q R V T I S C S G S R . . S N |
| a71 | Q A V V T Q E . P S V S A A P G Q K V T I S C S G S S . . S N |
| k IV 107 | Q S V L T Q P . P S V S A A P G Q K V T I S C S G S T . . S N |
| k I 12 | Q P V L T Q P . P S A S G T P G Q R V T I S C S G S S . . S N |
| a65 | L P V L T Q P . P S A S G T F G Q R V T I S C S G G S . . S N |
| a58 | Q P V L T Q P . P S A S G S P G Q S V T I S C T G T S . . S D |
| k III 8 | L P V L T Q P . P S V S G T P G Q R V T I S C S G S S . . S N |
| k III 10 | S Y E L T Q P . P S A S G T P G Q R V P I S C S G S G . . S N |
| a10 | L P V L T Q P . P S A S G T L G Q R V T I S C S G S S . . S N |
| k II 9a | E I V M T Q S . P S A S G T P G Q R V T I S C S G S S . . S N |
| k IV 78 | Q S V V T Q P . P S V S A A P G Q K V T I S C S G S S . . S N |
| k I 22 | Q S A L T Q P . P S V S G A P G Q R V T I S C T G S S . . S N |
| k II 20 | Q S V L T Q P . P S V S A A P G Q K V T I S C S G S S . . S N |
| k III 20 | Q S V V T Q P . P S A S G T P G Q R V T I S C S G A S . . S N |
| k I 17 | S Y V L T Q P . P S A S G T P G Q R V T I S C S G S D . . S N |

FIG. 13 (continued): Alignment of selected VL domain sequences

| AHo | 1 2 | 3 4 5 6 7 | 8 9 10 11 12 13 14 15 16 17 18 19 | 20 21 22 23 24 | 25 26 27 28 29 30 31 |
|---|---|---|---|---|---|

Vλ2

```
a47    Q S A L T Q P . A S V S G S P G Q S I T I S C T G T S . . . S D
a59    Q S A L T Q P . A S V S G S P G Q W I T I S C S G T G . . . S D
a51    Q S A L T Q P . R S V S G S P G Q S V T I S C T G T S . . . S D
a24    Q S A L T Q P . A S V S G S P G Q S I T I S C T G T S . . . S D
k II 87 Q S A L T Q P . R S V S G S P G Q S V T I S C T G T S . . . S D
k I 2  Q A V V T Q E . P S L T V S S G G T V T L T C S S S T . . . G P
```

Vλ3

```
a04    Q S V L T Q P . P S L S V A P G E T A R I N C G G N . . . . N
a33    L P V L T Q P . P S V S V A P G Q T A R I S C G G N . . . . N
a43    S Y V L T Q P . P S V S V A P G Q T A T V T C G G N . . . . N
a08    Q P V L T Q P . P S V S V S P G Q T V S I T C S G D . . . . G
a21    D I Q M T Q S . P S V S V S P G Q T A S I T C S G D . . . . K
a fw1  S S E L T Q D . P A V S V A L G Q T V R I T C H G D . . . . S
a69    Q S V L T Q P . P S V S V S P G Q T A T I T C S G D . . . . K
a49    Q P V L T Q P . P S V S V A P G Q T A R I T C G G S . . . . N
a48    Q P V L T Q P . P S V S V S P G Q T A R I T C S G D . . . . E
a46    Q S V L T Q P . P S V S V S P G Q T A S I T C S G D . . . . L
a60    Q T V V T Q E . P S F S V S P G G T V T L T C G L S . . . . S
```

FIG. 13 (continued): Alignment of selected VL domain sequences

| AHo | 32 33 34 35 36 37 38 39 40 | 41 42 43 44 45 46 47 | 48 49 50 | 51 52 53 54 55 56 57 | 58 59 60 61 62 63 |
|---|---|---|---|---|---|
| Vκ1 | | | | | |
| a72 | S N . . . . . . . | Y L N W Y Q Q | K P G | K A P N L L I | Y D . . . . . . |
| a02 | S N . . . . . . . | Y L A W Y Q Q | K S G | K A P K L L I | Y G . . . . . . |
| a44 | S D . . . . . . . | Y L N W Y Q K | K S Q | E A P K L L I | Y A . . . . . . |
| a25 | D T . . . . . . . | Y V N W Y Q Q | K L G | R A P K L L I | Y S . . . . . . |
| a68 | S S . . . . . . . | Y L N W Y Q Q | K P G | K A P K L L I | Y A . . . . . . |
| a28 | S N . . . . . . . | H L N W Y Q Q | R P G | K A P R L L I | F D . . . . . . |
| a09 | L N . . . . . . . | Y L N W Y Q Q | K P G | K A P K V L I | F D . . . . . . |
| a62 | S F . . . . . . . | Y L S W Y Q Q | K P G | K A P K L L I | Y A . . . . . . |
| a54 | S D . . . . . . . | Y L N W Y Q Q | K P G | K P P K L L I | Y D . . . . . . |
| k IV 40 | N T . . . . . . . | Y L N W Y Q Q | K P G | T A P K L L I | S A . . . . . . |
| a fw5 | L R S . . . . . . | Y L A W Y Q Q | K A G | K A P K L L I | Y A . . . . . . |
| a fw8 | S N . . . . . . . | H L N W Y Q Q | I P G | K A P K L L I | H A . . . . . . |
| a fw 10 | S S . . . . . . . | Y L N W Y Q Q | K P G | K A P K L L I | Y A . . . . . . |
| k I 27 | S S . . . . . . . | W L A W Y Q Q | K P G | K A P K L L I | Y K . . . . . . |
| k III 25 | R N . . . . . . . | E L A W Y Q Q | R P G | K A P K R L I | Y A . . . . . . |
| a17 | G R . . . . . . . | W L A W Y Q Q | K P G | K A P K V L I | Y T . . . . . . |
| a61 | S S . . . . . . . | Y L N W Y Q Q | K P G | E P P E L L I | Y D . . . . . . |
| a18 | S N . . . . . . . | N V N W Y Q Q | K P G | K A P N L L I | Y D . . . . . . |
| a34 | G T . . . . . . . | S L S W Y Q Q | K P G | Q A P K L L I | Y S . . . . . . |
| a45 | N N . . . . . . . | Y L N W Y Q Q | K P G | M A P A L L I | S G . . . . . . |
| a64 | G T . . . . . . . | N L N W Y Q Q | K S G | K A P K L L M | Y G . . . . . . |
| k IV 98 | S R . . . . . . . | W L A W Y Q Q | K P G | K A P R X L I | Y Q . . . . . . |
| k II 86A | S N . . . . . . . | H L N W Y Q Q | K P G | K A P K F L I | S D . . . . . . |
| a53 | S N . . . . . . . | Y L N W Y Q Q | K A G | K A P K L L I | Y G . . . . . . |
| k II 42 | S T . . . . . . . | Y L N W Y Q H | K P G | K A P K L L I | Y A . . . . . . |
| k II 114 | G N . . . . . . . | F L N W Y Q Q | K P G | K A P K L L I | Y T . . . . . . |
| k II 205 | R I . . . . . . . | D L D W Y Q Q | K P G | R A P K V L I | H E . . . . . . |
| k I 65 | N T . . . . . . . | Y L N W Y Q Q | K P G | K A P N L L I | Y A . . . . . . |
| k I 37 | A N . . . . . . . | Y L A W Y Q Q | K P G | K V P K L L I | Y S . . . . . . |
| k III 23 | H N . . . . . . . | Y L A W Y Q L | K P G | Q A P R L L M | S A . . . . . . |
| k IV 25 | I T . . . . . . . | F L N W Y Q Q | K P G | K A P K L L I | Y D . . . . . . |
| k I 54 | G S . . . . . . . | Y L N W Y Q Q | K S G | R A P R L L I | Y A . . . . . . |
| k II 19 | S H . . . . . . . | H L N W Y Q Q | R P G | K A P K L L I | Y G . . . . . . |
| k I 32 | R N . . . . . . . | D L S W Y Q Q | K P G | K A P K R L I | S A . . . . . . |
| k I 34 | R T . . . . . . . | Y L N W Y Q Q | K A G | T A P K L L I | S G . . . . . . |
| k I 19 | T N . . . . . . . | Y L N W Y Q H | K P G | K A P K L L I | F D . . . . . . |
| k I 50 | R S . . . . . . . | Y L A W Y Q Q | K P G | K A P K L L I | Y A . . . . . . |
| k III 22 | S S . . . . . . . | Y L A W Y Q Q | K P G | K A P K L L I | Y A . . . . . . |
| k I 64 | R N . . . . . . . | E L G W Y Q Q | K P G | K A P K L L I | Y A . . . . . . |

FIG. 13 (continued): Alignment of selected VL domain sequences

| AHo | 32 33 34 35 36 37 38 39 40 | 41 42 43 44 45 46 47 | 48 49 50 | 51 52 53 54 55 56 57 | 58 59 60 61 62 63 |
|---|---|---|---|---|---|
| Vκ1 | | | | | |
| k II 29 | N N . . . . . . | Y L N W Y Q Q | R P G | K A P K L L I Y G | . . . . . . |
| k I 13 | G I . . . . . . | F L N W Y Q Q | R P G | K A P K V L I Y A | . . . . . . |
| k I 9 | D N . . . . . . | H L N W Y R Q | R P G | K A P N L L I Y A | . . . . . . |
| k I 24 | I K . . . . . . | F L N W Y Q Q | K P G | K A P K L L I Y A | . . . . . . |
| k II 124 | F D . . . . . . | W V A W H Q Q | K P G | K A P K L L I Y R | . . . . . . |
| k II 10 | S G . . . . . . | F L N W Y Q Q | R P G | R A P K V L I Y A | . . . . . . |
| Vκ3 | | | | | |
| a41 | T S . . . . . | S S L A W Y Q Q | K P G | Q A P R L L I Y G | . . . . . . |
| a01 | S N . . . . . . | Y F A W Y Q Q | R P G | Q A P R L L I Y G | . . . . . . |
| k IV 103 | S T . . . . . . | N V A W Y Q Q | K P G | Q A P R L L I Y G | . . . . . . |
| k IV 135 | T H . . . . . . | Y L A W Y Q Q | K P G | Q A P R L L I Y D | . . . . . . |
| k II 190 | S G . . . . . | S Y L A W Y Q Q | K P G | Q A P R L L I Y G | . . . . . . |
| k II 136 | S N . . . . . . | Y L S W Y Q Q | K P G | Q A P R L L M Y D | . . . . . . |
| Vκ2 | | | | | |
| k II 129 | I D G N . . . | T Y L N W F H Q | R P G | Q S P R R L I Y K | . . . . . . |
| Vλ1 | | | | | |
| a15 | I G . . . . | S N Y V Y W Y Q Q | L P G | T A P K L L I Y S | . . . . . . |
| a22 | L G . . . . | S N T V T W Y Q H | V P G | T A P K L L I Y T | . . . . . . |
| a71 | I G . . . . | N N Y V S W Y Q Q | L P G | T A P K L L I Y D | . . . . . . |
| k IV 107 | I G . . . . | D N Y V S W Y Q Q | L P G | T A P Q L L I Y D | . . . . . . |
| k I 12 | I G . . . . | S N Y V Y W Y Q Q | L P G | T A P K L L I Y R | . . . . . . |
| a65 | I G . . . . | T N P V N W Y Q Q | L P G | T A P S L L I Y T | . . . . . . |
| a58 | I G H . . . | Y N Y V C W Y Q Q | H P G | K A P K V L I Y D | . . . . . . |
| k III 8 | I G . . . . | T N Y V Y W Y Q Q | L P G | T A P K L L I Y N | . . . . . . |
| k III 10 | I E . . . . | S H T V N W Y Q Q | L P G | T A P K L L I Y N | . . . . . . |
| a10 | I G . . . . | R N T V N W Y Q Q | L S G | T A P K L L I Y R | . . . . . . |
| k II 9a | I G . . . . | S N T V N W Y Q Q | F P G | T A P K L L I Y T | . . . . . . |
| k IV 78 | I G . . . . | S H Y V S W Y Q Q | L P G | T A P T L V I Y D | . . . . . . |
| k I 22 | I G G . . . | G Y D V H W Y Q H | L P G | T A P N L L I Y G | . . . . . . |
| k II 20 | I G . . . . | N N Y V S W Y Q Q | L P G | T A P K L L I Y D | . . . . . . |
| k III 20 | I G . . . . | N N Y V Y W Y R Q | L P G | M A P K L L I Y S | . . . . . . |
| k I 17 | I G . . . . | S H T V S W Y Q H | F P G | T A P P L L I Y T | . . . . . . |

FIG. 13 (continued): Alignment of selected VL domain sequences

| AHo | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 |
|---|---|---|---|---|---|---|---|---|---|---|---|---|---|---|---|---|---|---|---|---|---|---|---|---|---|---|---|---|---|---|---|---|
| Vλ2 | | | | | | | | | | | | | | | | | | | | | | | | | | | | | | | | |
| a47 | V | G | G | . | . | . | Y | D | Y | V | S | W | Y | Q | Q | H | P | G | K | A | P | K | L | M | I | Y | E | . | . | . | . | . |
| a59 | I | G | A | . | . | . | Y | N | Y | V | S | W | Y | Q | H | Y | P | G | K | A | P | K | L | M | I | Y | D | . | . | . | . | . |
| a51 | V | S | F | . | . | . | S | N | Y | V | S | W | Y | Q | Q | H | P | G | K | A | P | K | L | V | I | Y | A | . | . | . | . | . |
| a24 | V | G | G | . | . | . | Y | N | Y | V | S | W | Y | Q | Q | H | P | G | K | A | P | K | L | M | I | Y | D | . | . | . | . | . |
| k II 87 | V | G | G | . | . | . | Y | N | Y | V | S | W | Y | Q | Q | H | P | G | K | A | P | K | L | V | I | Y | D | . | . | . | . | . |
| k I 2 | V | T | S | . | . | . | A | F | Y | A | N | W | F | Q | Q | K | P | G | Q | A | P | R | A | L | I | Y | S | . | . | . | . | . |
| Vλ3 | | | | | | | | | | | | | | | | | | | | | | | | | | | | | | | | |
| a04 | I | G | . | . | . | . | D | K | S | V | H | W | Y | Q | Q | K | P | G | Q | A | P | V | L | V | M | Y | Y | . | . | . | . | . |
| a33 | I | E | . | . | . | . | T | I | S | V | H | W | Y | Q | Q | K | P | G | Q | A | P | V | L | V | V | S | D | . | . | . | . | . |
| a43 | I | G | . | . | . | . | S | K | S | V | H | W | Y | Q | Q | K | P | G | Q | A | P | V | L | V | V | Y | D | . | . | . | . | . |
| a08 | L | G | . | . | . | . | H | K | Y | V | S | W | Y | Q | Q | R | P | G | Q | S | P | I | L | V | I | C | Q | . | . | . | . | . |
| a21 | L | G | . | . | . | . | D | K | Y | A | C | W | Y | Q | Q | K | P | G | Q | S | P | V | L | V | I | Y | Q | . | . | . | . | . |
| a fw1 | L | R | . | . | . | . | Y | Y | S | A | S | W | Y | Q | Q | K | P | G | Q | A | P | L | L | V | M | Y | G | . | . | . | . | . |
| a69 | L | G | . | . | . | . | D | Q | Y | A | C | W | Y | Q | Q | K | P | G | Q | S | P | V | L | L | I | Y | E | . | . | . | . | . |
| a49 | I | G | . | . | . | . | S | R | N | V | H | W | Y | Q | Q | K | P | G | Q | A | P | V | L | V | V | Y | D | . | . | . | . | . |
| a48 | L | P | . | . | . | . | K | Q | Y | A | Y | W | Y | Q | Q | R | P | G | Q | A | P | V | L | I | I | Y | E | . | . | . | . | . |
| a46 | L | G | . | . | . | . | D | T | Y | A | Y | W | Y | Q | Q | R | P | G | Q | S | P | G | L | V | I | Y | E | . | . | . | . | . |
| a60 | G | S | V | S | T | . | S | Y | Y | P | S | W | Y | Q | Q | T | P | G | Q | A | P | R | T | L | V | H | S | . | . | . | . | . |

FIG. 13 (continued): Alignment of selected VL domain sequences

```
AHo       64 65 66 67 68 69 70 71 72 73 74 75 76 77 78 79 80 81 82 83 84 85 86 87 88 89 90 91 92 93 94 95
Vκ1
a72       . . . A S N L E I G V P S R F S G S G S G . . T D F T F T I S N
a02       . . . A S T L Q S G V P S R F S G S G S G . . T E F T L T I S S
a44       . . . A S T L Q S G V P S R F S G S G S G . . T D F T L T I S S
a25       . . . T S N L E S G V P S R F S G S G S G . . T D F T L T I S S
a68       . . . A S S L Q S G V P S R F T G S G S G . . T D F T L T I S S
a28       . . . A T E L E P G A P S R F S G S G S G . . T D F S F T I T N
a09       . . . A S D L Q K G V P S R F S G S G S G . . T H F T F T I S S
a62       . . . A S T L Q S G V P S R F S G S G Y G . . T D F T L T I S S
a54       . . . A T N L E T G V P P R F S G S G S G . . T H F T F T I T S
k IV 40   . . . A S V L Q S G V P S R F S G S G S G . . T D F T L T I R S
a fw5     . . . A S T L Q S G V P S R F S G S G S G . . T E F T L T I S S
a fw8     . . . A S S L Q S G V P S R F S G S G S G . . T D F T L T I S S
a fw 10   . . . A S S S Q S G V P S R F R G S E S G . . T D F T L T I S N
k I 27    . . . A S S L E S G V P S R F S G S G S G . . A E F T L T I S S
k III 25  . . . G S I L Q S G V P S R F S G S G S G . . T E F T L T I S S
a17       . . . V S K L Q S G V P S R F S G S G S G . . T E F T L T I G S
a61       . . . A S N L Q S G V P S R F S G S G S G . . T D F T L T I S S
a18       . . . A S N L A T G V P A R F S G G G S G . . T H F T F T I S S
a34       . . . A S H L Q N G V P S R F S G S G S G . . T D F T L A I S G
a45       . . . P F S F Q S G V P S R F R G S G F G . . T D F I L T I S D
a64       . . . A S I L Q S G V P S R F T G S G S G . . T D F T L T I S S
k IV 98   . . . A S S V E S G V P S R F S G S G S G . . T E F T L T I S S
k II 86A  . . . A S N L E T G V P S R F S G S G S G . . T D F T F T I S S
a53       . . . A S N L E T G V P S R F S G G G S G . . T E F T L T I S S
k II 42   . . . A S S L Q S G V P S R F S G S G S G . . T D F T L T I S S
k II 114  . . . A S T L Q S G V P S R F S G R G S G . . T E F T L T I S S
k II 205  . . . A S K L K S G A P S R F S G S G S G . . T Q F T L T I S S
k I 65    . . . A S N L Q S G V P S R F S G S G S G . . T D F T L T I S S
k I 37    . . . A S T L Q S G V P L R F S G S G S E . . T E F T L T I S S
k III 23  . . . A S H R A T G I P D R F S G S G S G . . T D F T L T V S R
k IV 25   . . . S S T L E S G V P S R F S G S G S G . . T D F T L T I S S
k I 54    . . . E S I L Q A G V P S R F S G S G S G . . T D F V L T I S G
k II 19   . . . A S N L Q T G V P L R F S G S G S G . . T D F T F T I S S
k I 32    . . . A S S L Q S G V P S R F S G S G S G . . T E F T L T I S S
k I 34    . . . A S S L Q S G V P S R F S G S G S G . . T D F T L T I N S
k I 19    . . . A S S L E R G V P S R F S G S G S G . . T D F T F T I N N
k I 50    . . . A S T L Q S G V P S R F S G S G S G . . T D F S L T I S S
k III 22  . . . A S T L Q S G V P S R F S G S G S G . . T D F T L T I S C
k I 64    . . . A S T L Q S G V P S R F S G S G S G . . T D F T L T I T S
```

FIG. 13 (continued): Alignment of selected VL domain sequences

```
AHo          64 65 66 67 68 69 70 71 72 73 74 75 76 77 78 79 80 81 82 83 84 85 86 87 88 89 90 91 92 93 94 95

Vκ1
k II 29      . . . A S N L Y S G V P S R F R G T A S G . . T D F T L T I N S
k I 13       . . . A S R L Q S G V P S R F S G S G S G . . T D F T L T I N S
k I 9        . . . A S N L E S G V P S R F S G S G S G . . T D F T L T I S S
k I 24       . . . A A N L Q G D V P S T F S G N G S G . . T D F T L T I S S
k II 124     . . . A S S L Q A G V P S R F S G S G Y G . . T E F T L T I T S
k II 10      . . . A S S L Q G G V P S R F S G S G S G . . T E F T L T I S S

Vκ3
a41          . . . A S T R A T G I P D R F S G S G S G . . T D F T L T I S R
a01          . . . A S S R A T G I P D R F S G S G S G . . T D F T L T I S R
k IV 103     . . . A T T R A S G V P A R F S G S G S G . . T E F T L T I N S
k IV 135     . . . T S K R A T G T P A R F S G S G S G . . T D F T L T I S S
k II 190     . . . A S S R A T G I P D R F S G S G S G . . T D F T L T I S R
k II 136     . . . V S N R A T G I P A R F S G S G S G . . T D F T L T I S S

Vκ2
k II 129     . . . V S N R D S G V P D R F S G S G S G . . T D F T L K I S R

Vλ1
a15          . . . N N Q R P S G V P D R F S G S K S G . . T S A S L A I S G
a22          . . . D N Q R P S G V P D R F S G S K S G . . T S A S L A I S G
a71          . . . N N K R P S G I P G R F S G S R S A . . T S A T L T I T G
k IV 107     . . . N T K R P S G I P D R F S G S K S G . . T S A T L G I T G
k I 12       . . . N N Q R P S G V P D R F S G S K S G . . T S A S L A I S G
a65          . . N M Q R P S G V P E R F S G S K S G . . T S A S L A I S G
a58          . . . V S K R P S G V P D R F S G S K S G . . N T A S L T V S G
k III 8      . . . N D Q R P S G V P D R F S G S R S G . . T S A S L A I T G
k III 10     . . . N N Q R P S G V P D R Y S A S K S G . . T S A S L A I S G
a10          . . . N N Q R P S G V P D R F S G S K S G . . T S A S L A I S G
k II 9a      . . . D N Q R P S G V P D R F S G S K S G . . T S A S L A I S G
k IV 78      . . . N N K R P S G I P D R F S G S K S G . . T S A T L D I T G
k I 22       . . . D T N R P S G V P D R F S G S R S G . . T S A S L A I T G
k II 20      . . . N N K R P S G I P D R F S G S K S G . . T S A T L G I T G
k III 20     . . . N N Q R P S G V P D R F S G S K S G . . T S A S L A I S G
k I 17       . . . Y N Q R P S G V P D R F S G S Q S G . . T S A S L A I S G
```

FIG. 13 (continued): Alignment of selected VL domain sequences

| AHo | 64 65 66 67 68 69 70 71 72 73 74 75 76 77 | 78 79 80 81 82 | 83 84 85 86 87 88 | 89 90 91 92 93 | 94 95 |
|---|---|---|---|---|---|
| Vλ2 | | | | | |
| a47 | . . . V N N R P A G V S N R F | S G S K S G | . . N T A S L T | I S G | |
| a59 | . . . V S N R P S G V S H R F | S G S K S G | . . N T A S L T | I S G | |
| a51 | . . . V N K R P S G V P D R F | S G S R S G | . . S T A S L T | I S G | |
| a24 | . . . V S N R P S G V S N R F | S G S K S G | . . N T A S L T | I S G | |
| k II 87 | . . . V S K R P S G V P D R F | S G S K S G | . . N T A S L T | I S G | |
| k I 2 | . . . T T K K H S W T P A R F | S G S L L G | . . G R A A L T | L S G | |
| Vλ3 | | | | | |
| a04 | . . . D D D R P S G I P E R F | S G S N S G | . . N T A T L T | I S R | |
| a33 | . . . D S V R P S G I P E R F | S G S N S G | . . N T A T L T | I S R | |
| a43 | . . . D S D R P S G I P E R F | S G S N S G | . . N T A T L T | I R R | |
| a08 | . . . D S E R P S G I P E R F | S G S N S G | . . N T A T L T | I S G | |
| a21 | . . . D S K R P S G I P E R F | S G S N S G | . . N T A T L T | I S G | |
| a fw1 | . . . N N K R P S G I P D R F | S G S P S G | . . T T A S L T | I S G | |
| a69 | . . . D S K R P S G I P E R F | S G S N S G | . . N T A T L T | I S G | |
| a49 | . . . D S D R P S G I P E R F | S G S N S G | . . N T A I L T | L S G | |
| a48 | . . . D N E R P S G I P E R F | S G S T S G | . . T T A T L T | I S G | |
| a46 | . . . N S R R P S G I P V R F | S G S K S G | . . S I A T L T | I S E | |
| a60 | . . . T N T R S S G V P D R F | S G S I L G | . . N K A A L T | I T G | |

FIG. 13 (continued): Alignment of selected VL domain sequences

AHo positions: 96 97 98 99 100 101 | 102 103 104 105 106 107 108 | 109 110 111 112 113 114 115 116 117 118 119 120 121 122 123 124 125 126 127

Vκ1

| ID | Sequence |
|---|---|
| a72 | L Q P E D I A T Y Y C Q Q F D N L . . . . . . . . . . . . |
| a02 | L Q P E D F A T Y Y C Q Q L Y S H . . . . . . . . . . . . |
| a44 | L Q P E D F A T Y Y C Q Q S S S T P . . . . . . . . . . . |
| a25 | L E P E D F A T Y Y C Q Q A Y R S . . . . . . . . . . . . |
| a68 | L Q P E D F A T Y Y C Q Q S Y S T . . . . . . . . . . . . |
| a28 | L Q P E D V A T Y Y C Q E Y D N L P . . . . . . . . . . . |
| a09 | L Q P E D T A T Y Y C Q Q N N K F . . . . . . . . . . . . |
| a62 | L Q P E D F A T Y Y C Q Q S Y S T . . . . . . . . . . . . |
| a54 | L Q P E D I A T Y Y C Q Q Y D V L . . . . . . . . . . . . |
| k IV 40 | L Q R E D F A T Y F C Q Q S Y S T . . . . . . . . . . . . |
| a fw5 | L Q P E D F A T Y Y C Q Q L Y S H . . . . . . . . . . . . |
| a fw8 | L Q P E D F A T Y Y C Q Q S F S S . . . . . . . . . . . . |
| a fw 10 | L Q P E D F A T Y Y C Q Q S Y R T . . . . . . . . . . . . |
| k I 27 | L Q P D D F A T Y Y C Q Q Y K S . . . . . . . . . . . . . |
| k III 25 | L Q P E D V A V Y Y C Q Q Y Y S L . . . . . . . . . . . . |
| a17 | L Q P D D L G T Y Y C Q Q Y K T Y . . . . . . . . . . . . |
| a61 | L Q P E D F V S Y Y C Q Q S F S T . . . . . . . . . . . . |
| a18 | L Q P E D V A T Y Y C Q Q Y D N L L P . . . . . . . . . . |
| a34 | L Q P E D F A T Y Y C Q Q T F R P . . . . . . . . . . . . |
| a45 | L Q P E D F G V Y F C Q Q T Y L T . . . . . . . . . . . . |
| a64 | L Q P E D F A T Y Y C Q Q S Y S S . . . . . . . . . . . . |
| k IV 98 | L Q P D D S A T Y Y C Q H Y D T Y . . . . . . . . . . . . |
| k II 86A | L Q P A D I G T Y Y C Q Q Y D N L . . . . . . . . . . . . |
| a53 | L Q P D D F A G Y Y C Q Q Y Y T Y . . . . . . . . . . . . |
| k II 42 | L Q P D D F A T Y Y C Q Q S Y D P P . . . . . . . . . . . |
| k II 114 | L Q P E D F A T Y Y C Q K Y N S A . . . . . . . . . . . . |
| k II 205 | L Q P D D F A T Y Y C Q Q S N S Y . . . . . . . . . . . . |
| k I 65 | L Q P E D F A T Y Y C Q Q S Y G T . . . . . . . . . . . . |
| k I 37 | L Q P D D S A T Y Y C Q Q Y K G Y . . . . . . . . . . . . |
| k III 23 | L E P E D F A V Y Y C Q Q F A R S . . . . . . . . . . . . |
| k IV 25 | L Q P E D F A I Y Y C Q Q S Y S T . . . . . . . . . . . . |
| k I 54 | L Q P D D C A T Y Y C Q Q S Y T T . . . . . . . . . . . . |
| k II 19 | L Q P E D I A T Y Y C Q Q Y D R . . . . . . . . . . . . . |
| k I 32 | L Q P E D C A T Y Y C L Q H S T Y . . . . . . . . . . . . |
| k I 34 | L Q H E D F A S Y Y C Q Q S Y T P . . . . . . . . . . . . |
| k I 19 | L Q P E D I A T Y Y C Q H Y H D F . . . . . . . . . . . . |
| k I 50 | L Q P E D I G T Y Y C Q Q Y D D F . . . . . . . . . . . . |
| k III 22 | L Q S E D F A T Y Y C Q Q Y Y S Y . . . . . . . . . . . . |
| k I 64 | L Q P E D F A T Y Y C L Q D Y N Y . . . . . . . . . . . . |

FIG. 13 (continued): Alignment of selected VL domain sequences

| AHo | 96 97 98 99 100 101 102 103 104 105 106 107 108 109 110 111 112 113 114 115 116 117 118 119 120 121 122 123 124 125 126 127 |
|---|---|
| Vκ1 | |
| k II 29 | L Q P E D F A T Y F C Q Q S D S A . . . . . . . . . . . . . . . . |
| k I 13 | L Q P E D S A T Y Y C Q Q T S G T . . . . . . . . . . . . . . . . |
| k I 9 | L Q P D D F A T Y Y C Q Q T Y S   . . . . . . . . . . . . . . . . . |
| k I 24 | L Q P G D F A T Y Y C Q Q T Y T T . . . . . . . . . . . . . . . . |
| k II 124 | L Q P D D F A T Y Y C Q Q Y S S Y . . . . . . . . . . . . . . . . |
| k II 10 | L Q A E D V A V Y Y C Q Q Y Y S T . . . . . . . . . . . . . . . . |
| Vκ3 | |
| a41 | L E P E D F A V Y Y C Q Q Y G S S . . . . . . . . . . . . . . . . |
| a01 | L E P E D Y A V Y Y C Q Q Y G S S . . . . . . . . . . . . . . . . |
| k IV 103 | L Q S E D F A A Y Y C Q Q Y K H W P . . . . . . . . . . . . . . . |
| k IV 135 | L E P E D S A L Y Y C Q Q R N S W . . . . . . . . . . . . . . . . |
| k II 190 | L E P E D F A V Y Y C Q Q Y G S S . . . . . . . . . . . . . . . . |
| k II 136 | L E P E D F A V Y Y C Q Q R S N W . . . . . . . . . . . . . . . . |
| Vκ2 | |
| k II 129 | V D A E D V G V Y Y C M Q G T H W . . . . . . . . . . . . . . . . |
| Vλ1 | |
| a15 | L R S E D E A D Y Y C A A W D D S L N . . . . . . . . . . . . . . |
| a22 | L Q S E D E A E Y Y C A T W D D S L N . . . . . . . . . . . . . . |
| a71 | L Q T G D E A D Y Y C G T W D S N L S . . . . . . . . . . . . . . |
| k IV 107 | L Q T G D E A D Y Y C G T W D S S L S . . . . . . . . . . . . . . |
| k I 12 | L R S E D E A H Y Y C A A W D D S L S . . . . . . . . . . . . . . |
| a65 | L Q S E D E A T Y Y C V T W D D S L N . . . . . . . . . . . . . . |
| a58 | L Q A E D E A D Y Y C S S Y A G N N . . . . . . . . . . . . . . . |
| k III 8 | L Q P Q D E A V Y F C Q S Y D S S L S G . . . . . . . . . . . . . |
| k III 10 | L Q S E D E A D Y Y C A A W D D S L S . . . . . . . . . . . . . . |
| a10 | L Q S E D E A D Y Y C A A W D D S L N . . . . . . . . . . . . . . |
| k II 9a | L Q S E D E A D Y Y C A A W D D S L N . . . . . . . . . . . . . . |
| k IV 78 | L Q T E D E A D Y Y C G T W D S S L G G . . . . . . . . . . . . . |
| k I 22 | L Q P Q D E A V Y F C Q S Y D S S L S G . . . . . . . . . . . . . |
| k II 20 | L Q T G D E A D Y Y C G T W D S S L N . . . . . . . . . . . . . . |
| k III 20 | L R S E D E A D Y Y C A A W D D G L N . . . . . . . . . . . . . . |
| k I 17 | L Q S E D E A D Y Y C A A W D D S L S . . . . . . . . . . . . . . |

FIG. 13 (continued): Alignment of selected VL domain sequences

| AHo | 96 97 98 99 100 101 | 102 103 104 105 106 107 108 | 109 110 111 112 113 114 115 116 117 118 119 120 121 122 123 124 125 126 127 |
|---|---|---|---|
| Vλ2 | | | |
| a47 | L Q A E D E | A E Y Y C S S | Y R S D N S . . . . . . . . . . . . . . |
| a59 | L Q A E D E | A D Y Y C C S | Y R G P S S . . . . . . . . . . . . . . |
| a51 | L Q A E D E | A D Y Y C C S | Y A G R Y T . . . . . . . . . . . . . . |
| a24 | L Q A E D E | A D Y Y C S S | C T S S S . . . . . . . . . . . . . . . |
| k II 87 | L Q A E D E | A D Y F C C S | Y A G S Y T . . . . . . . . . . . . . . |
| k I 2 | V Q P E D E | A E Y H C L L | Y Y G G P . . . . . . . . . . . . . . . |
| Vλ3 | | | |
| a04 | V E A G D E | A D Y Y C Q V | W E S G S G . . . . . . . . . . . . . . |
| a33 | V E A G D E | A D Y Y C Q V | W D S S S D . . . . . . . . . . . . . . |
| a43 | V E A G D E | A D Y Y C Q V | W D S S S D . . . . . . . . . . . . . . |
| a08 | T Q A M D E | A D Y Y C Q A | W D S N . . . . . . . . . . . . . . . . |
| a21 | T Q A M D E | A D Y Y C Q A | W D S S . . . . . . . . . . . . . . . . |
| a fw1 | A Q A E D E | A D Y Y C N S | R D S S G F . . . . . . . . . . . . . . |
| a69 | T Q A L D E | A D Y Y C Q A | W D T G . . . . . . . . . . . . . . . . |
| a49 | V E A G D E | A D Y Y C Q V | W D N D S D . . . . . . . . . . . . . . |
| a48 | V Q A E D E | G D Y Y C Q S | A D N N A A . . . . . . . . . . . . . . |
| a46 | T R A L D E | A N Y Y C Q A | W D S N . . . . . . . . . . . . . . . . |
| a60 | A Q A D D E | S D Y Y C V L | Y L G S G . . . . . . . . . . . . . . . |

FIG. 13 (continued): Alignment of selected VL domain sequences

| AHo | 128 | 129 | 130 | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|---|---|---|

Vκ1

| | | | | | | | | | | | | | | | | | | | | | | |
|---|---|---|---|---|---|---|---|---|---|---|---|---|---|---|---|---|---|---|---|---|---|---|
| a72 | . | . | . | . | . | . | . | . | . | P | F | T | F | G | P | G | T | K | V | D | I | K R |
| a02 | . | . | . | . | . | . | . | . | . | P | Y | T | F | G | Q | G | T | K | V | D | I | K R |
| a44 | . | . | . | . | . | . | . | . | . | P | Y | T | F | G | Q | G | T | K | V | E | I | K R |
| a25 | . | . | . | . | . | . | . | . | . | P | P | T | F | G | Q | G | T | K | V | D | I | K R |
| a68 | . | . | . | . | . | . | . | . | . | P | W | T | F | G | Q | G | T | K | L | E | I | K R |
| a28 | . | . | . | . | . | . | . | . | . | P | Y | I | F | G | Q | G | T | K | V | D | I | K R |
| a09 | . | . | . | . | . | . | . | . | . | P | L | T | F | G | G | G | T | K | L | T | V | L G |
| a62 | . | . | . | . | . | . | . | . | . | Q | W | T | F | G | Q | G | T | K | V | D | I | K R |
| a54 | . | . | . | . | . | . | . | . | . | P | P | A | F | G | Q | G | T | K | V | E | I | K R |
| k IV 40 | . | . | . | . | . | . | . | . | . | P | E | T | F | G | Q | G | T | K | V | E | I | K R |
| a fw5 | . | . | . | . | . | . | . | . | . | P | Y | T | F | G | Q | G | T | K | V | E | I | K R |
| a fw8 | . | . | . | . | . | . | . | . | . | P | L | T | F | G | G | G | T | K | V | E | I | K R |
| a fw 10 | . | . | . | . | . | . | . | . | . | P | F | T | F | G | P | G | T | K | V | E | I | K R |
| k I 27 | . | . | . | . | . | . | . | . | . | Y | W | T | F | G | Q | G | T | K | L | T | V | L G |
| k III 25 | . | . | . | . | . | . | . | . | . | P | Y | M | F | G | Q | G | T | K | V | D | I | K R |
| a17 | . | . | . | . | . | . | . | . | . | P | Y | T | F | G | Q | G | T | K | L | T | V | L G |
| a61 | . | . | . | . | . | . | . | . | . | P | R | T | F | G | Q | G | T | K | L | E | I | K R |
| a18 | . | . | . | . | . | . | . | . | . | Q | F | T | F | G | G | G | T | K | V | D | I | K R |
| a34 | . | . | . | . | . | . | . | . | . | L | W | T | F | G | Q | G | T | K | V | T | V | L G |
| a45 | . | . | . | . | . | . | . | . | . | P | P | T | F | G | G | G | T | K | V | E | I | K R |
| a64 | . | . | . | . | . | . | . | . | . | L | R | T | F | G | Q | G | T | R | L | E | I | K R |
| k IV 98 | . | . | . | . | . | . | . | . | . | P | W | T | F | G | L | G | T | K | L | E | I | K R |
| k II 86A | . | . | . | . | . | . | . | . | . | P | L | T | F | G | G | G | T | K | V | E | I | K R |
| a53 | . | . | . | . | . | . | . | . | . | P | W | T | F | G | R | G | T | K | V | D | I | K R |
| k II 42 | . | . | . | . | . | . | . | . | . | | I | F | T | F | G | P | G | T | K | V | E | I | K R |
| k II 114 | . | . | . | . | . | . | . | . | . | P | Y | T | F | G | Q | G | T | K | V | E | I | K R |
| k II 205 | . | . | . | . | . | . | . | . | . | P | W | T | F | G | Q | G | T | K | V | D | I | K R |
| k I 65 | . | . | . | . | . | . | . | . | . | | F | L | T | F | G | G | G | T | K | V | T | V | L G |
| k I 37 | . | . | . | . | . | . | . | . | . | | S | G | T | F | G | Q | G | T | K | V | T | V | L G |
| k III 23 | . | . | . | . | . | . | . | . | . | P | W | T | F | G | Q | G | T | K | L | T | V | L G |
| k IV 25 | . | . | . | . | . | . | . | . | . | P | I | T | F | G | Q | G | T | R | L | E | I | K R |
| k I 54 | . | . | . | . | . | . | . | . | . | P | W | T | F | G | P | G | T | K | V | D | I | K R |
| k II 19 | . | . | . | . | . | . | . | . | . | | F | L | T | F | G | G | G | T | K | V | E | I | K R |
| k I 32 | . | . | . | . | . | . | . | . | . | P | P | T | F | G | R | G | T | K | L | E | I | K R |
| k I 34 | . | . | . | . | . | . | . | . | . | P | W | T | F | G | Q | G | T | R | L | E | I | K R |
| k I 19 | . | . | . | . | . | . | . | . | . | P | Y | T | F | G | Q | G | T | R | L | E | I | K R |
| k I 50 | . | . | . | . | . | . | . | . | . | P | L | T | F | G | G | G | T | K | V | D | I | K R |
| k III 22 | . | . | . | . | . | . | . | . | . | P | F | T | F | G | G | G | T | K | V | E | I | K R |
| k I 64 | . | . | . | . | . | . | . | . | . | P | W | T | F | G | Q | G | T | K | V | E | I | K R |

FIG. 13 (continued): Alignment of selected VL domain sequences

| AHo | 128 | 129 | 130 | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|---|---|---|

Vκ1

| | | | | | | | | | | | | | | | | | | | | | | |
|---|---|---|---|---|---|---|---|---|---|---|---|---|---|---|---|---|---|---|---|---|---|---|
| k II 29 | . | . | . | . | . | . | . | . | . | P | W | T | F | G | Q | G | T | K | L | E | I | K R |
| k I 13 | . | . | . | . | . | . | . | . | . | P | H | S | F | G | Q | G | T | K | L | E | I | K R |
| k I 9 | . | . | . | . | . | . | . | . | . | S | C | T | F | G | R | G | T | K | V | T | V | L G |
| k I 24 | . | . | . | . | . | . | . | . | . | P | R | M | F | G | Q | G | T | K | V | T | V | L G |
| k II 124 | . | . | . | . | . | . | . | . | . | P | W | T | F | G | P | G | T | K | V | T | V | L G |
| k II 10 | . | . | . | . | . | . | . | . | . | P | Y | T | F | G | Q | G | T | Q | L | T | V | L G |

Vκ3

| | | | | | | | | | | | | | | | | | | | | | | |
|---|---|---|---|---|---|---|---|---|---|---|---|---|---|---|---|---|---|---|---|---|---|---|
| a41 | . | . | . | . | . | . | . | . | . | P | F | T | F | G | P | G | T | K | L | E | I | K R |
| a01 | . | . | . | . | . | . | . | . | . | P | L | T | F | G | G | G | T | K | L | T | V | L G |
| k IV 103 | . | . | . | . | . | . | . | . | . | P | W | T | F | G | Q | G | T | K | V | E | I | K R |
| k IV 135 | . | . | . | . | . | . | . | . | . | P | H | T | F | G | G | G | T | K | L | E | I | K R |
| k II 190 | . | . | . | . | . | . | . | . | . | P | R | T | F | G | Q | G | T | K | V | E | I | K R |
| k II 136 | . | . | . | . | . | . | . | . | . | P | P | T | F | G | G | G | T | K | L | T | V | L G |

Vκ2

| | | | | | | | | | | | | | | | | | | | | | | |
|---|---|---|---|---|---|---|---|---|---|---|---|---|---|---|---|---|---|---|---|---|---|---|
| k II 129 | . | . | . | . | . | . | . | . | . | P | P | T | F | G | Q | G | T | K | L | T | V | L G |

Vλ1

| | | | | | | | | | | | | | | | | | | | | | | |
|---|---|---|---|---|---|---|---|---|---|---|---|---|---|---|---|---|---|---|---|---|---|---|
| a15 | . | . | . | . | . | . | . | . | . | G | V | V | F | G | G | G | T | K | L | T | V | L G |
| a22 | . | . | . | . | . | . | . | . | . | G | Q | V | F | G | G | G | T | K | L | T | V | L G |
| a71 | . | . | . | . | . | . | . | . | . | A | A | V | F | G | G | G | T | K | L | T | V | L G |
| k IV 107 | . | . | . | . | . | . | . | . | . | G | V | V | F | G | G | G | T | K | L | T | V | L G |
| k I 12 | . | . | . | . | . | . | . | . | . | G | W | V | F | G | G | G | T | K | V | E | I | K R |
| a65 | . | . | . | . | . | . | . | . | . | H | W | L | F | G | G | G | T | K | L | T | V | L G |
| a58 | . | . | . | . | . | . | . | . | . | R | F | L | F | G | G | G | T | Q | L | T | V | L G |
| k III 8 | . | . | . | . | . | . | . | . | . | S | V | V | F | G | G | G | T | K | L | T | V | L G |
| k III 10 | . | . | . | . | . | . | . | . | . | A | F | V | F | G | G | G | T | Q | L | T | V | L G |
| a10 | . | . | . | . | . | . | . | . | . | G | V | V | F | G | G | G | T | K | L | T | V | L G |
| k II 9a | . | . | . | . | . | . | . | . | . | G | W | V | F | G | G | G | T | K | L | T | V | L G |
| k IV 78 | . | . | . | . | . | . | . | . | . | G | G | V | F | G | A | G | T | Q | L | T | V | L G |
| k I 22 | . | . | . | . | . | . | . | . | . | S | V | V | F | G | G | G | T | K | L | T | V | L G |
| k II 20 | . | . | . | . | . | . | . | . | . | A | Y | V | F | G | T | G | T | K | L | T | V | L G |
| k III 20 | . | . | . | . | . | . | . | . | . | G | V | V | F | G | G | G | T | K | V | T | V | L G |
| k I 17 | . | . | . | . | . | . | . | . | . | G | W | V | F | G | G | G | T | K | V | T | V | L G |

FIG. 13 (continued): Alignment of selected VL domain sequences

| AHo | 128 | 129 | 130 | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|---|---|---|
| Vλ2 | | | | | | | | | | | | | | | | | | | | | | |
| a47 | . | . | . | . | . | . | . | . | . | P | V | V | F | G | G | G | T | K | L | T | V | L G |
| a59 | . | . | . | . | . | . | . | . | . | P | Y | V | F | G | T | G | T | K | L | T | V | L G |
| a51 | . | . | . | . | . | . | . | . | . | V | F | A | F | G | P | G | T | K | V | T | V | L G |
| a24 | . | . | . | . | . | . | . | . | . | T | P | L | F | G | G | G | T | K | L | T | V | L G |
| k II 87 | . | . | . | . | . | . | . | . | . | P | Y | V | F | G | T | G | T | K | V | E | I | K R |
| k I 2 | . | . | . | . | . | . | . | . | . | Q | W | V | F | G | G | G | T | Q | L | T | V | L G |
| Vλ3 | | | | | | | | | | | | | | | | | | | | | | |
| a04 | . | . | . | . | . | . | . | . | . | Q | Y | F | F | G | P | G | T | K | L | T | V | L G |
| a33 | . | . | . | . | . | . | . | . | . | Y | V | V | F | G | G | G | T | K | L | T | V | L G |
| a43 | . | . | . | . | . | . | . | . | . | H | N | V | F | G | S | G | T | K | V | E | I | K R |
| a08 | . | . | . | . | . | . | . | . | . | T | V | V | F | G | G | G | T | K | L | T | V | L G |
| a21 | . | . | . | . | . | . | . | . | . | T | G | V | F | G | G | G | T | K | L | T | V | L G |
| a fw1 | . | . | . | . | . | . | . | . | . | H | L | V | F | G | G | G | T | K | L | T | V | L . |
| a69 | . | . | . | . | . | . | . | . | . | T | V | V | F | G | G | G | T | K | V | E | I | K . |
| a49 | . | . | . | . | . | . | . | . | . | H | W | V | F | G | G | G | T | K | L | T | V | L G |
| a48 | . | . | . | . | . | . | . | . | . | H | R | V | F | G | T | G | T | K | L | T | V | L G |
| a46 | . | . | . | . | . | . | . | . | . | T | V | L | F | G | G | G | T | K | L | T | V | L G |
| a60 | . | . | . | . | . | . | . | . | . | V | W | V | F | G | G | G | T | K | L | T | V | L G |

FIG. 14 : Alignment of random library members

| AHo | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|---|---|---|---| random VH

| | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| 1a | Q | V | T | L | K | E | S | . | G | A | E | V | K | K | P | G | S | S | V | R | V | S | C | K | T | S | G | . | G | P | F |
| 1a | Q | V | Q | L | Q | E | S | . | G | A | E | V | K | K | P | G | S | S | V | K | V | S | C | K | A | S | G | . | G | T | F |
| 1a | Q | V | Q | L | V | Q | S | . | G | A | E | V | K | K | P | G | S | S | V | K | V | S | C | K | A | S | G | . | G | S | F |
| 1b | E | V | Q | L | V | E | T | . | G | A | E | V | K | K | P | G | A | S | V | K | V | S | C | Q | A | S | G | . | Y | T | F |
| 1b | E | V | Q | L | G | E | S | . | G | A | E | V | K | K | P | G | A | T | V | K | V | S | C | R | A | S | G | . | Y | T | F |
| 1b | E | V | Q | L | V | E | S | . | G | P | E | V | K | K | P | G | A | S | M | K | L | S | C | Q | A | S | E | . | Y | S | F |
| 1b | Q | V | Q | L | V | Q | S | . | G | A | E | V | K | K | P | G | A | S | V | K | V | S | C | R | L | S | G | . | Y | T | L |
| 1b | Q | V | Q | L | V | Q | S | . | G | A | E | V | K | K | P | G | E | S | L | R | I | S | C | Q | S | S | G | . | Y | G | F |
| 1b | E | V | Q | L | V | E | S | . | G | V | E | V | K | K | P | G | E | S | L | K | L | S | C | K | G | A | G | . | Y | S | F |
| 1b | E | V | Q | L | V | E | S | . | G | A | E | V | K | E | P | G | E | S | L | R | I | S | C | Q | G | S | G | . | Y | S | F |
| 1b | E | V | Q | L | V | E | T | . | G | V | E | V | K | K | P | G | E | S | L | K | I | S | C | K | G | S | G | . | Y | F | F |
| 1b | E | V | Q | L | V | E | T | . | G | T | E | V | K | K | P | G | S | S | V | K | A | S | C | K | V | S | G | . | D | S | F |
| 3 | E | V | Q | L | V | Q | S | . | G | G | G | L | V | K | P | G | R | S | L | R | L | S | C | K | V | S | G | . | F | N | F |
| 3 | E | V | Q | L | V | E | S | . | G | G | G | V | V | Q | P | G | R | S | L | R | L | S | C | A | A | S | G | . | F | T | F |
| 3 | E | V | Q | L | V | Q | S | . | G | G | G | L | V | Q | P | G | G | S | L | R | L | S | C | A | A | S | G | . | F | A | F |
| 3 | Q | L | Q | L | Q | E | S | . | G | G | G | L | V | Q | P | G | G | S | L | R | L | S | C | A | A | S | G | . | F | N | I |
| 3 | E | V | Q | L | V | E | S | . | G | G | T | L | I | K | P | G | G | S | L | K | L | S | C | E | V | S | G | . | F | T | V |
| 4 | Q | L | Q | L | Q | E | S | . | G | P | G | L | V | K | P | S | Q | T | L | S | L | T | C | T | V | S | G | . | G | S | I |
| 4 | E | V | Q | L | V | E | S | . | G | A | E | . | V | K | P | S | Q | T | L | S | L | T | C | T | V | S | G | . | A | S | I |
| 4 | Q | L | Q | L | Q | E | S | . | G | P | G | L | V | K | P | S | E | T | L | S | L | T | C | T | V | S | G | . | G | S | M |
| 4 | Q | V | Q | L | Q | E | W | . | G | P | R | L | V | K | P | S | A | T | L | S | L | T | C | T | V | S | G | . | D | S | T |
| 4 | Q | L | Q | L | Q | E | S | . | G | P | G | L | V | K | P | S | G | A | L | S | L | T | C | T | V | S | G | . | D | S | I |
| 4 | Q | L | Q | L | Q | E | S | . | G | P | R | L | V | K | P | S | E | T | L | S | L | C | A | V | S | G | . | Y | S | I |  | random VL

| | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| k1 | E | I | V | L | T | Q | S | P | S | F | L | S | A | F | V | G | D | R | V | T | V | T | C | R | T | S | Q | . | . | D | I |
| k1 | E | I | V | L | T | Q | S | P | S | F | L | S | A | S | V | G | D | R | V | T | I | T | C | R | A | S | Q | . | . | D | I |
| k1 | E | I | V | M | T | Q | S | P | S | S | L | S | A | S | V | G | D | R | V | T | I | T | C | R | A | S | Q | . | . | D | I |
| k1 | D | V | V | M | T | Q | S | P | S | S | L | S | A | S | V | G | D | R | V | T | I | T | C | R | A | S | Q | . | . | S | I |
| k1 | E | I | V | L | T | Q | S | P | S | I | P | P | S | S | V | G | D | R | V | T | I | T | C | R | A | S | Q | . | . | S | I |
| k1 | E | I | V | M | T | Q | S | P | S | S | L | S | A | S | V | G | D | R | V | T | I | T | C | Q | A | S | E | . | . | D | I |
| k1 | D | I | Q | M | T | Q | S | P | S | S | L | S | A | S | V | G | D | R | V | T | I | T | C | Q | A | S | Q | . | . | D | I |
| k1 | D | I | Q | L | T | Q | S | P | S | S | L | S | A | S | V | G | D | R | V | T | I | T | C | R | A | S | Q | . | . | S | I |
| k1 | E | I | V | L | T | Q | S | P | S | S | L | S | A | S | I | G | D | R | V | T | L | T | C | R | S | S | Q | . | . | S | I |
| k1 | E | I | V | L | T | Q | F | P | S | S | V | S | A | S | V | G | D | R | V | T | I | T | C | Q | A | S | R | . | . | D | I |
| k1 | E | I | V | L | T | Q | S | P | S | S | V | S | A | S | V | G | E | R | A | T | L | S | C | R | A | S | H | . | . | S | V |
| k2 | E | I | V | L | T | Q | S | P | L | S | L | A | V | T | P | G | E | P | A | S | I | S | C | T | S | S | Q | . | . | R | L |
| k2 | E | I | V | L | T | Q | S | P | L | S | L | P | V | T | P | G | E | P | A | S | I | S | C | R | S | S | Q | . | . | S | L |

FIG. 14 (continued): Alignment of random library members

| AHo | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|---|---|---|---|
| random VL | | | | | | | | | | | | | | | | | | | | | | | | | | | | | | | |
| k3 | E | I | V | M | T | Q | S | P | G | T | L | S | L | S | P | G | E | R | A | T | L | S | C | R | A | S | Q | . | . | S | V |
| k3 | D | V | V | M | T | Q | S | P | G | T | L | S | L | S | P | G | E | R | A | T | L | S | C | R | A | S | Q | . | . | S | V |
| k3 | E | I | V | L | T | Q | S | P | G | T | L | S | L | S | P | G | E | R | A | T | L | S | C | R | A | S | Q | . | . | S | V |
| k3 | E | I | V | M | T | Q | S | P | A | T | L | S | V | S | P | G | E | R | A | T | L | S | C | R | A | S | R | . | . | G | V |
| k4 | D | I | Q | L | T | Q | S | P | D | S | L | A | V | S | L | G | E | R | A | T | T | H | C | K | S | S | Q | . | . | S | V |
| k4 | D | I | Q | M | T | Q | S | P | D | S | L | A | V | S | L | G | E | R | A | T | I | N | C | K | S | S | H | . | . | N | L |
| k4 | D | I | Q | L | T | Q | S | P | E | S | L | A | V | S | L | G | E | R | A | T | I | N | C | K | A | S | Q | . | . | S | L |
| l1 | Q | S | V | L | T | Q | . | P | P | S | A | S | G | T | P | G | Q | R | V | T | I | S | C | A | G | S | R | . | . | S | N |
| l2 | Q | S | A | L | T | Q | . | P | A | S | V | S | G | S | P | G | Q | S | I | T | I | S | C | T | G | T | S | . | . | S | D |
| l3 | Q | S | V | V | T | Q | . | P | P | S | V | S | A | A | P | G | Q | K | V | T | I | S | C | S | G | S | S | . | . | S | N |
| l3 | Q | S | V | L | A | Q | . | P | P | S | L | T | V | S | P | G | G | T | V | T | L | T | C | A | S | S | T | . | . | G | A |

FIG. 14 (continued): Alignment of random library members

| AHo | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 |
|---|---|---|---|---|---|---|---|---|---|---|---|---|---|---|---|---|---|---|---|---|---|---|---|---|---|---|---|---|---|---|---|---|
| random VH | | | | | | | | | | | | | | | | | | | | | | | | | | | | | | | | |
| 1a | S | N | . | . | . | . | . | . | H | S | I | S | W | V | R | Q | A | P | G | Q | G | L | E | W | M | A | G | F | I | P | . | . | . |
| 1a | S | N | . | . | . | . | . | . | Y | V | I | A | W | V | R | Q | A | P | G | D | G | L | E | W | M | G | A | V | I | P | . | . | . |
| 1a | S | S | . | . | . | . | . | . | Y | G | M | S | W | L | R | Q | A | P | G | Q | G | L | E | W | V | G | V | V | V | P | . | . | . |
| 1b | T | S | . | . | . | . | . | . | Y | N | I | N | W | V | R | Q | A | T | G | Q | G | L | E | W | M | G | R | M | N | P | . | . | . |
| 1b | N | L | . | . | . | . | . | . | Y | D | M | N | W | V | R | Q | A | T | G | Q | G | L | E | W | M | G | W | M | N | P | . | . | . |
| 1b | S | T | . | . | . | . | . | . | I | Y | M | H | W | V | R | Q | A | P | G | Q | G | L | E | W | M | G | I | V | I | P | . | . | . |
| 1b | T | K | . | . | . | . | . | . | L | A | F | H | W | V | R | Q | A | P | G | K | G | L | E | W | M | Q | T | F | D | P | . | . | . |
| 1b | S | K | . | . | . | . | . | . | S | W | I | T | W | V | R | Q | V | P | G | K | G | L | E | W | M | G | R | I | D | P | . | . | . |
| 1b | S | S | . | . | . | . | . | . | Y | L | I | A | W | V | R | Q | M | P | G | K | G | L | E | W | V | A | M | I | Y | P | . | . | . |
| 1b | T | T | . | . | . | . | . | . | Y | W | I | N | W | V | R | Q | M | P | G | K | G | L | E | W | M | G | K | I | D | P | . | . | . |
| 1b | T | N | . | . | . | . | . | . | Y | W | I | A | W | V | R | Q | M | P | G | K | G | L | Q | W | M | G | I | I | Y | P | . | . | . |
| 1b | S | D | . | . | . | . | . | . | Y | S | F | R | W | V | R | Q | A | P | G | Q | G | L | E | W | M | G | G | I | T | P | . | . | . |
| 3 | P | D | . | . | . | . | . | . | Y | A | I | N | W | V | R | Q | A | P | G | K | G | L | E | F | V | G | R | V | K | R | N | T | . |
| 3 | S | D | . | . | . | . | . | . | A | W | M | S | W | V | R | Q | A | P | G | T | G | L | E | W | V | G | R | I | K | S | K | T | . |
| 3 | S | N | . | . | . | . | . | . | Y | E | M | N | W | V | R | Q | A | P | G | K | G | L | V | W | I | S | Y | I | S | S | Y | S | . |
| 3 | S | N | . | . | . | . | . | . | Y | D | M | H | W | V | R | Q | A | T | G | K | G | L | E | W | V | S | A | I | D | T | . | . | . |
| 3 | G | G | . | . | . | . | . | . | N | Y | I | S | W | V | R | Q | A | P | G | K | R | L | E | W | V | S | A | I | Y | S | . | . | . |
| 4 | S | N | G | G | . | . | . | . | Y | Y | W | S | W | I | R | Q | H | P | G | K | G | L | E | W | I | G | Y | I | Y | Y | . | . | . |
| 4 | S | S | G | V | . | . | . | . | Y | Y | W | S | W | L | R | Q | S | P | G | K | G | L | E | W | I | G | Y | I | Y | Y | . | . | . |
| 4 | S | D | . | . | . | . | . | . | Y | Y | W | T | W | I | R | Q | A | P | G | K | G | L | E | W | M | G | Y | I | Y | Y | . | . | . |
| 4 | S | S | . | . | . | . | . | . | T | Y | W | S | W | I | R | Q | P | P | G | K | G | L | E | W | I | G | D | V | Y | Y | . | . | . |
| 4 | T | G | S | . | . | . | . | . | G | W | W | N | W | V | R | Q | A | P | G | K | G | L | E | W | I | A | E | I | Y | H | . | . | . |
| 4 | S | N | N | . | . | . | . | . | Y | Y | W | G | W | I | R | Q | P | P | G | K | G | L | E | W | I | G | S | I | Y | H | . | . | . |
| random VL | | | | | | | | | | | | | | | | | | | | | | | | | | | | | | | | |
| k1 | R | . | . | . | . | . | . | . | N | S | L | A | W | Y | Q | Q | K | P | G | E | A | P | K | L | L | I | Y | L | . | . | . | . | . |
| k1 | S | . | . | . | . | . | . | . | R | A | I | V | W | Y | Q | Q | K | P | G | T | V | P | K | F | L | I | Y | G | . | . | . | . | . |
| k1 | A | . | . | . | . | . | . | . | R | Y | L | N | W | Y | Q | Q | K | P | G | K | A | P | N | L | L | I | Y | D | . | . | . | . | . |
| k1 | S | . | . | . | . | . | . | . | S | Y | L | N | W | Y | Q | Q | K | P | G | K | A | P | K | L | L | I | Y | A | . | . | . | . | . |
| k1 | S | . | . | . | . | . | . | . | K | Y | I | N | W | Y | Q | Q | K | P | G | K | A | P | N | L | L | I | Y | D | . | . | . | . | . |
| k1 | T | . | . | . | . | . | . | . | N | Y | L | N | W | Y | Q | Q | K | P | G | K | A | P | N | L | L | I | F | D | . | . | . | . | . |
| k1 | S | . | . | . | . | . | . | . | N | Y | L | N | W | Y | Q | Q | K | P | G | K | A | P | K | L | L | I | Y | D | . | . | . | . | . |
| k1 | T | . | . | . | . | . | . | . | . | L | L | V | W | Y | Q | Q | R | P | G | E | A | P | T | L | L | I | Y | T | . | . | . | . | . |
| k1 | S | . | . | . | . | . | . | . | K | Y | V | N | W | Y | Q | Q | R | P | G | R | A | P | Q | L | L | V | Y | V | . | . | . | . | . |
| k1 | R | . | . | . | . | . | . | . | N | H | L | N | W | Y | Q | Q | R | L | G | K | A | P | K | L | L | I | Y | D | . | . | . | . | . |
| k1 | S | . | . | . | . | S | S | S | L | A | W | Y | Q | Q | K | P | G | Q | A | P | S | L | L | I | H | G | . | . | . | . | . | . | . |
| k2 | L | H | S | . | N | G | H | N | Y | L | D | W | Y | L | Q | K | P | G | Q | S | P | H | L | L | I | Y | L | . | . | . | . | . |
| k2 | L | Y | T | . | N | G | Y | N | Y | L | D | W | Y | L | Q | K | P | G | Q | S | P | E | V | L | I | Y | L | . | . | . | . | . |

FIG. 14 (continued): Alignment of random library members

| AHo | 32 33 34 35 36 37 38 39 40 | 41 42 43 44 45 46 47 | 48 49 50 | 51 52 53 54 55 56 57 | 58 59 60 61 62 63 |
|---|---|---|---|---|---|
| random VL | | | | | |
| k3 | S . . . . . G S | H L A W F | Q Q R | P G Q A P R L | L I H S . . . . . . |
| k3 | N . . . . . I N S | L A W Y | Q Q K | P G Q A P R L | L I Y G . . . . . . |
| k3 | T . . . . . S S H | L G W Y | Q Q N | L G Q A P R L | L I Y G . . . . . . |
| k3 | S . . . . . . D K V | A R Y | Q H K | P G Q A P S L | L I H G . . . . . . |
| k4 | L Y S I N N K N Y | L A W Y | Q H R | P G Q P P R L | L I Y W . . . . . . |
| k4 | L Y S S N N Y N Y | L A W Y | Q Q K | P G Q P P K L | L I Y W . . . . . . |
| k4 | S S R S K N R N Y | L T W Y | Q H K | P G Q P P K V | L I Y W . . . . . . |
| l1 | I . . . G T . N S | V N W Y | Q Q V | P G G A P K L | L I F A . . . . . . |
| l2 | V . . . G T L K Y | V S W Y | Q Q H | P G K A P K L | M I Y E . . . . . . |
| l3 | I . . . G N . N Y | V S W Y | Q Q V | P G T A P K L | L I S D . . . . . . |
| l3 | V . . . T R G Y Y | P T W F | Q Q K | P G Q T P R S | L I Y S . . . . . . |

FIG. 14 (continued): Alignment of random library members

| AHo | 64 65 66 67 68 69 70 71 72 73 74 75 76 77 78 79 80 81 82 83 84 85 86 87 88 89 90 91 92 93 94 95 |
|---|---|
| random VH | |
| 1a | I F G S A N Y A Q K F R G R V R V S A D E S T S T A Y M E L S S |
| 1a | I F G S A K Y A Q K F Q A R V T I I A D K S T S T A Y M E L T S |
| 1a | M Y G T S N N A Q K F Q G R V S I T A D T S T N T A Y L E L S S |
| 1b | I T G D T G Y A Q K F Q G R V T L T R D T S I R T A Y M K L S S |
| 1b | K S G N T G Y A Q K F Q G R A T M T C D T A T N T A Y M E L T N |
| 1b | S G S T N . Y A Q K F Q G R I T M T R D K S T S T V F L E L K T |
| 1b | D D A D P L Y A Q T F Q G R V T V T E D P S T D T A S L E L S N |
| 1b | S D S Y I N Y S P S F Q G H I T I S H D K S I S T A Y L Q W S S |
| 1b | S D S D T R Y S P S F Q G H V T I S V D K S S S T A Y L Q W S S |
| 1b | T D S E V N Y S P S F Q G H V T I S V D K S I D T A F L Q W S S |
| 1b | G D S E T R Y S P S F Q G Q V T I S A D K S I N T A H L Q W S S |
| 1b | I F G S P N Y A E N F E G K I S I T A D E S T V T V F L E L S S |
| 3 | E G G A I D Y A A P V E G R F T I S R D D S E N K V Y L Q M N S |
| 3 | D A G T I D Y A A P V K G R F T I S R D D S K N T L Y L Q M N S |
| 3 | . . S T I Y L A D S V K G R F T I S R D D A Q N S V Y L Q M D S |
| 3 | . A G D T Y Y P G S V K G R F T M S R E K A R N S L Y L Q M N S |
| 3 | . G G S T Y Y G D S V K G R F S M S R D T S K N T L F L Q M D R |
| 4 | . S G A T Y Y N P S L K S R V T I S V D T S K N Q F S L N L S P |
| 4 | T G T T T Y Y N P T L E S R V T I S L D T A K N Q F S L K L S S |
| 4 | . S G G T H Y N P S L Q S R V T I S L D T S K N Q F S L R L F S |
| 4 | . T G S T N Y N P S L K S R V T L T V D E S K S Q F S L K L M S |
| 4 | . S G S T H Y N P S L K S R V T L T V D K S N N S F S L R L T S |
| 4 | . S G N T H Y N P S L K S R V T I S V D T S K N Q F S L K L T S |
| random VL | |
| k1 | . . . A S T L Q T G V P S R F S G S G S G . . T E F T L T I S G |
| k1 | . . . A S T S Q S G V P S R F S G S G S G . . T E F T L T I S S |
| k1 | . . . A T T L R G G V P S R F S A S G S G . . T D F T L T I S S |
| k1 | . . . A S S L Q S G V P S R F S G S G S G . . T D F T L T I S S |
| k1 | . . . A S N L Q S G V P S R F S G S G S G . . T D F T L T I S S |
| k1 | . . . T S S L Q S G V P S R F S G S G S G . . T D F T L T I S S |
| k1 | . . . A S H L E T G V P S R F T G S G S G . . T D F T L T I S S |
| k1 | . . . A S N L Q T G V P S R F S G S G S G . . T D F T L T I S N |
| k1 | . . . A T N L P W G V P S R F S G S G S G . . T D F A L T I D N |
| k1 | . . . A S T L E T G V P S R F S G S G S G . . T S F T F T I S S |
| k1 | . . . T S S R A T G I P D R F S G S G S G . . T D F T L T I S R |
| k2 | . . . G S N R A S G V P D R V G G S G S G . . T H F T L N I S R |
| k2 | . . . G S K R A S G V P D R I S G S G S G . . T D F T L T I S R |

FIG. 14 (continued): Alignment of random library members

| AHo | 64 65 66 67 68 69 70 71 72 73 74 75 76 77 | 78 79 80 81 82 | 83 84 85 86 87 88 | 89 90 91 92 93 | 94 95 |
|---|---|---|---|---|---|
| random VL | | | | | |
| k3 | . . . A S S R A T G I P D R F | S G S G S G | . . T D F T L | T I S R | |
| k3 | . . . A P S R A T G I P D R F | S G S G S G | . . T D F T L | T I S R | |
| k3 | . . . T S N R A T G I P D R F | S G S G S G | . . T D F T L | T I S R | |
| k3 | . . . V S T R A T D V P D R F | S G S G S G | . . T E F T L | T I S S | |
| k4 | . . . S S T R E S G V P D R F | S G S G S G | . . T D F T L | T I S S | |
| k4 | . . . A S T R E S G V P D R F | S G S G S G | . . T D F T L | T I S S | |
| k4 | . . . A S T R E S G V P D R F | S G S G S G | . . T D F T L | T I S S | |
| l1 | . . . N N E R A S G V P D R F | S G S K S G | . . T S A S L | A I S G | |
| l2 | . . . V S N R P S G V P D R F | S G S K S G | . . N T A S L | T I S G | |
| l3 | . . . N D K R P S G I P D R F | S G S K S G | . . T S A T L | G I T G | |
| l3 | . . . A R N K H S W T P A R F | S G S L L G | . . D K A A L | T L S G | |

FIG. 14 (continued): Alignment of random library members

| AHo | 96 97 98 99 100 101 | 102 103 104 105 106 107 108 | 109 110 111 112 113 114 115 116 117 118 119 120 121 122 123 124 125 126 127 |
|---|---|---|---|
| random VH | | | |
| 1a | | L R S D D T | A V Y Y C A R D P G R S G Y D L V G W |
| 1a | | L R S E D T | A V Y Y C A W G P M L Y G G S C Y |
| 1a | | L T F E D T | A V Y Y C A R R G T N S L |
| 1b | | L R S E D T | G V Y Y C V R V A M R G A N Y D T |
| 1b | | L R S D D T | A V Y Y C A R Q F K G N G W Y E S Y |
| 1b | | L S P N D T | A V Y Y C A T G R G G Y I V N A |
| 1b | | L T S E D T | G V Y Y C A T T S T G Y D V G A |
| 1b | | L K A S D T | A M Y Y C A G R E F S A Y D S M |
| 1b | | L K A S D T | A T Y Y C A R R G K D Y D G H H G |
| 1b | | L K A S D T | A I Y Y C A R R N E D L R Y N Y G |
| 1b | | L K P S D T | A M Y Y C A R P G S A G |
| 1b | | L R S E D T | A I Y Y C A S A P G G V T V P G A T R E A S |
| 3 | | L K T E D T | A V Y Y C S V G L G K T D |
| 3 | | L K T E D T | A V Y Y C T N I L R A G P L G D S |
| 3 | | L R A E D T | A V Y Y C A R G F L L S T T W Y Y |
| 3 | | L R A G D T | A V Y Y C A T G T |
| 3 | | L R G D D T | A I Y Y C A R F G N L G I G A |
| 4 | | V T A A D T | A V Y Y C A R F D Q S S G R L |
| 4 | | V T A A D T | A V Y Y C A R A D K S G Y S L |
| 4 | | G T A A D T | A V Y Y C A R I G A G Y G G N P Y E A W Y |
| 4 | | V T A A D T | A V Y Y C A R V N P R D P S G W F H |
| 4 | | V T A A D T | A V Y Y C A K S A G Y S Y A P |
| 4 | | V T A A D T | A V Y Y C A R D D F F G S G T Y F G G |
| random VL | | | |
| k1 | | L Q P E D C | A T Y Y C Q Q L N S H |
| k1 | | L Q P Q D F | A T Y Y C Q H V H S H |
| k1 | | L Q P E D F | A T Y Y C L Q D Y G Y |
| k1 | | L Q P E D F | A T Y Y C Q Q S Y S T |
| k1 | | L Q P E D F | A T Y Y C Q Q T Y N T |
| k1 | | L Q P E D F | A T Y Y C Q Q S Y S T |
| k1 | | L Q P E D I | A T Y Y C Q Q F D N |
| k1 | | L Q P E D F | A T Y Y C Q Q S Y S T |
| k1 | | V Q P E D F | A T Y Y C Q Q M Y E T P |
| k1 | | L Q P E D I | A T Y Y C Q V Y R D L |
| k1 | | L E P E D F | A V Y Y C Q Q Y D S |
| k2 | | V E A E D V | G V Y Y C M Q A L Q T |
| k2 | | V E A A D V | G V Y Y C M Q G L Q L |

FIG. 14 (continued): Alignment of random library members

| AHo | 96 97 98 99 100 101 | 102 103 104 105 106 107 108 | 109 110 111 112 113 114 115 116 117 118 119 120 121 122 123 124 125 126 127 |
|---|---|---|---|
| random VL | | | |
| k3 | L E P E D F | A V Y Y C Q Q | Y G S S P . . . . . . . . . . . . . . |
| k3 | L E S E D F | A V Y F C Q Q | Y T F S . . . . . . . . . . . . . . . |
| k3 | V E P E D F | A V Y Y C Q Q | F D I S . . . . . . . . . . . . . . . |
| k3 | V Q S E D F | A V Y F C Q Q | Y N T W P . . . . . . . . . . . . . . |
| k4 | L Q A E D V | A V Y Y C Q Q | Y Y D T . . . . . . . . . . . . . . . |
| k4 | L Q A E D V | A V Y Y C H Q | Y Y N T . . . . . . . . . . . . . . . |
| k4 | L Q A E D V | A L Y Y C Q Q | Y Y S I . . . . . . . . . . . . . . . |
| l1 | L Q S E D E | A D Y Y C A T | W D D S L N . . . . . . . . . . . . . |
| l2 | L Q A E D E | A D F Y C T S | Y T S S S . . . . . . . . . . . . . . |
| l3 | L Q T G D E | A D Y Y C G T | W D I S L S . . . . . . . . . . . . . |
| l3 | V Q P E D E | A E Y Y C L L | H Y A G . . . . . . . . . . . . . . . |

FIG. 14 (continued): Alignment of random library members

| AHo | 128 | 129 | 130 | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|---|---|---|
| random VH | | | | | | | | | | | | | | | | | | | | | | |
| 1a | . | . | . | . | . | . | . | . | . | L | D | P | W | G | Q | G | T | L | V | T | V | S S |
| 1a | . | . | . | . | . | . | . | . | . | F | D | I | W | G | Q | G | T | L | V | T | V | S S |
| 1a | . | . | . | . | . | . | . | . | . | P | D | S | W | G | Q | G | T | L | V | T | V | S S |
| 1b | . | . | . | . | . | . | . | . | . | S | G | L | W | G | Q | G | T | L | V | T | V | S S |
| 1b | . | . | . | . | . | . | . | . | . | F | K | L | W | G | Q | G | T | L | V | T | V | S S |
| 1b | . | . | . | . | . | . | . | . | . | F | D | I | W | G | Q | G | T | T | V | T | V | S S |
| 1b | . | . | . | . | . | . | . | . | . | F | D | I | W | G | Q | G | T | L | V | T | V | S S |
| 1b | . | . | . | . | . | . | . | . | . | G | D | F | W | G | Q | G | T | L | V | T | V | S S |
| 1b | . | . | . | . | . | . | . | . | . | L | D | Y | W | G | Q | G | T | L | V | T | V | S S |
| 1b | . | . | . | . | . | . | . | . | . | M | D | V | W | G | Q | G | T | L | V | T | V | S S |
| 1b | . | . | . | . | . | . | . | . | . | L | D | S | W | G | Q | G | T | L | V | T | V | S S |
| 1b | . | . | . | . | . | . | . | . | . | L | E | S | W | G | Q | G | T | L | V | T | V | S S |
| 3 | . | . | . | . | . | . | . | . | . | S | D | C | W | G | Q | G | T | T | V | T | V | S S |
| 3 | . | . | . | . | . | . | . | . | . | F | D | Y | W | G | Q | G | T | L | V | T | V | S S |
| 3 | . | . | . | . | . | . | . | . | . | F | D | S | W | G | P | G | T | T | V | T | V | S S |
| 3 | . | . | . | . | . | . | . | . | . | M | D | V | W | G | Q | G | T | L | V | T | V | S S |
| 3 | . | . | . | . | . | . | . | . | . | F | D | A | W | G | H | G | T | T | V | T | V | S S |
| 4 | . | . | . | . | . | . | . | . | . | . | . | . | . | G | P | G | T | T | V | T | V | S S |
| 4 | . | . | . | . | . | . | . | . | . | C | D | Y | W | G | Q | G | T | T | V | T | V | S S |
| 4 | . | . | . | . | . | . | . | . | . | F | D | L | W | G | R | G | T | L | V | T | V | S S |
| 4 | . | . | . | . | . | . | . | . | . | F | D | L | W | G | Q | G | T | L | V | T | V | S S |
| 4 | . | . | . | . | . | . | . | . | . | L | D | S | W | G | L | G | T | L | V | T | V | S S |
| 4 | . | . | . | . | . | . | . | . | . | A | Q | Y | W | G | Q | G | T | L | V | T | V | S S |
| random VL | | | | | | | | | | | | | | | | | | | | | | |
| k1 | . | . | . | . | . | . | . | . | . | P | L | T | F | G | G | G | T | K | V | E | I | K R |
| k1 | . | . | . | . | . | . | . | . | . | P | L | A | F | G | G | G | T | K | L | E | I | K R |
| k1 | . | . | . | . | . | . | . | . | . | P | R | T | F | G | Q | E | T | K | V | D | I | K R |
| k1 | . | . | . | . | . | . | . | . | . | P | W | T | F | G | Q | G | T | K | V | E | I | K R |
| k1 | . | . | . | . | . | . | . | . | . | P | Y | T | F | G | Q | G | T | K | V | D | I | K R |
| k1 | . | . | . | . | . | . | . | . | . | R | F | T | F | G | P | G | T | K | V | D | I | K R |
| k1 | . | . | . | . | . | . | . | . | . | L | N | T | F | G | Q | G | T | K | V | E | I | K R |
| k1 | . | . | . | . | . | . | . | . | . | P | R | T | F | G | Q | G | T | K | V | E | I | K R |
| k1 | . | . | . | . | . | . | . | . | . | G | G | S | F | G | R | G | T | K | V | E | I | K R |
| k1 | . | . | . | . | . | . | . | . | . | L | F | T | F | G | P | G | T | K | L | E | I | K R |
| k1 | . | . | . | . | . | . | . | . | . | S | W | T | F | G | Q | G | T | K | V | D | I | K R |
| k2 | . | . | . | . | . | . | . | . | . | P | Y | T | F | G | Q | G | T | K | V | D | I | K R |
| k2 | . | . | . | . | . | . | . | . | . | P | L | T | F | G | G | G | T | K | V | D | I | K R |

FIG. 14 continued): Alignment of random library members

| AHo | 128 | 129 | 130 | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|---|---|---|
| random VL | | | | | | | | | | | | | | | | | | | | | | |
| k3 | . | . | . | . | . | . | . | . | . | R | F | T | F | G | P | G | T | K | L | E | I | K R |
| k3 | . | . | . | . | . | . | . | . | . | S | W | T | F | G | Q | G | T | K | V | D | I | K R |
| k3 | . | . | . | . | . | . | . | . | . | P | Y | T | F | A | L | G | P | A | G | D | Q | T W |
| k3 | . | . | . | . | . | . | . | . | . | P | Y | T | F | G | Q | G | T | K | V | D | I | K R |
| k4 | . | . | . | . | . | . | . | . | . | P | G | T | F | G | Q | G | T | K | V | D | I | K R |
| k4 | . | . | . | . | . | . | . | . | . | P | Q | T | F | G | Q | G | T | K | L | E | I | K R |
| k4 | . | . | . | . | . | . | . | . | . | P | H | T | F | G | Q | G | T | K | L | E | I | K R |
| l1 | . | . | . | . | . | . | . | . | . | A | V | L | F | G | G | G | T | K | L | T | V | L . |
| l2 | . | . | . | . | . | . | . | . | . | T | Y | V | F | G | P | G | T | K | V | E | I | K R |
| l3 | . | . | . | . | . | . | . | . | . | A | V | V | F | G | G | G | T | K | L | D | V | L . |
| l3 | . | . | . | . | . | . | . | . | . | I | W | V | F | G | G | G | T | K | L | T | V | L . |

FIG. 15

Statistics of subgroup-frequency of well-performing frameworks selected in the quality control system (% of total selected sequences

| VL domain | VL selected | VL random |
|---|---|---|
| VL κ1 | 52% | 46% |
| VL κ2 | 5% | 8% |
| VL κ3 | 5% | 17% |
| VL κ4 | 0 | 12.5% |
| VL λ1 | 19% | 4% |
| VL λ2 | 5% | 4% |
| VL λ3 | 14% | 8% |
| VH-domain | VH selected | VH random |
| VH 1b | 19% | 39% |
| VH 1a | 9% | 13% |
| VH 2 | 0 | 0 |
| VH 3 | 67% | 22% |
| VH 4 | 5% | 26% |
| VH 5 | 0 | 0% |
| VH 6 | 0 | 0% |

FIG. 16

| | VH- and VL-domain sequences used for the novel framework combinations | | |
|---|---|---|---|
| abb. | origin | sub-group | amino-acid sequence |
| 1.x | K I 27 | Vκ1 | EIVMTQSPSTLSASVGDRVIITCRASQSISSW LAWYQQKPGKAPKLLIYKASSLESGVPSRFS GSGSGAEFTLTISSLQPDDFATYYCQQYKSY WTFGQGTKLTVLG (Seq. Id. No. 1) |
| 2.x | K III25 | Vκ1 | EIVLTQSPSSLSASVGDRVTLTCRASQGIRNE LAWYQQRPGKAPKRLIYAGSILQSGVPSRFS GSGSGTEFTLTISSLQPEDVAVYYCQQYYSL PYMFGQGTKVDIKR (Seq. Id. No. 2) |
| 3.x | K IV103 | Vκ3 | EIVMTQSPATLSVSPGESAALSCRASQGVST NVAWYQQKPGQAPRLLIYGATIRASGVPA RFSGSGSGTEFTLTINSLQSEDFAAYYCQQY KHWPPWTFGQGTKVEIKR (Seq. Id. No. 3) |
| 4.x | K IV107 | Vλ1 | QSVLTQPPSVSAAPGQKVTISCSGSTSNIGDN YVSWYQQLPGTAPQLLIYDNTKRPSGIPDRF SGSKSGTSATLGITGLQTGDEADYYCGTWD SSLSGVVFGGGTKLTVLG (Seq. Id. No. 4) |
| 5.x | K IV135 | Vκ3 | EIVLTQSPATLSLSPGERATLSCRASQTLTHY LAWYQQKPGQAPRLLIYDTSKRATGVPARF SGSGSGTDFTLTISSLEPEDSALYYCQQRNS WPHTFGGGTKLHIKR (Seq. Id. No. 5) |
| 6.x | A43 | Vλ3 | SYVLTQPPSVSVAPGQTATVTCGGNNIGSKS VHWYQQKPGQAPVLVVYDDSDRPSGIPERF SGSNSGNTATLTIRRVEAGDEADYYCQVWD SSSDHNVFGSGTKVEIKR (Seq. Id. No. 6) |
| 7.x | A33 | Vλ3 | LPVLTQPPSVSVAPGQTARISCGGNNIETISV HWYQQKPGQAPVLVVSDDSVRPSGIPERFS GSNSGNTATLTISRVEAGDEADYYCQVWDS SSDYVFGGGTKLTVLG (Seq. Id. No. 7) |

FIG. 16
(continued)

| x.1 | A44 | VH3 | QVQLVQSGGGLVQPGGSLRLSCAASGFTF SSYAMSWVRQAPGKGLEWVSAISGSGGST YYADSVKGRFTISRDNSKNTLYLQMNSLR AEDTAVYYCAAHVLRFLEWLPDAFDIWG QGTLVTVSS (Seq. Id. No. 8) |
| --- | --- | --- | --- |
| x.2 | Afw10 | VH3 | EIVLTQSPSSLSASLGDRVTITCRASQSISSY LNWYQQKPGKAPKLLIYAASSSQSGVPSR FRGSESGTDFTLTISNLQPEDFATYYCQQS YRTPFTFGPGTKVEIKR (Seq. Id. No. 9) |
| x.3 | A33 | VH1b | VQLVQSGAEVKKPGASVKVSCTASGYSFT GYFLHWVRQAPGQGLEWMGRINPDSGDTI YAQKFQDRVTLTRDTSIGTVYMELTSLTSD DTAVYYCARVPRGTYLDPWDYFDYWGQ GTLVTVSS (Seq. Id. No. 10) |
| x.4 | A43 | VH3 | EVQLVESGGGLVQPGGSLRLSCAASGFTFS SYAMSWVRQAPGKGLEWVSAISGSGGST YYADSVKGRFTISRDNSKNTLYLQMNSLR AEDTAVYYCAKDAGIAVAGTGFDYWGQG TLVTVSS (Seq. Id. No. 11) |

SEQUENCE LISTING

<160> NUMBER OF SEQ ID NOS: 15

<210> SEQ ID NO 1
<211> LENGTH: 107
<212> TYPE: PRT
<213> ORGANISM: Artificial sequence
<220> FEATURE:
<223> OTHER INFORMATION: antibody framework

<400> SEQUENCE: 1

Glu Ile Val Met Thr Gln Ser Pro Ser Thr Leu Ser Ala Ser Val Gly
1               5                   10                  15

Asp Arg Val Ile Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Tyr Lys Ser Tyr Trp Thr
                85                  90                  95

Phe Gly Gln Gly Thr Lys Leu Thr Val Leu Gly
            100                 105

<210> SEQ ID NO 2
<211> LENGTH: 108
<212> TYPE: PRT
<213> ORGANISM: Artificial sequence
<220> FEATURE:
<223> OTHER INFORMATION: antibody framework

<400> SEQUENCE: 2

Glu Ile Val Leu Thr Gln Ser Pro Ser Ser Leu Ser Ala Ser Val Gly
1               5                   10                  15

Asp Arg Val Thr Leu Thr Cys Arg Ala Ser Gln Gly Ile Arg Asn Glu
            20                  25                  30

Leu Ala Trp Tyr Gln Gln Arg Pro Gly Lys Ala Pro Lys Arg Leu Ile
        35                  40                  45

Tyr Ala Gly Ser Ile Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Val Ala Val Tyr Tyr Cys Gln Gln Tyr Tyr Ser Leu Pro Tyr
                85                  90                  95

Met Phe Gly Gln Gly Thr Lys Val Asp Ile Lys Arg
            100                 105

<210> SEQ ID NO 3
<211> LENGTH: 109
<212> TYPE: PRT
<213> ORGANISM: Artificial sequence
<220> FEATURE:
<223> OTHER INFORMATION: antibody framework

<400> SEQUENCE: 3

Glu Ile Val Met Thr Gln Ser Pro Ala Thr Leu Ser Val Ser Pro Gly
1               5                   10                  15

Glu Ser Ala Ala Leu Ser Cys Arg Ala Ser Gln Gly Val Ser Thr Asn
            20                  25                  30

Val Ala Trp Tyr Gln Gln Lys Pro Gly Gln Ala Pro Arg Leu Leu Ile
        35                  40                  45

Tyr Gly Ala Thr Thr Arg Ala Ser Gly Val Pro Ala Arg Phe Ser Gly
    50                  55                  60

Ser Gly Ser Gly Thr Glu Phe Thr Leu Thr Ile Asn Ser Leu Gln Ser
65                  70                  75                  80

Glu Asp Phe Ala Ala Tyr Tyr Cys Gln Gln Tyr Lys His Trp Pro Pro
                85                  90                  95

Trp Thr Phe Gly Gln Gly Thr Lys Val Glu Ile Lys Arg
                100                 105

<210> SEQ ID NO 4
<211> LENGTH: 111
<212> TYPE: PRT
<213> ORGANISM: Artificial sequence
<220> FEATURE:
<223> OTHER INFORMATION: antibody framework

<400> SEQUENCE: 4

Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Asn Ile Gly Asp Asn
                20                  25                  30

Tyr Val Ser Trp Tyr Gln Gln Leu Pro Gly Thr Ala Pro Gln Leu Leu
        35                  40                  45

Ile Tyr Asp Asn Thr Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Val Val Phe Gly Gly Gly Thr Lys Leu Thr Val Leu Gly
                100                 105                 110

<210> SEQ ID NO 5
<211> LENGTH: 108
<212> TYPE: PRT
<213> ORGANISM: Artificial sequence
<220> FEATURE:
<223> OTHER INFORMATION: antibody framework

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Leu Thr His Tyr
                20                  25                  30

Leu Ala Trp Tyr Gln Gln Lys Pro Gly Gln Ala Pro Arg Leu Leu Ile
        35                  40                  45

Tyr Asp Thr Ser Lys Arg Ala Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ser Ala Leu Tyr Tyr Cys Gln Gln Arg Asn Ser Trp Pro His
                85                  90                  95

Thr Phe Gly Gly Gly Thr Lys Leu Glu Ile Lys Arg
                100                 105

<210> SEQ ID NO 6
<211> LENGTH: 109
<212> TYPE: PRT
<213> ORGANISM: Artificial sequence
<220> FEATURE:
<223> OTHER INFORMATION: Antibody framework

<400> SEQUENCE: 6

```
Ser Tyr Val Leu Thr Gln Pro Pro Ser Val Ser Val Ala Pro Gly Gln
1               5                   10                  15

Thr Ala Thr Val Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Arg Arg Val Glu Ala Gly
65                  70                  75                  80

Asp Glu Ala Asp Tyr Tyr Cys Gln Val Trp Asp Ser Ser Ser Asp His
                85                  90                  95

Asn Val Phe Gly Ser Gly Thr Lys Val Glu Ile Lys Arg
                100                 105
```

<210> SEQ ID NO 7
<211> LENGTH: 109
<212> TYPE: PRT
<213> ORGANISM: Artificial sequence
<220> FEATURE:
<223> OTHER INFORMATION: antibody framework

<400> SEQUENCE: 7

```
Leu Pro Val Leu Thr Gln Pro Pro Ser Val Ser Val Ala Pro Gly Gln
1               5                   10                  15

Thr Ala Arg Ile Ser Cys Gly Gly Asn Asn Ile Glu Thr Ile Ser Val
                20                  25                  30

His Trp Tyr Gln Gln Lys Pro Gly Gln Ala Pro Val Leu Val Val Ser
            35                  40                  45

Asp Asp Ser Val Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Val Val Phe Gly Gly Gly Thr Lys Leu Thr Val Leu Gly
                100                 105
```

<210> SEQ ID NO 8
<211> LENGTH: 124
<212> TYPE: PRT
<213> ORGANISM: Artificial sequence
<220> FEATURE:
<223> OTHER INFORMATION: antibody framework

<400> SEQUENCE: 8

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45
```

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala His Val Leu Arg Phe Leu Glu Trp Leu Pro Asp Ala Phe Asp
            100                 105                 110

Ile Trp Gly Gln Gly Thr Leu Val Thr Val Ser Ser
            115                 120

<210> SEQ ID NO 9
<211> LENGTH: 108
<212> TYPE: PRT
<213> ORGANISM: Artificial sequence
<220> FEATURE:
<223> OTHER INFORMATION: antibody framework

<400> SEQUENCE: 9

Glu Ile Val Leu Thr Gln Ser Pro Ser Ser Leu Ser Ala Ser Leu Gly
1               5                   10                  15

Asp Arg Val Thr Ile Thr Cys Arg Ala Ser Gln Ser Ile Ser Ser Tyr
            20                  25                  30

Leu Asn Trp Tyr Gln Lys Pro Gly Lys Ala Pro Lys Leu Leu Ile
        35                  40                  45

Tyr Ala Ala Ser Ser Ser Gln Ser Gly Val Pro Ser Arg Phe Arg Gly
    50                  55                  60

Ser Glu Ser Gly Thr Asp Phe Thr Leu Thr Ile Ser Asn Leu Gln Pro
65                  70                  75                  80

Glu Asp Phe Ala Thr Tyr Tyr Cys Gln Gln Ser Tyr Arg Thr Pro Phe
                85                  90                  95

Thr Phe Gly Pro Gly Thr Lys Val Glu Ile Lys Arg
            100                 105

<210> SEQ ID NO 10
<211> LENGTH: 123
<212> TYPE: PRT
<213> ORGANISM: Artificial sequence
<220> FEATURE:
<223> OTHER INFORMATION: antibody framework

<400> SEQUENCE: 10

Val Gln Leu Val Gln Ser Gly Ala Glu Val Lys Lys Pro Gly Ala Ser
1               5                   10                  15

Val Lys Val Ser Cys Thr Ala Ser Gly Tyr Ser Phe Thr Gly Tyr Phe
            20                  25                  30

Leu His Trp Val Arg Gln Ala Pro Gly Gln Gly Leu Glu Trp Met Gly
        35                  40                  45

Arg Ile Asn Pro Asp Ser Gly Asp Thr Ile Tyr Ala Gln Lys Phe Gln
    50                  55                  60

Asp Arg Val Thr Leu Thr Arg Asp Thr Ser Ile Gly Thr Val Tyr Met
65                  70                  75                  80

Glu Leu Thr Ser Leu Thr Ser Asp Asp Thr Ala Val Tyr Tyr Cys Ala
                85                  90                  95

Arg Val Pro Arg Gly Thr Tyr Leu Asp Pro Trp Asp Tyr Phe Asp Tyr
            100                 105                 110

Trp Gly Gln Gly Thr Leu Val Thr Val Ser Ser

<210> SEQ ID NO 11
<211> LENGTH: 122
<212> TYPE: PRT
<213> ORGANISM: Artificial sequence
<220> FEATURE:
<223> OTHER INFORMATION: antibody framework

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ala Gly Ile Ala Val Ala Gly Thr Gly Phe Asp Tyr Trp
            100                 105                 110

Gly Gln Gly Thr Leu Val Thr Val Ser Ser
            115                 120

<210> SEQ ID NO 12
<211> LENGTH: 28
<212> TYPE: DNA
<213> ORGANISM: Artificial sequence
<220> FEATURE:
<223> OTHER INFORMATION: PCR Primer

<400> SEQUENCE: 12
tgctctagaa gtgctgcagt gactgcag                                        28

<210> SEQ ID NO 13
<211> LENGTH: 33
<212> TYPE: DNA
<213> ORGANISM: Artificial sequence
<220> FEATURE:
<223> OTHER INFORMATION: PCR Primer

<400> SEQUENCE: 13
ggttgtcgac ttacaggctg ctgggagcaa tcg                                  33

<210> SEQ ID NO 14
<211> LENGTH: 122
<212> TYPE: PRT
<213> ORGANISM: Artificial Sequence
<220> FEATURE:
<223> OTHER INFORMATION: Consensus sequence

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

```
Gly Gly Ile Ile Pro Ile Phe Gly Thr Ala Ala Asn Tyr Ala Gln Lys
        50              55                  60

Phe Gln Gly Arg Val Thr Ile Thr Ala Asp Glu Ser Thr Ser Thr Ala
65              70                  75                  80

Tyr Met Glu Leu Ser Ser Leu Arg Ser Glu Ala Asp Thr Ala Val Tyr
                85                  90                  95

Tyr Cys Ala Arg Trp Gly Gly Asp Gly Phe Tyr Ala Met Asp Tyr Trp
                100             105                 110

Gly Gln Gly Thr Leu Val Thr Val Ser Ser
        115                 120

<210> SEQ ID NO 15
<211> LENGTH: 122
<212> TYPE: PRT
<213> ORGANISM: Artificial Sequence
<220> FEATURE:
<223> OTHER INFORMATION: Consensus sequence

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
                35                  40                  45

Gly Trp Ile Asn Pro Asn Ser Gly Gly Thr Asx Asn Tyr Ala Gln Lys
        50              55                  60

Phe Gln Gly Arg Val Thr Met Thr Arg Asp Thr Ser Ile Ser Thr Ala
65              70                  75                  80

Tyr Met Glu Leu Ser Ser Leu Arg Ser Glu Asx Asp Thr Ala Val Tyr
                85                  90                  95

Tyr Cys Ala Arg Trp Gly Gly Asp Gly Phe Tyr Ala Met Asp Tyr Trp
                100             105                 110

Gly Gln Gly Thr Leu Val Thr Val Ser Ser
        115                 120
```

IMMUNOGLOBULIN FRAMEWORKS WHICH DEMONSTRATE ENHANCED STABILITY IN THE INTRACELLULAR ENVIRONMENT AND METHODS OF IDENTIFYING SAME

CROSS REFERENCE TO RELATED APPLICATION

This application is a divisional of U.S. patent application Ser. No. 15/340,195 filed Nov. 1, 2016 that issued as U.S. Pat. No. 10,125,186 on Nov. 13, 2018, that is a divisional of U.S. patent application Ser. No. 14/469,276 filed Aug. 26, 2014 that issued as U.S. Pat. No. 9,518,108 on Dec. 13, 2016, that is a divisional of U.S. patent application Ser. No. 10/515,241, filed Jul. 18, 2005 that issued as U.S. Pat. No. 8,853,362 on Oct. 7, 2014, which is a 371 National Stage Entry of International Application Serial No. PCT/EP03/05324, filed May 21, 2003 (now pending) which claims priority to U.S. Provisional Patent Application Ser. No. 60/438,256 filed Jan. 3, 2003, and U.S. Provisional Patent Application Ser. No. 60/382,649, filed May 22, 2002, the entire contents of which are incorporated herein by reference.

FIELD OF THE INVENTION

The invention relates to protein chemistry, molecular biology, and immunology.

BACKGROUND OF THE RELATED ART

Antibodies can recognize and target almost any molecule with high specificity and affinity. This characteristic has been exploited to turn these natural proteins into powerful tools for diagnostic and therapeutic applications. Advances in recombinant DNA technology have facilitated the manipulation, cloning, and expression of antibody genes in a wide variety of non-lymphoid cells (Skerra, 1988; Martineau, 1998; Verma, 1998). A number of different antibody fragments have been constructed to best suit the various applications. The smallest entity that retains the full antigen-binding capacity of the whole parental immunoglobulin is the single-chain Fv fragment (scFv) (Bird, 1988). This antibody fragment comprises the variable regions of the heavy and the light chains linked by a flexible peptide-linker, which allows the expression of the protein from a single gene.

Antibody fragments have several important advantages in comparison to the entire immunoglobulin molecule. Due to their smaller size, the expression is facilitated and the yield is enhanced in a variety of expression host cells, such as *E. coli* cells (Plückthun, 1996). Moreover, antibody fragments allow improved tumour penetration in in vivo applications (Yokota, 1992) and they can be linked covalently to various effector molecules for therapeutic approaches.

Naturally occurring antibodies, which are secreted by plasma cells, have evolved to function in an extracellular, oxidizing environment. To obtain their functional, folded structure, they generally require the formation of disulfide-bridges within the separate domains, which are crucial for the stability of the immunoglobulin fold. In contrast to full-length antibodies, scFv or Fab antibody fragments can, in principle, be functionally expressed in a reducing environment inside any cell and directed to any compartment to target intracellular proteins and thus evoke specific biological effects (Biocca, 1991). Indeed, some intracellular single chain antibody fragments, which are called intrabodies, have been applied successfully to modulate the function of intracellular target proteins in different biological systems. Thus, resistance against viral infections has been demonstrated in plant biotechnology (Tavladoraki, 1993; Benvenuto, 1995), binding of intrabodies to HIV proteins has been shown (Rondon, 1997), and binding to oncogene products (Biocca, 1993; Cochet, 1998; Lener, 2000) has been described. Moreover, intracellular antibodies promise to be a valuable tool in characterizing the function of a vast number of genes now identified through the sequencing of the human genome (Richardson, 1995; Marasco, 1997). For example, they can be used in a functional genomics approach to block or modulate the activity of newly identified proteins, thereby contributing to the understanding of their functions. Finally, intrabodies have potential diagnostic and therapeutic applications, for example in gene therapy settings.

Despite these great prospects, the generation of functional intrabodies is still limited by their instability and insolubility or propensity to aggregate. The reducing environment of the cytoplasm prevents the formation of the conserved intrachain disulfide bridges, thus rendering a high percentage of antibody fragments unstable and, as a consequence, non-functional inside the cell (Biocca, 1995; Proba, 1997). Stability and solubility of antibody fragments therefore represents a major obstacle for the application of intrabodies as potential modulators of protein function in vivo. So far, no predictions can be made about the sequence requirements that render an antibody fragment functional in an intracellular environment.

There is, therefore, a need for antibody fragments which perform well in a broad range of different cell types and can thus be used as frameworks for diverse binding specificities. Such frameworks can be used to construct libraries for intracellular screening or can serve as an acceptor for the binding portions of an existing antibody.

Besides being uniquely suited for intracellular applications, such antibody fragments or whole antibodies based on very stable variable domain frameworks also have a distinct advantage over other antibodies in numerous extracellular and in vitro applications. When such frameworks are produced in an oxidizing environment, their disulfide-bridges can be formed, further enhancing their stability and making them highly resistant towards aggregation and protease degradation. The in vivo half-life (and thus the resistance towards aggregation and degradation by serum proteases) is, besides affinity and specificity, the single-most important factor for the success of antibodies in therapeutic or diagnostic applications (Willuda, 1999). The half-life of antibody fragments can further be increased through the covalent attachment of polymer molecules such as poly-ethylene glycol (PEG) (Weir, 2002). Stable molecules of this type represent a significant advance in the use of antibodies, especially, but not exclusively, when the Fc functionality is not desired.

The great practical importance of antibody-fragment libraries has motivated research in this area. Winter (EP 0368684) has provided the initial cloning and expression of antibody variable region genes. Starting from these genes he has created large antibody libraries having high diversity in both the complementary determining regions (CDRs) as well as in the framework regions. Winter does not disclose, however, the usefulness of different frameworks for library construction.

The teaching of Plückthun (EP 0859841), on the other hand, has tried to improve the library design by limiting the frameworks to a defined number of synthetic consensus sequences. Protein engineering efforts involving introduction of a large amount of rationally designed mutations have previously suggested mutations towards the respective consensus sequence as a suitable means for the improvement of the stability of isolated variable immunoglobulin domains (Ohage 1999; Ohage 1999 and U.S. Pat. No. 5,854,027, hereby incorporated by reference).

Plückthun (EP 0859841) discloses methods for the further optimization of binding affinities based on these consensus sequences. The Plückthun patent also acknowledges the ongoing increase in knowledge concerning antibodies and accordingly aims at including such future findings in the library design. However, no possible further improvements of the synthetic consensus frameworks are suggested.

The teachings of Winter, Plückthun and others (e.g. Soderlind, WO 0175091) have thus tried to create large antibody libraries with a focus on high diversity in the CDRs for selection and application of the selected scFvs under oxidizing conditions. All of these libraries are, however, not optimized for intracellular applications and thus not useful for selection and applications in a reducing environment, or other conditions which set special requirements on stability and solubility of the expressed antibody fragment.

The qualities required for antibody fragments to perform well in a reducing environment, e.g. the cytoplasm of prokaryotic and eukaryotic cells, are not clear. The application of intracellular antibodies or "intrabodies" is therefore currently limited by their unpredictable behavior under reducing conditions, which can affect their stability and solubility properties (Biocca, 1995; Wörn, 2000). Present patent applications (EP1040201, EP1166121 and WO0200729) and publications (Visintin, 1999) concerning intracellular screening for intrabodies focus on the screening technology but do not disclose specific antibody sequences which are functional in eukaryotic cells, in particular in yeast, and, thus, useful for library construction in this context.

Visintin and Tse have independently described the isolation of a so-called intracellular consensus sequence (ICS) (Visintin, 2002; Tse, 2002). This sequence was derived from a number of sequences that had been isolated from an antigen-antibody-interaction screen in yeast. The input into the intracellular screen was, however, heavily biased due to prior phage-display selection. Thus, all but one of the input-sequences belonged to the VH 3 subgroup in the case of Visintin et al. The published consensus sequence ICS is fully identical to the consensus sequence for the human VH 3 subgroup described by Knappik (2000) and EP0859841. 60 of the 62 amino acids of the ICS are also identical to the general human VH-domain consensus sequence which was proposed by Steipe as a basis for the construction of variable domains with enhanced stability (U.S. Pat. No. 6,262,238, hereby incorporated by reference). These works were, in turn, based on earlier sequence collections (i.e., Kabat, 1991 and definitions of variable domain subgroups and structural determinants (Tomlinson, 1992; Williams, 1996; Chothia, 1989 and Chothia, 1987). However, because the input to the intrabody selection was so heavily biased (i.e., in the case of Visintin et al. all but one of the VH domains was VH3), the isolation of VH3 sequences from intracellular screening is not particularly surprising. Due to the heavy bias of their input library, the work of Tse et al. and Visintin et al. does not provide a thorough evaluation of the human variable domain repertoire as would be provided by an unbiased inquiry and as is required to identify the useful intrabody frameworks present in the human repertoire.

We have previously described a system, which allows for the selection of stable and soluble intrabodies in yeast, independent of their antigen-binding specificity (Auf der Maur (2001), WO0148017). This approach allows efficient screening of scFv libraries and the isolation of specific frameworks, which are stable and soluble in the reducing environment of the yeast cell. The objective remains to actually isolate framework sequences and use the patterns in a first step to predict what sequence types would be most stable in the reducing environment and in a second step identify by analysis, recombination and further in vivo and in vitro experiments the optimal sequence.

BRIEF SUMMARY OF THE INVENTION

The present invention fills a missing link in the field of antibody generation. It provides antibody variable domain framework sequences with superior characteristics regarding stability and solubility. These are crucial features for many relevant applications, such as in diagnostics, therapy or research. These frameworks can be used for grafting of existing binding-specificities or for the generation of antibody libraries with high stability and solubility.

ScFv libraries were used for the isolation of frameworks which are stable and soluble in the reducing environment of the yeast cell. The performance of the isolated frameworks has subsequently been characterized in human cell lines and in in vitro experiments. The described frameworks can directly serve as acceptor backbones for existing binding specificities or to construct CDR libraries by randomization of one or more of the hypervariable loops for use in reducing or otherwise challenging environments. The isolated variable domain sequences have further been analyzed by alignment to identify preferred sequence families. From those preferred variable domain sequence families, optimal sequences were chosen based on a structural analysis which excludes sequences containing framework residues which disturb the immunoglobulin fold. The identified variable domain sequence candidates were subsequently recombined in all possible variations and the optimal combinations of variable domains of the light and heavy chain were selected by analysis of their performance in yeast, mammalian cells and in vitro.

These optimized scFvs and their constituting variable domain frameworks, as well as other antibody fragments or whole antibodies derived thereof, are ideal as, for example, acceptor backbones for existing binding specificities or for the construction of CDR libraries by randomization of one or more of the hypervariable loops for use in reducing or otherwise challenging environments. Antibodies suitable for intracellular applications are by definition more stable and soluble. Accordingly, their use will also be advantageous in applications outside the intracellular environment.

The invention provides compositions comprising frameworks of antibody variable domains and single-chain Fv antibody (ScFv) fragments which can be incorporated into various antibody fragments or whole antibodies. Classes of antibody variable domains fragments are provided which are the most stable and soluble and thus best suited for intracellular applications. Specific framework sequences of antibody variable domains and scFv antibody fragments which show the highest performance in intracellular assays are also provided. The invention also provides specific framework sequences of antibody variable domains and synthetic combinations of variable domains of the light and heavy chain in scFv fragments which are, for example, optimal for intracellular applications and show an optimal performance in vitro regarding stability and solubility.

The invention provides single-chain framework reagents that have the general structures:

NH$_2$-VL-linker-VH-COOH or
NH$_2$-VH-linker-VL-COOH.

In another embodiment of the invention the single-chain framework may be fused to a second protein moiety to yield a fusion construct of the general structure:

NH$_2$-VL-linker-VH-second protein-COOH
NH$_2$-second protein-VL-linker-VH-COOH.

The orientation of the VH and VL regions in these fusion constructs may be reversed.

In another embodiment of the invention the variable domains may be incorporated into a Fab fragment, which may additionally be fused to a second protein moiety to yield fusion constructs of the general structure:

NH$_2$-VH-CH-second protein-COOH and NH$_2$-VL-CL-COOH

The second protein may be fused to either N or C-terminus of either the heavy or the light chain.

In a preferred embodiment, the second protein of the single-chain or Fab framework fusion construct is a protein which provides a read-out for intracellular assays, either directly or via transcriptional activation.

Another object of the invention is to provide framework classes of antibody variable domains and sequences of variable domains and scFvs which are suitable for grafting the hypervariable loops from existing antibodies, for example, in order to obtain antibodies which are functional in a reducing or otherwise challenging environment.

Another object of the invention is to provide framework classes of antibody variable domains and sequences of variable domains and scFvs which, for example, through randomization of one or more of the hypervariable loops of such frameworks, are suitable for the creation of libraries for use in a reducing or otherwise challenging environment.

Another object of the invention is the use of the disclosed sequences in the identification of conserved residues and consensus sequences.

The antibodies or antibody fragments resulting from the use of the disclosed frameworks can be used as reagents in target validation and in therapy, prevention and diagnosis of human, animal and plant diseases. The antibodies can be used in the form of protein or DNA encoding such a protein and are not limited to intracellular applications.

BRIEF DESCRIPTION OF THE DRAWINGS

FIG. 12 shows an alignment of all VH-domain framework sequences selected from various "quality control" screens in yeast.

FIG. 13 shows an alignment of all VL-domain framework sequences selected from various "quality control" screens in yeast.

FIG. 14 shows an alignment of randomly picked sequences from the library.

FIG. 15 shows a statistical analysis of the sub-class frequency for VH- and VL-domains in the sequences isolated with the "quality control" system. Only those sequences were considered which were subsequently found to be positive in the quantitative yeast assay. The selected sequences are compared with the unselected library as determined from a limited number of random sequences (FIG. 14).

FIG. 16 shows the sequences used for further recombination and evaluation of the best combinations in scFvs and their respective abbreviations (abb.), sources and sub-family.

DETAILED DESCRIPTION OF THE INVENTION

Figure 1:
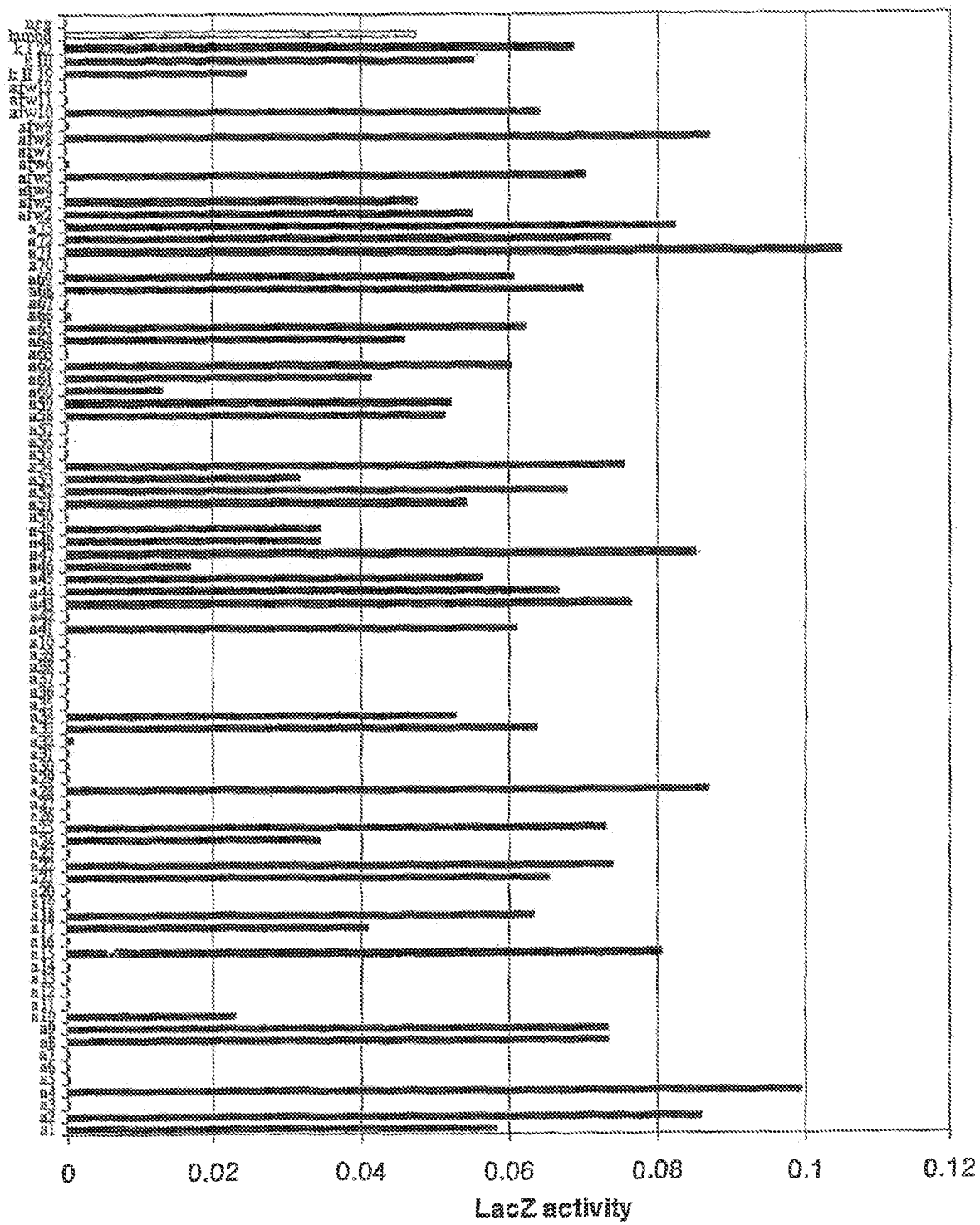
FIG. 1 shows the result of a typical "quality control" screen in yeast assayed by activation of lacZ expression (see, for example, Example 1). The selected, positive clones (black) were identified in several different screens and the corresponding sequences of the positive clones can be found in FIGS. 12 and 13. The selected sequences are compared to the positive control, the very stable lambda-graft (dark grey).

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

As used herein, "identity" refers to the sequence similarity between two polypeptides, molecules or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are homologous at that position. The "percentage identity" between two sequences is a function of the number of matching positions shared by the two sequences divided by the number of positions compared ×100. For instance, if 6 of 10 of the positions in two sequences are matched, then the two sequences have 60% identity. By way of example, the DNA sequences CTGACT and CAGGTT share 50% homology (3 of the 6 total positions are matched). Generally, a comparison is made when two sequences are aligned to give maximum homology. Such alignment can be provided using, for instance, the method of Needleman et al., J. Mol Biol. 48: 443-453 (1970), implemented conveniently by computer programs such as the Align program (DNAstar, Inc.).

"Similar" sequences are those which, when aligned, share identical and similar amino acid residues, where similar residues are conservative substitutions for, or "allowed point mutations" of, corresponding amino acid residues in an aligned reference sequence. In this regard, a "conservative substitution" of a residue in a reference sequence is a substitution by a residue that is physically or functionally similar to the corresponding reference residue, e.g., that has a similar size, shape, electric charge, chemical properties, including the ability to form covalent or hydrogen bonds, or the like. Thus, a "conservative substitution modified" sequence is one that differs from a reference sequence or a wild-type sequence in that one or more conservative substitutions or allowed point mutations are present. The "percentage positive" between two sequences is a function of the number of positions that contain matching residues or conservative substitutions shared by the two sequences divided by the number of positions compared ×100. For instance, if 6 of 10 of the positions in two sequences are matched and 2 of 10 positions contain conservative substitutions, then the two sequences have 80% positive homology.

"VH domain" refers to the variable part of the heavy chain of an immunoglobulin molecule.

"VL domain" refers to the variable part of the light chain of an immunoglobulin molecule.

VH or VL "subtype" refers to the subtype defined by the respective consensus sequence as defined in Knappik (2000). The term "subfamily" or "subclass" is used as synonym for "subtype". The term "subtype" as used herein refers to sequences sharing a high degree of identity and similarity with the respective consensus sequence representing their subtype. Whether a certain variable domain sequence belongs to a "subtype" is determined by alignment of the sequence with either all known human germline segments of the respective domain, or the defined consensus sequences and subsequent identification of the greatest homology. Methods for determining homologies and grouping of sequences by using search matrices, such as BLOSUM (Henikoff 1992) are well known to the person skilled in the art.

"Amino acid consensus sequence" as used herein refers to an amino acid sequence, which can be generated using a matrix of at least two or preferably more aligned amino acid sequences, and allowing for gaps in the alignment, it is possible to determine the most frequent amino acid residue at each position. The consensus sequence is that sequence which comprises the amino acids which are most frequently represented at each position. In the event that two or more amino acids are equally represented at a single position, the consensus sequence includes both or all of those amino acids.

The amino acid sequence of a protein can be analyzed at various levels. For example, conservation or variability could be exhibited at the single residue level, multiple residue level, multiple residue with gaps etc. Residues could exhibit conservation of the identical residue or could be conserved at the class level. Examples of amino acid classes include polar but uncharged R groups (Serine, Threonine, Asparagine and Glutamine); positively charged R groups (Lysine, Arginine, and Histidine); negatively charged R groups (Glutamic acid and Aspartic acid); hydrophobic R groups (Alanine, Isoleucine, Leucine, Methionine, Phenylalanine, Tryptophan, Valine and Tyrosine); and special amino acids (Cysteine, Glycine and Proline). Other classes are known to one of skill in the art and may be defined using structural determinations or other data to assess substitutability. In that sense a substitutable amino acid could refer to any amino acid which could be substituted and maintain functional conservation at that position.

"Polynucleotide consensus sequence" as used herein refers to a nucleotide sequence, which can be generated using a matrix of at least two or preferably more aligned nucleic acid sequences, and allowing for gaps in the alignment, it is possible to determine the most frequent nucleotide at each position. The consensus sequence is that sequence which comprises the nucleotides which are most frequently represented at each position. In the event that two or more nucleotides are equally represented at a single position, the consensus sequence includes both or all of those nucleotides.

"Structural sub-element" as used herein refers to stretches of amino acid residues within a protein or polypeptide that correspond to a defined structural or functional part of the molecule. These can be loops (i.e. CDR loops of an antibody) or any other secondary or functional structure within the protein or polypeptide (i.e., domains, α-helices, β-sheets, framework regions of antibodies, etc.). A structural sub-element can be identified using known structures of similar or homologous polypeptides, or by using the above mentioned matrices of aligned amino acid sequences. Here the variability at each position is the basis for determining stretches of amino acid residues which belong to a structural sub-element (e.g. hypervariable regions of an antibody).

"Sub-sequence" as used herein refers to a genetic module which encodes at least one structural sub-element. It is not necessarily identical to a structural sub-element.

"Antibody CDR" as used herein refers to the complementarity determining regions of the antibody which consist of the antigen binding loops as defined by Kabat et al. (1991). Each of the two variable domains of an antibody Fv fragment contain, for example, three CDRs.

"Antibody" as used herein is a synonym for "immunoglobulin". Antibodies according to the present invention may be whole immunoglobulins or fragments thereof, comprising at least one variable domain of an immunoglobulin, such as single variable domains, Fv (Skerra, 1988), scFv (Bird, 1988; Huston, 1988), Fab, (Fab')2 or other fragments well known to a person skilled in the art.

"Antibody framework" as used herein refers to the part of the variable domain, either VL or VH, which serves as a scaffold for the antigen binding loops of this variable domain (Kabat et al., 1991).

Figure 8A:
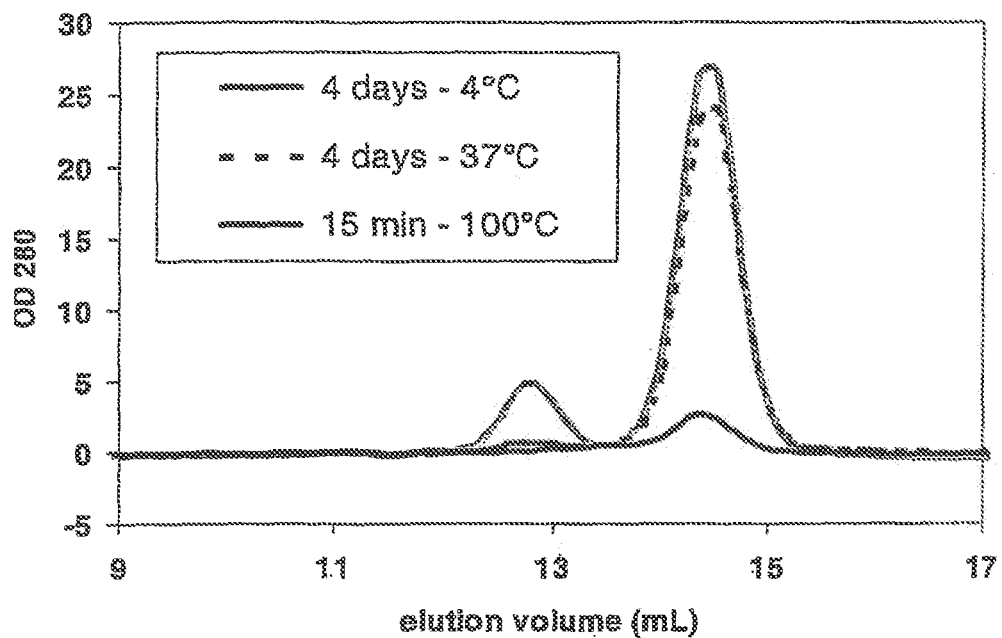
FIG. 8A represents the resistance towards aggregation at 37° C. of selected framework combinations (for frameworks 2.4 and 5.2) as quantified by the amount of monomeric protein present before and after incubation as indicated in PBS-buffer.
Figure 8B:
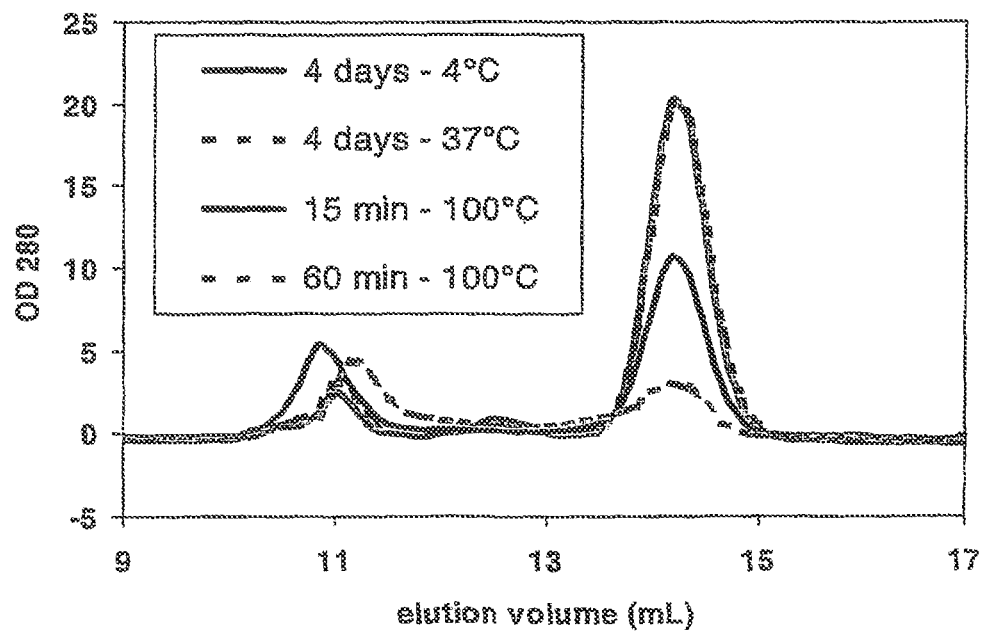
FIG. 8B represents the resistance towards aggregation at 37° C. of selected framework combinations (for frameworks 4.4, 6.4 and 7.3) as quantified by the amount of monomeric protein present before and after incubation as indicated in PBS-buffer.
Figure 9:
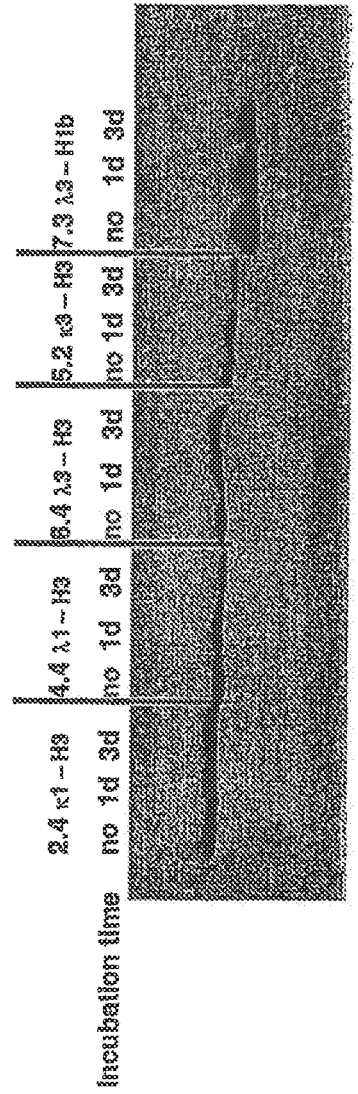
FIG. 9 represents the resistance towards protease degradation aggregation in human serum at 37° C. of selected framework combinations, quantified by the amount of soluble full-length protein present before and after prolonged incubation.
Figure 10:
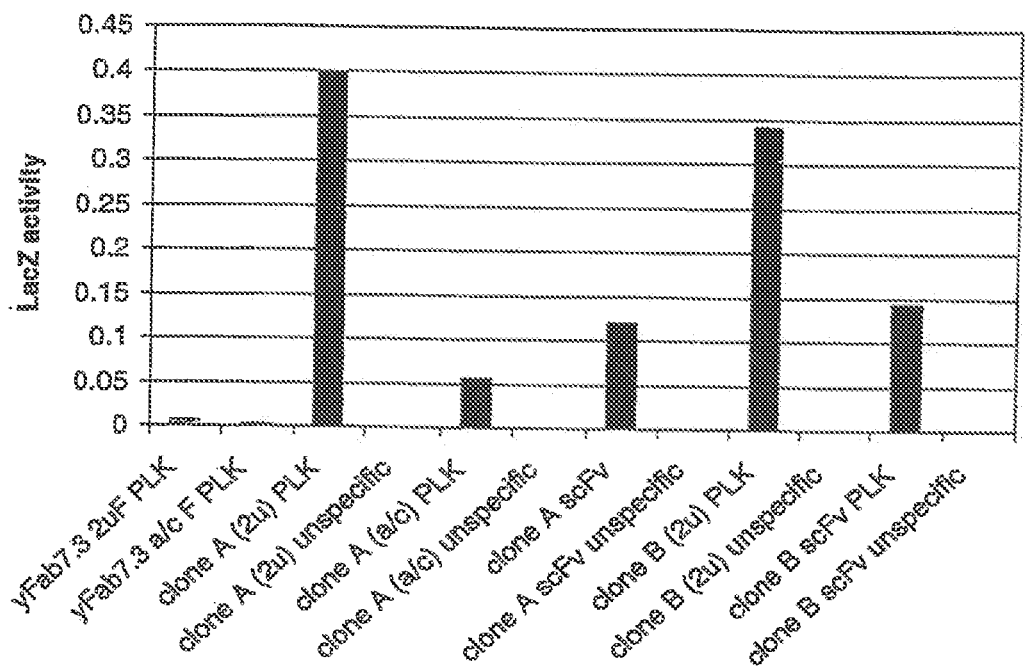
FIG. 10 shows the in vivo performance of two selected binders on the novel framework 7.3 in the Fab-context, assayed in yeast interaction assay by the activation of lacZ expression. Expression of the Fab-chains is from a bi-directional galactose-inducible promoter, on either an ars/cen or a 2 micron vectors. Expression from the Fab vector yields the antibody light chain and a VH-CH1-Gal4-AD fusion protein. Binders are directed against human Polo-like kinase1 (hPLK1). Binding to the target is compared with the unspecific binding to an unrelated antigen and the binding of the un-randomized framework 7.3. Note that the corresponding scFv that have been included for reference are expressed from an actin promoter (2 micron).

Rationally engineered scFv fragments have demonstrated a clear correlation between the thermodynamic stability of a scFv fragment and its in vivo performance (Wörn, 2000; Auf der Maur, 2001). Using a recently developed system named "Quality Control" (Auf der Maur, 2001), specific antibody variable domain framework sequences which are suitable for intracellular applications have been isolated (FIGS. 12 and 13), characterized (FIGS. 1 and 2) and further improved (FIGS. 3 to 9 and FIG. 14). As observed in our previous experiments, well performing frameworks selected in the intracellular assay show a high in vitro stability as demonstrated by their resistance to aggregation and protease degradation at 37° C. (FIGS. 8 and 9). Moreover, a pattern emerged which allows a selection of frameworks for intracellular applications on a more general basis, depending on their framework subfamily (FIG. 15). Specific antibody variable domain sequences useful for intracellular applications are disclosed here, as well as the general pattern. This allows, on the one hand, the use of these sequences as framework donors in grafting experiments to obtain functional intrabodies which retain the binding specificity of the loop donor. Additionally, antibody libraries can be constructed using the disclosed sequences as frameworks. Such libraries are suitable for intracellular selection systems under reducing conditions, such as those in prokaryotic and eukaryotic cells. Additionally, the disclosed sequences may be used to identify, for example, conserved sequences or residues or motifs. The grafting of structural sub-elements, for example, those of the binding loops of an antibody (e.g. Jung, 1997), as well as the making of libraries of antibodies or fragments thereof (e.g. Vaughan, 1996; Knappik, 2000) has been described in detail and is well known to a person skilled in the art.

Because intracellular applications expose the antibody fragments to very unfavorable conditions (i.e. increased temperatures, reducing environment), the sequences disclosed in the present invention have acquired features that make them resistant to the most adverse conditions. Therefore, when compared to "average" sequences, the disclosed sequences are of outstanding stability and solubility as is demonstrated by their resistance towards aggregation and protease degradation (FIGS. 8 and 9). These features, together with their excellent expression yield make the disclosed antibody framework sequences uniquely suitable not only for intracellular use, but especially for all therapeutic and diagnostic applications where long half-life, robustness, and ease of production are of great concern.

Figure 2:
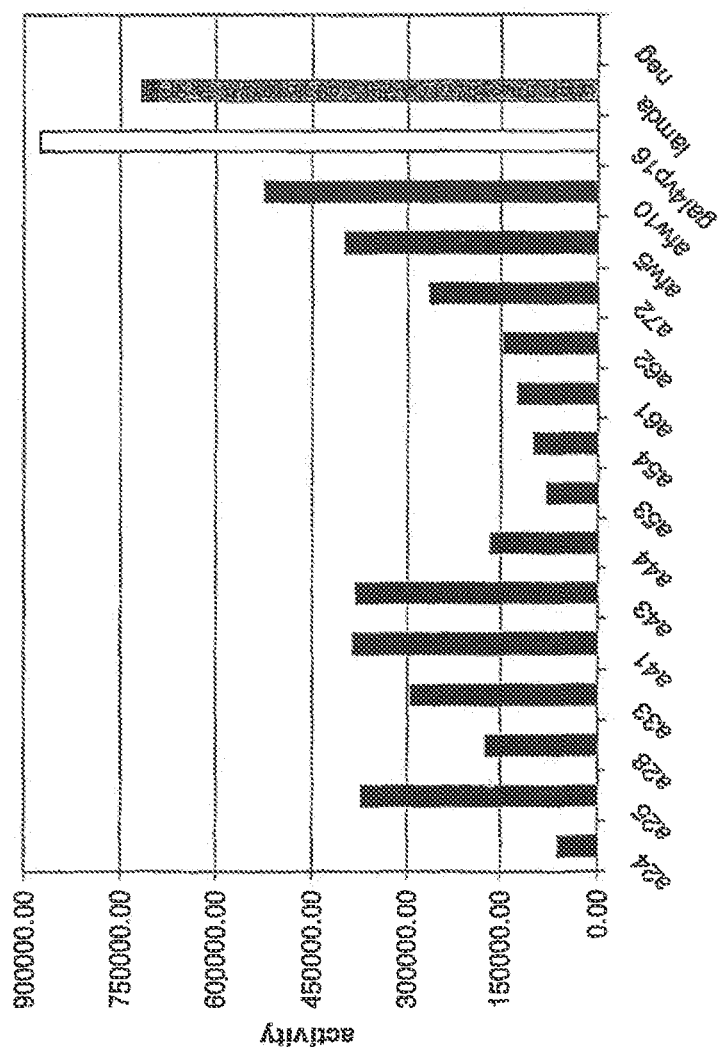
FIG. 2 shows the performance of the frameworks isolated from a typical "quality control" screen in yeast (black) in the human cell line Hela, assayed by the activation of luciferase expression in comparison to the very stable lambda-graft (dark grey). The positive control Gal4-VP16 (white) gives the maximally possible level of transcriptional activation in the system. Luciferase activity has been corrected for transfection efficiency.

The present invention enables the design of polypeptide sequences comprising at least the variable part of an antibody that are useful for applications in a reducing or otherwise challenging environment. In a first embodiment, the invention provides a collection of antibody framework sequences useful for intracellular applications (FIGS. 12 and 13). In a first step, a library of diverse sequences is screened independent of binding affinity using the Quality control system in yeast. The isolated sequences can be evaluated for their intracellular performance in yeast and in mammalian cells (FIGS. 1 and 2).

In one embodiment of the invention, the collection of isolated sequences is analyzed by alignment to identify the antibody variable domain sub-classes and consensus sequences that are suitable for intracellular applications.

In a further preferred embodiment of the invention, the collection of antibody framework sequences described above is further analyzed by alignment to each other and grouping into sub-families. All frameworks belonging to one sub-type are compared regarding their intracellular performance in yeast and in mammalian cells (FIGS. 1 and 2, as an example) and regarding the occurrence of negative, neutral or positive exchanges in their amino-acid sequence relative to the respective sub-type consensus. A person skilled in the art can distinguish between positive, neutral and negative changes based on the structural environment of the particular exchanged residue in the immunoglobulin domain. Subsequently, framework sequences of variable antibody domains are chosen which show the best intracellular performance and which are devoid of negative exchanges compared to their respective sub-type consensus. Preferably, sequences are selected which further contain amino-acid exchanges which are considered positive.

In a further preferred embodiment, the selected antibody variable domains of the heavy and the light chain are subsequently recombined in all possible combinations into scFv fragments, in order to identify the combinations with the highest stability and solubility. To this end the novel, recombined scFv fragments are evaluated for their performance under reducing conditions in intracellular interaction assays in yeast (FIG. 3) and in mammalian cell lines (FIGS. 4 and 7) and for soluble intracellular expression in yeast (FIG. 5). Promising combinations are further evaluated for their behavior under oxidizing conditions by analyzing the periplasmic expression yield in E. coli (FIG. 6), the resistance to aggregation at elevated temperatures (FIG. 8) and the resistance to aggregation and protease degradation upon prolonged incubation in human serum at 37° C. (FIG. 9).

These data are used to identify the scFv framework best suitable for any specific application, either intracellular, or under oxidizing conditions.

The selected and optimized framework sequences disclosed herein have a significant advantage not only in intracellular applications, but in all applications which can profit from increased stability and/or solubility of the scFv. Examples are the long-term storage at high concentrations required for diagnostic applications, and prolonged functional half-life in serum at 37° C. (as required, for example, in therapeutic applications).

According to one aspect of the present invention, there is provided an intrabody framework comprising a single-chain framework having the general structure:

NH$_2$-VL-linker-VH-COOH; or
NH$_2$-VH-linker-VL-COOH wherein the VH framework is of subtype 1a, 1b or 3.

In another embodiment, the orientation of the VH and VL regions is reversed in the single chain framework described above.

According to one aspect of the present invention, there is provided an intrabody framework comprising a single-chain framework having the general structure:

NH$_2$-VL-linker-VH-COOH; or
NH$_2$-VH-linker-VL-COOH wherein the VH framework is of subtype 1a, 1b or 3 and the VL framework is of subtype λ1, λ3 or κ1.

In another embodiment, the invention provides a single-chain framework fused to a second protein moiety to yield a fusion construct of the general structure:

NH$_2$-VL-linker-VH-second protein-COOH; or
NH$_2$-second protein-VL-linker-VH-COOH wherein the VH framework is of subtype 1a, 1b or 3 and the VL framework is of subtype λ1, λ3 or κ1.

In another embodiment, the orientation of the VH and VL regions in these fusion constructs may be reversed.

In another embodiment, the variable domains may be incorporated into a Fab fragment which may additionally be fused to a second protein moiety to yield fusion constructs of the general structure:

NH$_2$-VH-CH-second protein-COOH and NH$_2$-VL-CL-COOH

The second protein may be fused to either N or C-terminus of either the heavy or the light chain.

As disclosed herein, there is a very strong preference in intracellular applications for VH framework of the subtype 3, but also for 1a and 1b. Regarding the light chain variable domain (VL), there is a clear preference by numbers for frameworks of the kappa 1 type, but lambda 1 and 3 are also enriched. These framework sub-types, i.e. VH 1a, 1b and 3 combined with a kappa 1, lambda for 3 VL domain are therefore best suited for intracellular use and other applications which require he folding properties of the scFv. Therefore, in order to reduce the amount of molecules which are not functional in the reducing environment, libraries for intracellular screening systems should preferentially be constructed from a mixture of these framework sub-types.

In a preferred embodiment, the VH domain of the antibody fragments of the invention is of the subgroup 1a, 1b or 3.

In a preferred embodiment, the VL domain of the antibody fragments of the invention is of the subgroup kappa1, lambda 1 or 3.

In a preferred embodiment, antibody fragments used as frameworks are selected from the group consisting of: 1.1, 2.1, 3.1, 4.1, 5.1, 1.2, 2.2, 3.2, 4.2, 5.2, 1.3, 2.3, 3.3, 4.3, 5.3, 7.3, 1.4, 2.4, 3.4, 4.4, 5.4, and 6.4 as described in FIG. 16.

In one embodiment of the invention, at least two and preferably more frameworks are identified and then analyzed. A database of the protein sequences may be established where the protein sequences are aligned with each other. The alignment can then be used to define, for example, residues, sub-elements, sub-sequence or subgroups of framework sequences which show a high degree of similarity in both the sequence and, if that information is available, in the structural arrangement.

The length of the sub-elements is preferably, but not exclusively ranging between 1 amino acid (such as one residue in the active site of an enzyme or a structure-determining residue) and 150 amino acids (for example, whole protein domains). Most preferably, the length ranges between 3 and 25 amino acids, such as most commonly found in CDR loops of antibodies.

In another embodiment, consensus nucleic acid sequences, which are predicted from the analysis are synthesized. This can be achieved by any one of several methods well known to the practitioner skilled in the art, for example, by total gene synthesis or by PCR-based approaches.

In another embodiment, the nucleic acid sequences are cloned into a vector. The vector could be a sequencing vector, an expression vector or a display (e.g. phage display) vector, all which are well known to those of skill in the art. A vector could comprise one nucleic acid sequence, or two or more nucleic sequences, either in different or the same operon. In the last case, they could either be cloned separately or as contiguous sequences.

In one embodiment, the polypeptides have an amino acid pattern characteristic of a particular species. This can for example be achieved by deducing the consensus sequences from a collection of homologous proteins of just one species, most preferably from a collection of human proteins.

A further embodiment of the present invention relates to fusion proteins by providing for a DNA sequence which encodes both the polypeptide, as described above, as well as an additional moiety.

In further embodiments, the invention provides for nucleic acid sequences, vectors containing the nucleic acid sequences, host cells containing the vectors, and polypeptides obtainable according to the methods described herein.

In a further embodiment, the invention provides for synthesizing or otherwise placing restriction sites at the end of the nucleic acid sequences of the invention allowing them to be cloned into suitable vectors.

In a further preferred embodiment, the invention provides for vector systems being compatible with the nucleic acid sequences encoding the polypeptides. The vectors comprise restriction sites, which would be, for example, unique within the vector system and essentially unique with respect to the restriction sites incorporated into the nucleic acid sequences encoding the polypeptides, except for example the restriction sites necessary for cloning the nucleic acid sequences into the vector.

In another embodiment, the invention provides for a kit, comprising one or more of the list of nucleic acid sequences, recombinant vectors, polypeptides, and vectors according to the methods described above, and, for example, suitable host cells for producing the polypeptides.

All of the above embodiments of the present invention can be effected using standard techniques of molecular biology known to one skilled in the art.

In another embodiment, the nucleic acid sequence is any sequence capable of encoding the polypeptides of the invention.

In another embodiment, the inventive nucleic acids are used in gene therapy.

In another embodiment, the single chain framework is a variant of any one of sequences 1.1, 2.1, 3.1, 4.1, 5.1, 1.2, 2.2, 3.2, 4.2, 5.2, 1.3, 2.3, 3.3, 4.3, 5.3, 7.3, 1.4, 2.4, 3.4, 4.4, 5.4, 6.4 (FIG. 16), where "variant" as used herein refers to a sequence that exhibits 90% or greater identity, while maintaining enhanced stability.

In another embodiment, the single chain framework is a derivative of any one of sequences 1.1, 2.1, 3.1, 4.1, 5.1, 1.2, 2.2, 3.2, 4.2, 5.2, 1.3, 2.3, 3.3, 4.3, 5.3, 7.3, 1.4, 2.4, 3.4, 4.4, 5.4, 6.4 (FIG. 16) where "derivative" as used herein refers to a sequence that maintains only those amino acids that are critical to the function and stability of the molecule. Isolated neutral or positive exchanges in the framework as described in example 3, are not considered to be relevant change to the antibody frameworks of the present invention.

In a preferred embodiment of the invention, the single chain framework is fused to a second protein, wherein that protein provides a read-out for intracellular assays. The read-out can be either direct, for example in the form of a fusion to a detectable protein, e.g. GFP (green fluorescent protein), enhanced blue fluorescent protein, enhanced yellow fluorescent, protein enhanced cyan fluorescent protein which can be observed by fluorescence, or other fusion partners with different detection methods. Alternatively, a read-out can be achieved through transcriptional activation of a reporter gene, where the fusion partner in the scFv-fusion protein is either a transcriptional activator, such as the Gal4 activation domain, or a DNA-binding protein, such as the LexA- or Gal4 DNA-binding domain, which activates the transcription of a reporter gene of an enzyme, such as β-galctosidase, luciferase, α-galactosidase, β-glucuronidase, chloramphenicol acetyl transferase and others, which in turn provide a read-out. Fusion proteins, which provide a read out are well known to one of skill in the art.

Another embodiment of the invention is an antibody comprising a framework described herein.

Another embodiment of the invention is the use of the antibody of the instant invention.

A further preferred embodiment of the invention is the use of the described framework classes of antibody variable domains and sequences of variable domains and scFvs for grafting of hypervariable loops from existing antibodies, in order to obtain antibodies which are functional in a reducing or otherwise challenging environment.

Another further preferred embodiment of the invention is the use of the described framework classes of antibody variable domains and sequences of variable domains and scFvs, for example through randomization of one or more of the hypervariable loops of such frameworks, for the creation of libraries for applications in a reducing or otherwise challenging environment.

As would be apparent to one of ordinary skill in the art, the inventive molecules described herein may be used in diagnostic and therapeutic applications, target validation and gene therapy.

The invention may be illustrated by the following examples, which are not intended to limit the scope of the invention in any way.

REFERENCES

Agatep, R., Kirkpatrick, D. L., Parchaliuk, R. A., Woods and Gietz, R. D. (1998). "Transformation of *Saccharomyces cerevisiae* by lithium acetate/single-stranded carrier DNA/polyethylene glycol protocol." *Technical Tips Online* (http://tto.trends.com).

Auf der Maur, A., Escher, D. and Barberis, A. (2001). "Antigen-independent selection of stable intracellular single-chain antibodies." *FEBS Lett* 508: 407-412.

Benvenuto, E. and Tavladoraki, P. (1995). "Immunotherapy of plant viral diseases." *Trends Microbiol* 3(7): 272-5.

Biocca, S. and Cattaneo, A. (1995). "Intracellular immunization: antibody targeting to subcellular compartments." *Trends Cell Biol* 5: 248-252.

Biocca, S., Di Luzio, A., Werge, T. and Cattaneo, A. (1991). "Intracellular immunization: expression of antibody domains in the cytoplasm and in the nucleus of mammalian cells." *Cytotechnology* 5 Suppl 1: 49-50.

Biocca, S., Pierandrei-Amaldi, P. and Cattaneo, A. (1993). "Intracellular expression of anti-p21ras single chain Fv fragments inhibits meiotic maturation of *xenopus oocytes.*" *Biochem Biophys Res Commun* 197(2): 422-7.

Biocca, S., Ruberti, F., Tafani, M., Pierandrei-Amaldi, P. and Cattaneo, A. (1995). "Redox state of single chain Fv fragments targeted to the endoplasmic reticulum, cytosol and mitochondria." *Bio/Technology* 13(10): 1110-5.

Bird, R. E., Hardman, K. D., Jacobson, J. W., Johnson, S., Kaufman, B. M., Lee, S. M., Lee, T., Pope, S. H., Riordan, G. S. and Whitlow, M. (1988). "Single-chain antigen-binding proteins." *Science* 242(4877): 423-6.

Chothia, C. and Lesk, A. M. (1987). "Canonical structures for the hypervariable regions of immunoglobulins." *J. Mol. Biol.* 196(4): 901-17.

Chothia, C., Lesk, A. M., Tramontano, A., Levitt, M., Smith-Gill, S. J., Air, G., Sheriff, S., Padlan, E. A., Davies, D., Tulip, W. R., Colman, W. R., Spinelli, S., Alzari, P. M. and Poljak, R. J. (1989). "Conformations of immunoglobulin hypervariable regions." *J. Mol. Biol.* 342: 877-883.

Johnson, G., Kabat, E. A. and Wu, T. T. (1996). kabat database of sequences of proteins of immunological interest. WEIR'S Handbook of experimental Immunology I Immunochemistry and Molecular Immunology. Cambridge, Mass., Blackwell Science Inv: 6.1-6.21.

Kabat, E. A., Wu, T. T., Perry, H. M., Gottesman, K. S. and Foeller, C. (1991). Sequences of proteins of immunological interest. NIH Publication 91-3242. Wasinghton, DC, US Department of health and human services.

Knappik, A., Ge, L., Honegger, A., Pack, P., Fischer, M., Wellnhofer, G., Hoess, A., Wolle, J., Pluckthun, A. and Virnekas, B. (2000). "Fully synthetic human combinatorial antibody libraries (HuCAL) based on modular consensus frameworks and CDRs randomized with trinucleotides." *J Mol Biol* 296(1): 57-86.

Cochet, O., Kenigsberg, M., Delumeau, I., Virone-Oddos, A., Multon, M. C., Fridman, W. H., Schweighoffer, F., Teillaud, J. L. and Tocque, B. (1998). "Intracellular expression of an antibody fragment-neutralizing p21 ras promotes tumor regression." *Cancer Res* 58(6): 1170-6.

Corpet, F. (1988). "Multalin. Multiple sequence alignment with hierarchical clustering." *Nucleic Acids Res* 16(22): 10881-10890.

Cox, J. P., Tomlinson, I. M. and Winter, G. (1994). "A directory of human germ-line V kappa segments reveals a strong bias in their usage." *Eur J Immunol* 24: 827-836.

de Haard, H. J., van Neer, N., Reurs, A., Hufton, S. E., Roovers, R. C., Henderik, P., de Bruine, A. P., Arends, J.-W. and Hoogenboom, H. R. (1999). "a large non-immunized human Fab fragment phage library that permits rapid isolation and kinetic analysis of high affinity antibodies." *J. Biol. Chem.* 274: 18218-18230.

Escher, D., Bodmer-Glavas, M., Barberis, A. and Schaffner, W. (2000). "Conservation of glutamine-rich transactivation function between yeast and humans." *Mol Cell Biol* 20(8): 2774-82.

Escher, D. and Schaffner, W. (1996). "Improved "activator trap" method for the isolation of transcriptional activation domains from random DNA fragments." *Biotechniques* 21(5): 848-54.

Krebber, A., Bornhauser, S., Burmester, J., Honegger, A., Willuda, J., Bosshard, H. R. and Plückthun, A. (1997). "Reliable cloning of functional variable domains from hybridomas and spleen cell repertoires employing a reengineered phage display system." *J Immunol Methods* 201: 35-55.

Lener, M., Horn, I. R., Cardinale, A., Messina, S., Nielsen, U. B., Rybak, S. M., Hoogenboom, H. R., Cattaneo, A. and Biocca, S. (2000). "Diverting a protein from its cellular location by intracellular antibodies. The case of p21Ras." *Eur J Biochem* 267(4): 1196-205.

Marasco, W. A. (1997). "Intrabodies: turning the humoral immune system outside in for intracellular immunization." *Gene Ther* 4(1): 11-5.

Martineau, P., Jones, P. and Winter, G. (1998). "Expression of an antibody fragment at high levels in the bacterial cytoplasm." *J. Mol. Biol.* 280(1): 117-27.

Ohage, E. and Steipe, B. (1999). "Intrabody construction and expression. I. The critical role of VL domain stability." *J Mol Biol* 291(5): 1119-28.

Ohage, E. C., Wirtz, P., Barnikow, J. and Steipe, B. (1999). "Intrabody construction and expression. II. A synthetic catalytic Fv fragment." *J Mol Biol* 291(5): 1129-34.

Plückthun, A., Krebber, A., Krebber, C., Horn, U., Knüpfer, U., Wenderoth, R., Nieba, L., Proba, K. and Riesenberg, D. (1996). Producing antibodies in *Escherichia coli*: from PCR to fermentation. Antibody Engineering, a practical approach. Oxford, Oxford University Press.

Proba, K., Honegger, A. and Pluckthun, A. (1997). "A natural antibody missing a cysteine in VH: consequences for thermodynamic stability and folding." *J. Mol. Biol.* 265(2): 161-72.

Richardson, J. H. and Marasco, W. A. (1995). "Intracellular antibodies: development and therapeutic potential." *Trends Biotechnol* 13(8): 306-10.

Rondon, I. J. and Marasco, W. A. (1997). "Intracellular antibodies (intrabodies) for gene therapy of infectious diseases." *Annu Rev Microbiol* 51: 257-83.

Skerra, A. and Plückthun, A. (1988). "Assembly of a functional immunoglobulin Fv fragment in *Escherichia coli*." *Science* 240(4855): 1038-41.

Tavladoraki, P., Benvenuto, E., Trinca, S., De Martinis, D., Cattaneo, A. and Galeffi, P. (1993). "Transgenic plants expressing a functional single-chain Fv antibody are specifically protected from virus attack." *Nature* 366(6454): 469-72.

Tomlinson, I. M., Walter, G., Marks, J. D., Llewelyn, M. B. and Winter, G. (1992). "The repertoire of human germline VH sequences revealy about 50 groups of VH segments with different hypervariable loops." *J Mol Biol* 227: 776-798.

Tse, E., Lobato, M. N., Forster, A., Tanaka, T., Chung, G. and Rabbitts, T. (2002). "Intracellular antibody capture technology: application to selection of intracellular antibodies recognising the BCR-ABL oncogenic protein." *J. Mol Biol* 317((1)): 85-94.

Verma, R., Boleti, E. and George, A. J. (1998). "Antibody engineering: comparison of bacterial, yeast, insect and mammalian expression systems." *J Immunol Methods* 216(1-2): 165-81.

Visintin, M., Settanni, G., Maritan, A., Graziosi, S., Marks, J. D. and Cattaneo, A. (2002). "The intracellular antibody capture technology (IACT): towards a consensus sequence for intracellular antibodies." J. *Mol. Biol.* 317((1)): 73-83.

Visintin, M., Tse, E., Axelson, H., Rabbitts, T. H. and Cattaneo, A. (1999). "Selection of antibodies for intracellular function using a two-hybrid in vivo system." *Proc Natl Acad Sci USA* 96(21): 11723-8.

Welschhof, M., Ternesss, P., Kolbinger, F., Zewe, M., Dübel, S., Dörsam, H., Hain, C., Finger, M., Jung, M., Moldenhauer, G., Hayashi, N., Little, M. and Opelz, G. (1995). "Amino acid sequence based PCR primers for amplification of rearranged human heavy and light chain immunoglobulin variable region genes." *J Immunol Methods* 179: 203-214.

Williams, S. C., Frippiat, J. P., Tomlinson, I. M., Ignatovic, O., Lefranc, M. P. and Winter, G. (1996). "Sequence and evolution of the human germline V-lambda repertoire." *J Mol Biol* 264: 220-232.

Wörn, A., Auf der Maur, A., Escher, D., Honegger, A., Barberis, A. and Plückthun, A. (2000). "Correlation between in vitro stability and in vivo performance of anti-GCN4 intrabodies as cytoplasmic inhibitors." *J. Biol. Chem.* 275 (4): 2795-803.

Yokota, T., Milenic, D. E., Whitlow, M. and Schlom, J. (1992). "Rapid tumor penetration of a single-chain Fv and comparison with other immunoglobulin forms." *Cancer Res* 52(12): 3402-8.

Auf der Maur, A., Zahnd, C., Fischer, F., Spinelli, S., Honegger, A., Cambillau, C., Escher, D., Plückthun, A. and Barberis, A. (2002). "Direct in vivo screening of intrabody libraries constructed on a highly stable single-chain framework." *J Biol Chem* 277(47): 45075-45085.

Gietz, R. D. and Sugino, A. (1988). "New yeast-*Escherichia coli* shuttle vectors constructed with in vitro mutagenized yeast genes lacking six-base pair restriction sites" *Gene* 74: 527-534.

Willuda, J., Honegger, A.; Waibel, P., Schubiger, A. Stahel, R., Zangmeister-Wittke, U. and Plückthun, A. (1999). "High thermal stability is essential for tumor targeting of antibody fragments: engineering of a humanized anti-epithelial glycoprotein-2 (epithelial cell adhesion molecule) single-chain Fv fragment" *Cancer Research* 59: 5758-5767.

Wörn, A. and Plückthun, A. (1999). "Different equilibrium stability behavior of scFv fragments: identification, classification, and improvement by protein engineering" *Biochemistry* 38: 8739-8750.

The invention is further illustrated in the following non-limiting examples.

EXAMPLE 1

Selection of intrabody frameworks through screening of a human library in the "quality control" system in yeast Screening with the "quality control" system for stable frameworks was essentially performed as described in detail by Auf der Maur (WO0148017, Auf der Maur 2001, each hereby incorporated by reference).

The plasmids for expression of the scFv-fusion constructs for screening in yeast were derived from pESBA-Act (Wörn, 2000). It contains the yeast TRP1 gene for transformation selection in *S. cerevisiae* and the 2 micron origin of replication to ensure high copy numbers. Moreover it has a constitutive actin promoter for strong expression and the GAL11 transcriptional termination sequence, separated by a multiple cloning site. For handling in bacterial systems, it also has a bacterial origin of replication and the amp resistance gene.

The Gal4 activation domain (AD amino acids 768-881) was originally amplified by PCR using pGAD424 (Clontech) as template with primers including the SV40 T-antigen nuclear localization signal N-terminal to the Gal4-AD. The DNA-fragments encoding amino acids 263-352 of Gal11P were amplified by PCR and cloned in frame, N-terminal to the SV40-NLS-Gal4-AD-construct. The human scFv library, amplified from human spleen-cell cDNA as described elsewhere (Welschhof, 1995; Krebber, 1997; de Haard, 1999), was cloned in frame, N-terminal to this fusion construct via SfiI-sites, and in the orientation $V_L$-linker-$V_H$ where the linker has the sequence $(GGGS)_4$. Expression thus yields a fusion protein of the general structure scFv-Gal11p-SV40 NLS-Gal4AD.

Screening was carried out in the yeast strain *S. cerevisiae* YDE172 (MATα ura3-52 leu2Δ1 trp1d63 his3Δ200 lys2Δ 385 gal4Δ 11) (Auf der Maur, 2001), which was derived from the strain JPY9 (Escher, 2000) by integrating the divergently oriented LacZ and HIS3 reporter genes under the control of the natural $UAS_G$ from Gal1-GAL10 regulatory sequences into the his3Δ200 locus. Transcriptional activation of the reporter system is mediated by the Gal4-AD moiety of the scFv-fusion construct, following the specific interaction of its Gal11P moiety with the Gal4-DNA-binding-domain (DBD, amino acids 1-100). The Gal4-DBD is provided by expression from a second plasmid, pMP83. It contains the yeast LEU2 gene for transformation selection in *S. cerevisiae* and the ARS CEN origin of replication. Moreover, it has a constitutive actin promoter for strong expression and the GAL11 transcriptional termination sequence. For handling in bacterial systems, it also has a bacterial origin of replication and the amp resistance gene.

For screening, the yeast strain *S. cerevisiae* YDE172 was co-transformed with a scFv-library as fusion construct on the pESBA-Act2 vector while the pMP83-vector provided the Gal4-DBD. A standard lithium acetate transformation protocol was used (Agatep, 1998). Following transformation, the cells were plated on drop-out plates (-Trp/-Leu/-His) containing 80 mM 3-aminotriazole. Colonies were picked after 3 days incubation at 30° C. and restreaked on drop-out plates (-Trp/-Leu/-His) containing 80 mM 3-aminotriazole. Those that re-grew were tested for LacZ-expression by development of blue color in a filter assay on plates containing the substrate X-Gal. Positive clones were taken for further analysis involving isolation of the scFv-carrying plasmid from yeast, transformation into *E. coli* DH5α, isolation of plasmid from single colonies of *E. coli* and re-transformation into freshly prepared yeast strain *S. cerevisiae* YDE172 for the assay as described below. All methods were performed according to standard procedures, well known to a person of ordinary skill in the art.

In addition, a modified screening procedure was used were the scFv was directly fused to both a DNA-binding domain (LexA amino acids 1-202) and an activation domain (Gal4, amino acids 768-881) to yield a fusion construct of the following structure: scFv-LexA-NLS-Gal4AD. The plasmids for expression of the scFv-fusion constructs for screening in yeast were derived from pESBA-Act2. It contains the yeast TRP1 gene for transformation selection in *S. cerevisiae* and the 2 micron origin of replication to ensure high copy numbers. Moreover, it has a constitutive actin promoter (for strong expression) and the GAL11 transcriptional termination sequence separated by a multiple cloning site. For handling in bacterial systems, it also has a bacterial origin of replication and the amp resistance gene.

Screening was carried out in the yeast strain *S. cerevisiae* ImmunaLHB (MATα ura3-52 leu2Δ1 trp1d63 his3Δ200 lys2Δ 385) which was derived from the strain JPY5 by integrating the divergently oriented LacZ and HIS3 reporter genes under the control of a bi-directional promoter with six LexA-binding sites (integrating reporter plasmid pDE200, Escher 2000) into the his3Δ200 locus and by integrating the LEU2 reporter gene under the control of a promoter with eight LexA-binding sites (derived from EGY48) into the leu2Δ1 locus. Transcriptional activation of the reporter system is mediated by the Gal4-AD moiety of the scFv-fusion construct. Screening was carried out essentially as described above using drop-out medium (-Trp/-Leu/-His) and 3-aminotriazole concentrations up to 40 mM.

EXAMPLE 2

Evaluation of In Vivo Performance a) In Yeast

For quantitative analysis of the performance of the selected frameworks in yeast (FIGS. 1 and 3), *S. cerevisiae*-strain Immuna LHB was transformed with the isolated scFvs as LexA-Gal4-AD-fusion constructs on the pESBA-Act2 vector by following a standard lithium acetate transformation protocol (Agatep, 1998). Following transformation, the cells were plated on drop-out plates (Trp). 2 ml overnight-cultures in drop-out medium (-Trp) were inoculated in duplicates from streaks containing several colonies and grown at 30° C. Cultures were diluted in 1 ml drop-out medium (-Trp) to an optical density at 600 nm (OD600) of 0.7. They were then grown at 30° C. for 2 h. For the assay, 100 µl cell culture were taken, mixed with 900 µl buffer, 45 µl Chloroform and 30 µl 0.1% SDS, vortexed and incubated at room temperature for 5 minutes. The color development was initiated by the addition of 0.2 ml ONPG (4 mg/ml) and stopped with 0.5 ml $Na_2CO_3$ (1 M). The activity was calculated by taking into account the OD600 of the assay culture, as well as the incubation time of the color development and the culture volume used Clones that were at least equal to or better than the positive control (the very stable lambda-graft described before (Wörn, 2000; Auf der Maur, 2001)) were sequenced to identify the framework subtype (framework subtype definitions according to Tomlinson, (1992), Cox, (1994) and Williams, (1996)). Sequencing revealed a striking preference for certain framework subtypes. For the heavy chain variable domain (VH), framework subtypes 2 and 6 were never found and 4 was markedly reduced among the positive clones. Corrected for the performance of the isolated sequences in the yeast intracellular assay, there is a very strong preference for VH framework of the subtype 3, but also for 1a and 1b in intracellular applications. Regarding the light chain variable domain (VL), there is a clear preference for frameworks of the kappa 1, lambda 1 and lambda 3 sub-types (FIG. 15).

These framework subtypes, i.e. VH 1a, 1b and 3 combined with a kappa 1, lambda 1 and lambda 3 VL domain are therefore best suited for intracellular use and other applications with stringent requirements concerning the folding properties of the scFv. Libraries for intracellular screening systems should, for example, preferentially be constructed from a mixture of these framework subtypes only, to reduce the amount molecules which are not functional in the reducing environment.

b) In Mammalian Cells

Figure 4:
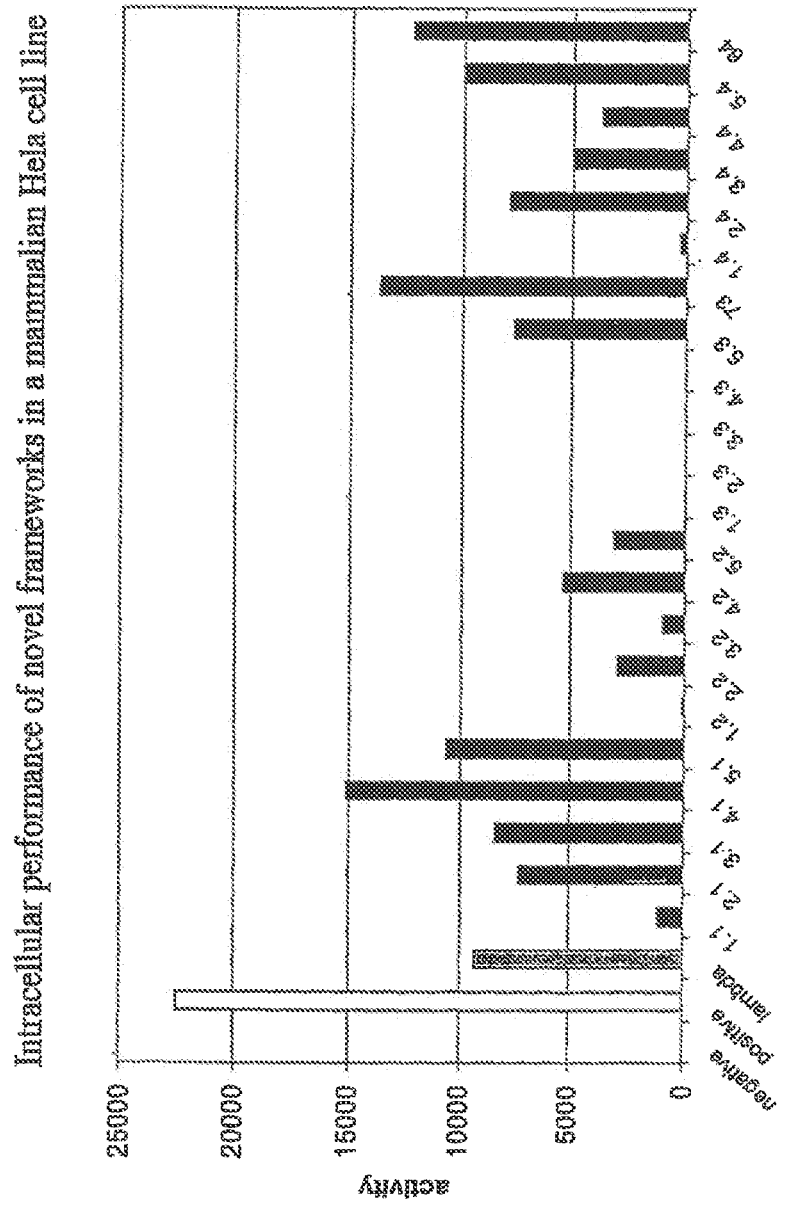
FIG. 4 shows the in vivo performance of the superior framework combinations assayed in the human cell line Hela by the activation of luciferase expression and illustrated in comparison to the very stable lambda-graft (dark grey). The positive control, Gal4-VP16 (white) gives the maximal possible level of transcriptional activation in the system. Luciferase activity has been corrected for transfection efficiency.
Figure 5:
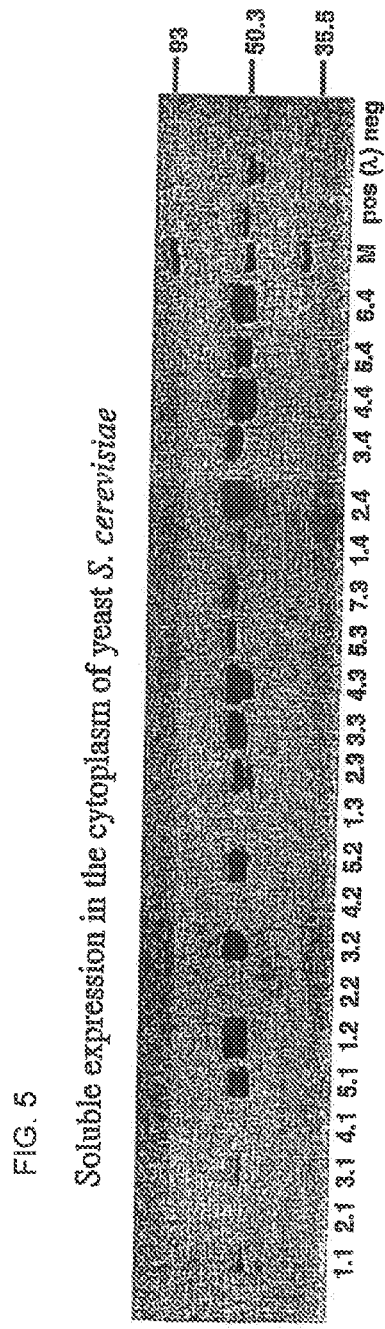
FIG. 5 shows the in vivo performance of the superior framework combinations assayed by the amount of soluble protein produced in the cytoplasm of yeast strain S. cerevisiae JPY9.
Figure 7:
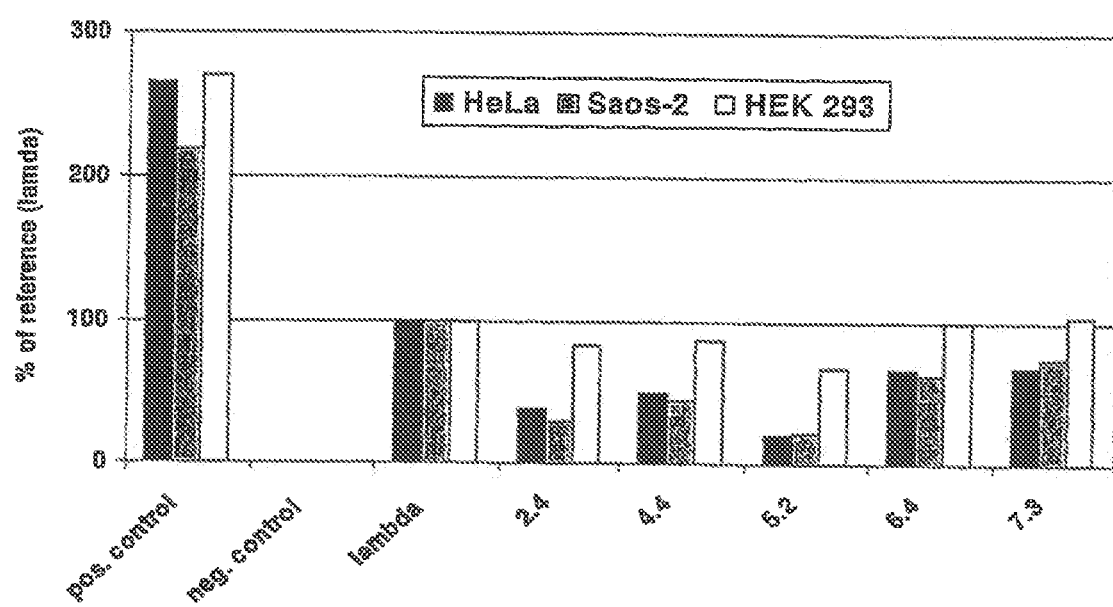
FIG. 7 shows the in vivo performance of selected superior framework combinations assayed in three human cell lines (Hela, (black), Saos-2 (dark grey) and HEK 293 (white)), by the activation of luciferase expression and illustrated in comparison to the very stable lambda-graft. The positive control Gal4-VP16 gives the maximal possible level of transcriptional activation in the system. Luciferase activity has been corrected for transfection efficiency.

Hela cell line was used for quantitative analysis of the performance of the selected frameworks in human cells (FIGS. 2, 4 and 7). The luciferase reporter gene was provided from a co-transfected pGL3 (Promega) reporter plasmid containing the luciferase under the control of the natural Gal4 UAS. The mammalian expression vectors used for transient transfection contains the Gal4 (1-147) fused on the C-terminus to the VP16-AD under the control of a CMV promoter. The isolated scFvs were cloned in frame, C-terminal to a Gal4(1-147)-VP16-fusion to yield a Gal4(1-147)-VP16-scFv-fusion protein upon expression. Cells were cultured in DMEM supplemented with 2.5% FCS and 2 mM l-glutamine. Transient transfections were carried out according to the Polyfect-protocol (Qiagen) in 60 mm tissue culture plates using 0.01-0.1 µg of the vector containing the scFv-construct, 0.5 µg of a CMV promoter-driven Gal4(1-147)-VP16-scFv expression plasmid and 0.5 µg of a LacZ expression vector as reference for transfection efficiency. Cells were harvested 24-48 hours after transfection, resupended in 1000 µl buffer and lysed by three freeze-thaw-cycles. The cell lysate was centrifuged and the supernatant assayed for luciferase activity using luciferase assay solution (Promega) and for LacZ activity according to the standard protocol. The obtained luciferase activity was corrected with the LacZ activity to account for the variation in transfection efficiency.

EXAMPLE 3

Multiple Alignment and Analysis of the Sequence Comparison

To elucidate the general pattern of framework sequences suitable for intracellular applications, all positive clones (i.e. those that grow under selective conditions in the quality control system) were isolated and the part coding for the scFvs was sequenced. Subsequently, the scFv sequences were divided in their light and heavy-chain component to allow alignment of the respective domains (FIGS. 12 and 13) according to the structural adjusted numbering scheme of immunoglobulin domains by Honegger (2001).

To allow evaluation of the obtained data, an alignment representing the unselected library was generated (FIG. 14). In order to obtain unselected sequences, the library was transformed in E. coli cells which do not express the scFv-genes and clones were picked at random for plasmid isolation and sequencing of the scFv-sequence. The library covers the human antibody repertoire as expected and thus has no bias towards specific subgroups, other than expected by the expression pattern generally found in humans.

The VH and VL sequences were grouped according to their subgroup. Changes to the subgroup-specific consensus sequence were highlighted. A person skilled in the art can distinguish between positive, neutral and negative changes based on the structural environment of the particular exchanged residue (e.g. Honegger, 2001). An exchange of a residue belonging to a particular group of amino acids to a residue of the same group is in general validated as a neutral exchange. An exchange of a residue belonging to the group of hydrophobic amino acid pointing into the hydrophobic core of the protein to one amino acid of the group of polar but uncharged or positively or negatively charged amino acids would be highly unfavorable because unsatisfied hydrogen donor/acceptor sites disturb tight packing of the hydrophobic core. Such a change is therefore considered negative. An exchange of a residue belonging to the group of polar but uncharged residues at the surface of the immunoglobulin domain to an amino acid of the group of positively or negatively charged residues is highly favorable as the solubility of the protein is increased. Such a change is therefore validated positively, whereas the exchange from a polar to a hydrophobic residue is highly unfavorable as the solubility of the protein is decreased and is therefore validated negatively. At positions with a conserved positive phi-angle, an exchange of any amino acid to glycine is validated positively whereas an exchange of gylcine to any amino acid is validated negatively because glycine is the only amino acid which is able to form a positive phi-angle. The loss of a conserved salt bridge between positions 45-53, 45-100, 77-100 and 108-137 because of an exchange from an amino acid of the group of positively or negatively charged residues to an uncharged amino acid results in a decreased thermodynamic stability and is therefore considered negative.

Finally, we chose 7 VL domains and 4 VH domains that were preferentially selected during the quality control (i.e. showing the least negative and most positive exchanges from the consensus sequence and cover the subgroups) and that each show high in vivo performance in yeast. The sequences are summarized in FIG. 16 and include two Vκ1 (k I 27 (1.x) and k III 25(2.x)), two Vκ3 (k IV 103 (3.x) and k IV135 (5.x)), one Vλ1 (k IV 107 (4.x)), two Vλ3 (a33 (7.x) and a43 (6.x)), one VH1b (a33 (x.3)) and three VH3 (a fw10 (x.2), a43 (x.4) and a44 (x.1)). These VL and VH domains were shuffled giving 22 novel combinations in the scFv format (1.1, 2.1, 3.1, 4.1, 5.1, 1.2, 2.2, 3.2, 4.2, 5.2, 1.3, 2.3, 3.3, 4.3, 5.3, 7.3, 1.4, 2.4, 3.4, 4.4, 5.4, 6.4).

EXAMPLE 4

Figure 3:
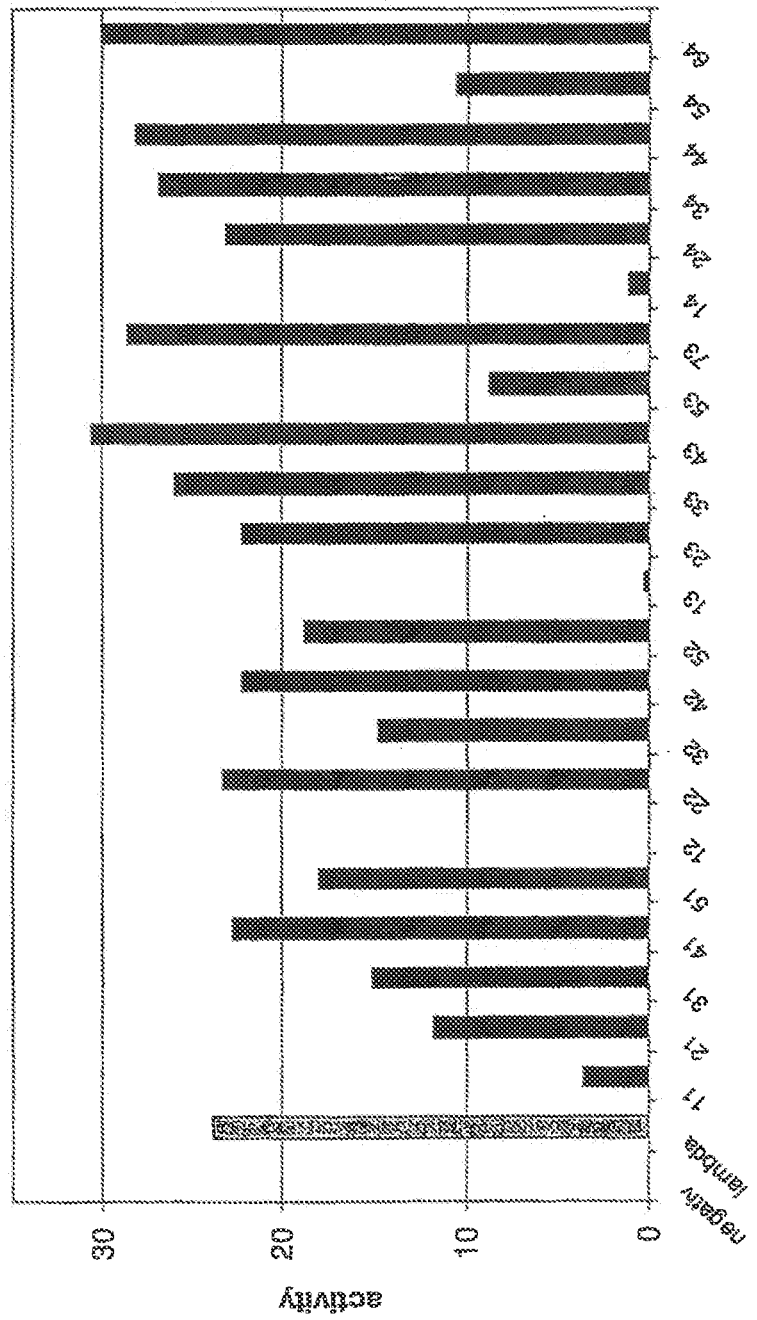
FIG. 3 shows the in vivo performance of the superior framework combinations assayed in yeast by the activation of lacZ expression. The framework sequences (black) are compared to the positive control (the very stable lambda-graft (dark grey)). The numbering of the frameworks is as described in FIG. 16.

Evaluation of In Vivo Performance of Shuffled Domains a) Performance in an Intracellular Assay in Yeast and Mammalian Cells The 22 combinations were tested for their in vivo performance in yeast and mammalian cells as described in example 2 (FIGS. 3 and 4).

b) Expression of Soluble Protein Under Reducing Conditions in Yeast

To compare the yields of soluble protein upon expression under reducing conditions, the selected frameworks were expressed as a fusion to Gal4 AD in the cytoplasm of yeast S. cerevisiae. The fusion constructs on the pESBA-Act2 vector had the general structure Gal4 AD-scFv. They were transformed as described above into the yeast S. cerevisiae strain JPY9 and plated on -Trp, drop-out plates.

5 ml overnight-cultures in drop-out medium (-Trp) were inoculated from streaks containing several colonies and grown at 30° C. Cultures were diluted in 50 ml drop-out medium (-Trp) to an optical density at 600 nm (OD600) of 0.5. They were grown at 30° C. for 5 h. For the native cell extract, 2.5 ml cell culture normalized to an OD600 of 3 were harvested by centrifugation, frozen in liquid nitrogen and subsequently resuspended in 75 µl Y-PER (Pierce) containing protease inhibitor (PMSF). The resuspended cell pellet was vortexed shortly and incubated (slightly shaking) at 20° C. for 20 min. Insoluble and aggregated material was pelleted at maximal speed in an eppendorf centrifuge at 4° C. for 10 min. The supernatant was mixed with loading dye, heated to 100° C. for 5 min. and separated on a 12% SDS-PAGE. The soluble Gal4 AD-scFv fusion constructs were visualized by western blotting via detection of the Gal4-moiety with an anti-Gal4AD monoclonal mouse antibody (Santa Cruz Biotechnology) as a primary antibody and an anti-mouse-peroxidase conjugate (Sigma) as secondary antibody and using a chemoluminescent substrate (Pierce) (FIG. 5). SDS-PAGE and western blotting procedures are well known to a person of ordinary skill in the art.

c) Expression Behavior in the Periplasm of E. coli

For evaluation of periplasmic expression behavior in E. coli (FIG. 6), isolated scFvs-frameworks were cloned in a bacterial vector harbouring the cam resistance gene (catR) and the lacI repressor gene (Krebber, 1997), with a N-terminal pelB-leader sequence and a C-terminal his-tag under the control of the lac promoter/operator. Competent E. coli JM83 were transformed with these plasmids. 50 ml dYT-medium containing 35 mg/l chloramphenicol in shaking flasks was inoculated 1:40 with an over-night culture and incubated at 30° C. Cells were induced at an OD600 of 0.8 with 1 mM IPTG and harvested after 3 hours of induction by centrifugation. The pellet was resuspended in 50 mM Tris, pH 7.5, 500 mM NaCl and normalized to an OD600 of 10. Samples of each scFv fragments were analyzed either directly (total extract) or after sonication followed by centrifugation (soluble fraction) by SDS-PAGE. The amount of soluble protein was estimated from the Coomassie-stained gel.

EXAMPLE 5

Detailed Evaluation of 5 Combinations with Superior Properties for Extracellular Use Five combinations were chosen as examples which show good performance both in yeast and mammalian intracellular assays, yield soluble protein during expression in yeast and E. coli, and cover the subgroups which were preferentially selected during the quality control (2.4, 4.4, 5.2, 6.4 and 7.3, see FIG. 16 for details). We analysed these combinations in greater detail to further evaluate their use under reducing, as well as oxidizing conditions.

a) Performance in an Intracellular Assay in Different Mammalian Cells

The quantitative analysis of the performance of the five combinations in human cells was carried out using Hela cells and in addition using the human osteosarcoma cell line Saos-2 and the human embryonal kidney cell line HEK293 as performed in Example 2 (FIG. 7).

b) Performance In Vitro

Expression and Purification

Figure 6:
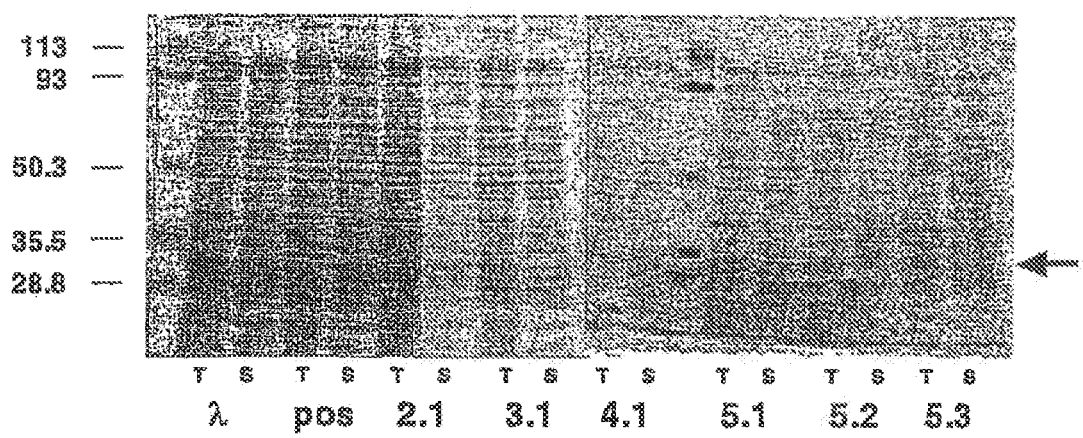
FIG. 6A shows the expression behavior of selected framework combinations (2.1, 3.1, 4.1, 5.1, 5.2, and 5.3) in the periplasm of E. coli. The arrow indicates the location of the band corresponding to the scFv frameworks.
FIG. 6B shows the expression behavior of selected framework combinations (7.3, 2.4, 3.4, 4.4, 5.4, and 6.4) in the periplasm of E. coli. The arrow indicates the location of the band corresponding to the scFv frameworks.
Figure 6B:
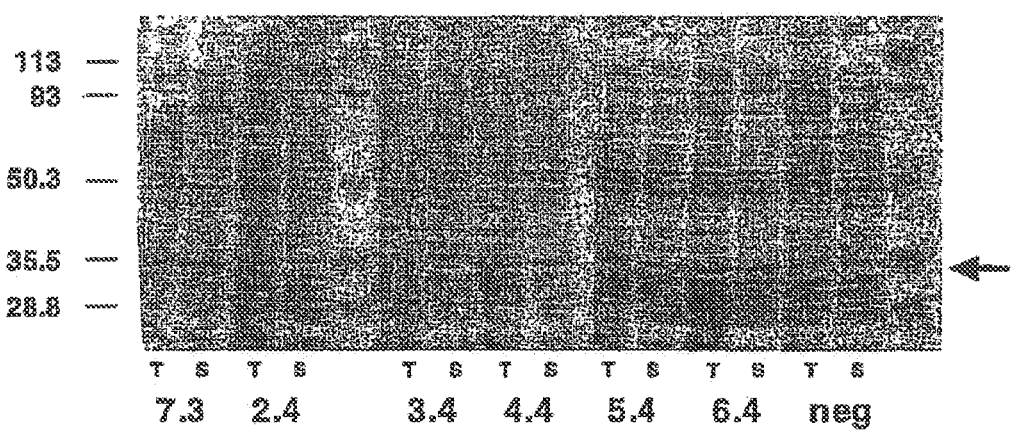

For evaluation of the in vitro performance, the five superior combinations were expressed in the periplasm of E. coli (FIG. 6). The amount of 0.1 l dYT-medium containing 35 mg/l chloramphenicol in shaking flasks was inoculated 1:40 with an over-night culture and incubated at 30° C. Cells were induced at an OD550 of 1.5 with 1 mM IPTG and harvested after 2 hours of induction by centrifugation. For purification of the scFvs, the cell pellet was resuspended and lysed by sonication. Following centrifugation in SS34 at 20 krpm, 4° C. for 30 minutes, the supernatant was applied to a Ni-MC-affinity column (HiTrap™ Chelating HP, 1 ml, Amersham Pharmacia) at pH 7.5 and eluted with 200 mM imidazol using an Äkta Basic system from Amersham Pharmacia. The purity of the scFv fragments was greater than 98% as determined by SDS-PAGE (data not shown). The concentration of the purified protein was determined using the calculated extinction coefficient at 280 nm. The yield of soluble purified protein was normalized to a culture volume of 1 l with an OD600 of 10 and varied from 8 to over 55 mg.

Resistance to Aggregation

Resistance towards aggregation has been shown to correlate with thermodynamic stability (Wörn, 1999) in vitro and the efficiency of tumor localization in a xenografted tumor model in mice (Willuda, 1999). In order to test for the stability, resistance to aggregation and reversibility of unfolding, 200 µl samples of the purified proteins at concentrations of 6 µM in 50 mM Tris, pH 7.5, 100 mM NaCl were either kept 4 days at 4° C. or 4 days at 37° C. or 3 days at 4° C. followed by an incubation of 15 or 60 minutes at 100° C., slow cooling down to room temperature and an overnight incubation at 4° C. The oligomeric state of each sample was subsequently analyzed on a gel filtration column equilibrated with 50 mM Tris, pH 7.5, 100 mM NaCl to estimate the amount of aggregated versus monomeric material (FIG. 8). The proteins were injected on a Superdex-75 column (Amersham Pharmacia) in a volume of 100 µl and a flow-rate of 1 ml/min on a Äkta Basic system (Amersham Pharmacia).

Resistance to Protease Degradation

To determine the stability of the isolated frameworks towards protease degradation, a parameter that is important for therapeutic applications, we incubated the purified frameworks in human serum at 37° C. (FIG. 9).

Purified, his-tagged scFv-protein (see above) at a concentration of 50 µM was diluted tenfold into human serum to a final concentration of 5 µM in 90% serum. The samples were then either incubated at 37° C. for either 3 days or 1 day, or taken directly for loading. Before loading insoluble and aggregated material was pelleted at maximal speed in an eppendorf centrifuge at 4° C. for 10 min. The supernatant was diluted six-fold with a loading dye to reduce the amount of serum loaded on the gel, heated to 100° C. for 5 min. and separated on a 12% SDS-PAGE. The soluble his-tagged scFv fragments were visualized by western blotting via detection of the his-tag with an anti-his monoclonal mouse antibody (Qiagen) as primary and an anti-mouse-peroxidase conjugate (Sigma) as secondary antibody and using a chemoluminescent substrate (Pierce). SDS-PAGE and western blotting procedures are well known to a person of ordinary skill in the art.

EXAMPLE 6

Selection of antigen binders through screening of a randomized CDR-library on the framework 7.3 in the interaction screening system in yeast Screening with the interaction system for antigen binders was essentially performed as described in detail before (Auf der Maur, 2002).

The plasmids for expression of the scFv-fusion constructs for screening in yeast were derived from pESBA-Act2. It contains the yeast TRP1 nutritional marker and the 2 micron origin of replication. Moreover it has a constitutive actin promoter for strong expression and the GAL11 transcriptional termination sequence, separated by a multiple cloning site. For handling in bacterial systems, it also has a bacterial origin of replication and the amp resistance gene.

The Gal4 activation domain (AD amino acids 768-881) was originally amplified by PCR using pGAD424 (Clontech) as template with primers including the SV40 T-antigen nuclear localization signal N-terminal to the Gal4-AD. The scFv library was obtained by PCR-amplification of the scFv-framework 7.3 using primers randomizing 7 amino acids within the CDR3 of VH. The resulting PCR-product was cloned in the framework 7.3, present in the vector in the orientation V$_L$-linker-V$_H$, as a C-terminal fusion to Gal4-AD. Expression thus yields a fusion protein of the general structure Gal4-AD-scFv.

Screening was carried out in the yeast strain *S. cerevisiae* Immuna LHB (MATα ura3-52 leu2Δ1 trp1d63 his3Δ200 lys2Δ 385). It was derived from the strain JPY5 by integrating the divergently oriented LacZ and HIS3 reporter genes under the control of a bi-directional promoter with six LexA-binding sites (integrating reporter plasmid pDE200, Escher 2000) into the his3Δ200 locus and by integrating the LEU2 reporter gene under the control of a promoter with eight LexA-binding sites (derived from EGY48) into the leu2Δ1 locus.

Transcriptional activation of the reporter system is mediated by the Gal4-AD moiety of the scFv-fusion construct, following the specific interaction of its scFv moiety with the antigen-moiety of the bait-fusion protein. The bait-fusion protein consists of the kinase domain of the human polo-like kinase 1 (hPlk1-KD) fused C-terminal to the DNA-binding LexA protein. The kinase domain (amino acid 2-332) was PCR amplified from a hPlk1 cDNA using the upstream primer 5'-tgctctagaagt gctgcagtgactgcag-3' (Seq. Id.No. 12) and downstream primer 5'-ggttgtcgacttacaggctgctgggag-caatcg-3' (Seq. Id. No. 13). The resulting PCR product was cloned C-terminal of LexA via XbaI and SalI into the bait vector. The bait vector contains the URA3 nutritional marker and an Ars Cen origin of replication. Expression of the bait-fusion protein is driven by a constitutively active actin promoter. Transcription is terminated by the GAL11 termination sequence. The bait vector also carries a bacterial origin of replication and the amp resistance gene for propagation in bacterial systems.

For screening the yeast strain *S. cerevisiae* Immuna LHB was co-transformed with a scFv-library as fusion to Gal4-AD on the pESBA-Act2 vector and the bait-vector providing the LexA-hPLK1-KD fusion by following a standard lithium acetate transformation protocol (Agatep, 1998). Following transformation, the cells were plated on drop-out plates (-Trp/-Leu/-Ura). Colonies were picked after 3 to 5 days incubation at 30° C. and restreaked on drop-out plates (-Trp/-Leu/-Ura). Those that re-grew were tested for LacZ expression by development of blue color in a filter assay on plates containing the substrate X-Gal. Positive clones were taken for further analysis involving isolation of the scFv-carrying plasmid from yeast, transformation into *E. coli* DH5α, isolation of plasmid from single colonies of *E. coli*, sequencing and re-transformation into freshly prepared yeast strain *S. cerevisiae* Immuna LHB for the assay as described below. All methods were performed according to standard procedures, well known to a person of ordinary skill in the art.

EXAMPLE 7

Evaluation of In Vivo Performance of Fab-Constructs Derived from Novel scFv Frameworks To evaluate the beneficial effect of using stable variable domain frameworks on different antibody formats, Fab expression vector were constructed for use in the yeast interaction screen.

a) Fab Constructs for Intracellular Screening in Yeast

Two different expression vectors were constructed to allow different expression levels. The vectors are based on either yEplac 112 (2 micron) or yCplac22 (ars/cen) backbones (Gietz, 1988). Both contain the yeast TRP1 nutritional marker, an inducible, bi-directional Gal1/Gal10 promoter, a bacterial origin of replication and the amp resistance gene for handling in bacterial systems. In one direction, the VH domain of the framework 7.3 was cloned N-terminal to the CH1-domain of IgG1 including the C-terminal cysteine, followed by a linker and the Gal4 activation domain (AD amino acids 768-881) including the SV40 T-antigen. On the other side, the VL domain of the framework 7.3 was cloned N-terminal to the CL (lambda)-domain including the C-terminal cysteine. The terminators are Gal11 terminator on the side of the heavy chain and Cyclin 1 terminator on the side of the light chain.

b) Performance in an Intracellular Assay in Yeast

For quantitative analysis of the performance of the antigen binders in scFv and Fab format in yeast (FIGS. 1 and 3), *S. cerevisiae* strain Immuna LHB was co-transformed with the isolated scFvs as Gal4-AD-fusion constructs on the pESBA-Act2 vector and the bait vector containing the LexA-hPLK1-KD fusion by following a standard lithium acetate transformation protocol (Agatep, 1998). Following transformation, the cells were plated on drop-out plates (-Trp, -Ura, Glc). 2 ml overnight-cultures in drop-out medium (-Trp, -Ura, Glc) were inoculated in duplicates from streaks containing several colonies and grown at 30° C. Cultures were diluted in 1 ml drop-out medium (-Trp, -Ura, Gal) to an optical density at 600 nm (OD600) of 0.7. They were grown at 30° C. for 5 h. The assay was carried out as described above.

c) Expression of Soluble Protein Under Reducing Conditions in Yeast

To compare the yields of soluble protein upon expression under reducing conditions, the scFv and Fab constructs, together with the hPLK1-KD-bait vector, as described above were expressed in the cytoplasm of yeast *S. cerevisiae*. They were transformed as described above into the yeast strain YDE173 and plated on -Trp, -Ura, drop-out plates containing glucose.

Figure 11:
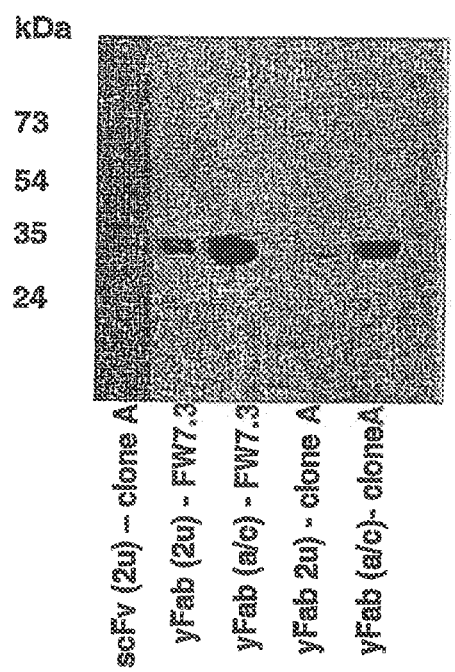
FIG. 11 shows the in vivo performance of the scFv frameworks in the Fab-context assayed by the amount of soluble protein produced in the cytoplasm of the yeast strain JPY9. Expression of the Gal4-AD-scFv fusion (actin/2 micron) is compared with the expression of the corresponding Fab-construct, and with the parent framework 7.3 as a Fab, both from two different vectors (Gal-inducible, ars/cen and 2 micron). Expression from the Fab vector yields the antibody light chain and a VH-CH1-Gal4-AD fusion protein, which is detected in this blot.

5 ml overnight-cultures in drop-out medium (Trp, -Ura, Glc) were inoculated from streaks containing several colonies and grown at 30° C. Cultures were diluted in YPAG to an optical density at 600 nm (OD600) of 0.5. They were grown at 30° C. for 7.5 h. For the native cell extract, 2.5 ml cell culture normalized to an OD600 of 3 were harvested by centrifugation, frozen in liquid nitrogen and subsequently resuspended in 75 μl Y-PER (Pierce). The resuspended cell pellet was vortexed shortly and incubated slightly shaking at 20° C. for 20 min. Subsequently insoluble and aggregated material were pelleted at maximal speed in an eppendorf centrifuge at 4° C. for 10 min. The supernatant was mixed with loading dye, heated to 100° C. for 5 min and separated on a 12% SDS-PAGE. The soluble Gal4-AD-scFv fusion and the heavy chain part of the Fab fused to the Gal4-AD were visualized by western blotting via detection of the Gal4-moiety with an anti-Gal4-AD monoclonal mouse antibody (Santa Cruz Biotechnology) as primary and an anti-mouse-peroxidase conjugate (Sigma) as secondary antibody and using a chemoluminescent substrate (Pierce) (FIG. 11). SDS-PAGE and western blotting procedures are well known to a person of ordinary skill in the art.

The invention claimed is:

1. A method for generation of a library comprising single chain antibodies with high stability and solubility, the method comprising;

a) randomization of one or more of the hypervariable loops of a single chain antibody, wherein the single chain antibody comprises a framework selected from the group consisting of:

AK, BK, CK, DK, EK, FK, and GK:

wherein A is the amino acid sequence (Seq. Id. No. 1)
EIVMTQSPSTLSASVGDRVIITCRASQSISSWLAWYQQKPGKAPKLLIYK
ASSLESGVPSRFSGSGSGAEFTLTISSLQPDDFATYYCQQYKSYWTFGQG
TKLTVLG;

B is the amino acid sequence (Seq. Id. No. 2)
EIVLTQSPSSLSASVGDRVTLTCRASQGIRNELAWYQQRPGKAPKRLIYA
GSILQSGVPSRFSGSGSGTEFTLTISSLQPEDVAVYYCQQYYSLPYMFGQ
GTKVDIKR;

C is the amino acid sequence (Seq. Id. No. 3)
EIVMTQSPATLSVSPGESAALSCRASQGVSTNVAWYQQKPGQAPR
LLIYGATTRASGVPARFSGSGSGTEFTLTINSLQSEDFAAYYCQQYKHWP
PWTFGQGTKVEIKR;

D is the amino acid sequence (Seq. Id. No. 4)
QSVLTQPPSVSAAPGQKVTISCSGSTSNIGDNYVSWYQQLPGTAPQLLIY
DNTKRPSGIPDRFSGSKSGTSATLGITGLQTGDEADYYCGTWDSSLSGVV
FGGGTKLTVLG;

E is the amino acid sequence (Seq. Id. No. 5)
EIVLTQSPATLSLSPGERATLSCRASQTLTHYLAWYQQKPGQAPR
LLIYDTSKRATGVPARFSGSGSGTDFTLTISSLEPEDSALYYCQQRNSWP
HTFGGGTKLEIKR;

F is the amino acid sequence (Seq. Id. No. 6)
SYVLTQPPSVSVAPGQTATVTCGGNNIGSKSVHWYQQKPGQAPVL
VVYDDSDRPSGIPERFSGSNSGNTATLTIRRVEAGDEADYYCQVWDSSSD
HNVFGSGTKVEIKR;

G is the amino acid sequence (Seq. Id. No. 7)
LPVLTQPPSVSVAPGQTARISCGGNNIETISVHWYQQKPGQAPVL
VVSDDSVRPSGIPERFSGSNSGNTATLTISRVEAGDEADYYCQVWDSSSD
YVVFGGGTKLTVLG;
and K is the amino acid sequence (Seq. Id. No. 11)
EVQLVESGGGLVQPGGSLRLSCAASGFTFSSYAMSWVRQAPGKGL
EWVSAISGSGGSTYYADSVKGRFTISRDNSKNTLYLQMNSLRAEDTAVYY
CAKDAGIAVAGTGFDYWGQGTLVTVSS, b) expressing the single chain antibodies of the library and
c) screening the single chain antibodies for stability and solubility.

* * * * *